US012558330B2

(12) United States Patent
Radhakrishnan et al.

(10) Patent No.: US 12,558,330 B2
(45) Date of Patent: *Feb. 24, 2026

(54) METHODS AND COMPOSITIONS FOR TREATING EDEMA REFRACTORY TO ORAL DIURETICS

(71) Applicant: RESQ Pharmaceuticals LLC, Orange, CA (US)

(72) Inventors: Balasingam Radhakrishnan, Chapel Hill, NC (US); Ben Esque, Huntington Beach, CA (US); Wei Lin, San Diego, CA (US); Andrew Xian Chen, San Diego, CA (US)

(73) Assignee: RESQ Pharmaceuticals LLC, Orange, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/208,335

(22) Filed: May 14, 2025

(65) Prior Publication Data

US 2025/0268853 A1 Aug. 28, 2025

Related U.S. Application Data

(63) Continuation of application No. 18/916,471, filed on Oct. 15, 2024, now Pat. No. 12,329,731, which is a continuation of application No. 17/680,591, filed on Feb. 25, 2022, now Pat. No. 12,150,923, which is a continuation of application No. 17/345,550, filed on Jun. 11, 2021, now Pat. No. 11,260,038, which is a continuation of application No. 17/112,899, filed on Dec. 4, 2020, now Pat. No. 11,123,319.

(60) Provisional application No. 62/943,638, filed on Dec. 4, 2019.

(51) Int. Cl.

| | |
|---|---|
| *A61K 31/196* | (2006.01) |
| *A61K 9/00* | (2006.01) |
| *A61K 9/107* | (2006.01) |
| *A61K 47/38* | (2006.01) |
| *A61P 7/10* | (2006.01) |
| *A61P 9/04* | (2006.01) |

(52) U.S. Cl.
CPC .......... *A61K 31/196* (2013.01); *A61K 9/0019* (2013.01); *A61K 9/0043* (2013.01); *A61K 9/006* (2013.01); *A61K 9/107* (2013.01); *A61K 47/38* (2013.01); *A61P 7/10* (2018.01); *A61P 9/04* (2018.01)

(58) Field of Classification Search
CPC .... A61K 31/196; A61K 47/38; A61K 9/0019; A61K 9/0043; A61K 9/006; A61K 9/107; A61P 7/10; A61P 9/04
See application file for complete search history.

(56) References Cited

U.S. PATENT DOCUMENTS

| | | | |
|---|---|---|---|
| 7,981,401 | B2 | 7/2011 | Every et al. |
| 11,123,319 | B2 | 9/2021 | Radhakrishnan et al. |
| 11,260,038 | B1 | 3/2022 | Radhakrishnan et al. |
| 12,150,923 | B2 | 11/2024 | Radhakrishnan et al. |
| 12,329,731 | B2 | 6/2025 | Radhakrishnan et al. |
| 2012/0277249 | A1 | 11/2012 | Andersson et al. |
| 2013/0022622 | A1 | 1/2013 | Ben-Ari et al. |
| 2014/0066504 | A1 | 3/2014 | Hochman et al. |
| 2014/0128469 | A1 | 5/2014 | Tung |
| 2017/0172971 | A1 | 6/2017 | Andersson et al. |
| 2019/0151263 | A1 | 5/2019 | Partridge et al. |
| 2022/0287996 | A1 | 9/2022 | Radhakrishnan et al. |
| 2024/0285566 | A1 | 8/2024 | Radhakrishnan et al. |

FOREIGN PATENT DOCUMENTS

| | | |
|---|---|---|
| CN | 106572984 A | 4/2017 |
| IN | 2476/MUM/2011 A | 3/2013 |
| WO | WO-2019/193161 A1 | 10/2019 |

OTHER PUBLICATIONS

Ong et al. (CrystEngComm, 2012, 14, 2428-34). (Year: 2012).*
West-Ward (Bumetanide Infection, USP, Safety Data Sheet, 2012) (Year: 2012).*
Nielsen et al. (Int J of Pharmaceutics, 204, 2001, 35-41) (Year: 2001).*
"Clinical Study Report: Bioavailability of 2 mg Formulations for Nasal and Rectal Administration of Bumetanide," Leo Pharmaceutical Products, Medical Department (1998) (44 pages).
Extended European Search Report for European Application No. 20896035.1, dated Nov. 27, 2023 (10 pages).
Greene et al., "In-Hospital Therapy for Heart Failure With Reduced Ejection Fraction in the United States," JACC Heart Fail. 8(11): 943-953 (2020).
Hirako et al., "Impaired gastric motility and its relationship to gastrointestinal symptoms in patients with chronic renal failure," J Gastroenterol. 40(12):1116-22 (Dec. 2005).
International Preliminary Report on Patentability for International Patent Application No. PCT/US2020/063491, issued May 17, 2022 (6 pages).
International Search Report and Written Opinion for International Application No. PCT/US20/63491, mailed Mar. 12, 2021 (12 pages).
Kumar et al., "Nasal Gel Formulation: A Review," The Global Journal of Pharmaceutical Research 1(3):1-8 (Jul. 18, 2012).
Mahajan, "Overview of Diuretic Strategies in Edematous States," The Medicine Forum. 14(7):1-3 (2013).
MHRA, "Bumetanide 0.2mg/ml Oral Solution PL 17736/0132," 2012 (19 pages).
Nielsen et al., "Solubilization and Stability of Bumetanide in Vehicles for Intranasal Administration, a Pilot Study," Pharm Dev Technol. 6(2):145-149 (2001).
Pramanick et al., "Excipient selection in parenteral formulation development," Pharma Times. 45(3):65-77 (2013).

(Continued)

*Primary Examiner* — Umamaheswari Ramachandran
(74) *Attorney, Agent, or Firm* — Clark & Elbing LLP

(57) ABSTRACT

The present invention features methods and compositions for the intranasal, sublingual, and subcutaneous administration of bumetanide for the treatment of subjects suffering from edema refractory to oral diuretics.

10 Claims, 16 Drawing Sheets

(56)                    References Cited

OTHER PUBLICATIONS

Tilborg et al., "Pharmaceutical salts and cocrystals involving amino acids: a brief structural overview of the state-of-art," Eur J Med Chem. 74:411-26 (Mar. 3, 2014).

USP, Pharmacopeial Forum. vol. 27(6):3252 (2009).

Ward et al., "Bumetanide. A review of its pharmacodynamic and pharmacokinetic properties and therapeutic use," Drugs 28(5):426-64 (Nov. 1984).

\* cited by examiner

1

METHODS AND COMPOSITIONS FOR TREATING EDEMA REFRACTORY TO ORAL DIURETICS

FIELD OF THE INVENTION

The disclosure features methods and compositions for the treatment of edema refractory to oral diuretics.

BACKGROUND OF THE INVENTION

Congestive heart failure (CHF) is a common heart disease. The prevalence of incidents of congestive heart failure has recently increased, and there is considerable morbidity and mortality-associated with its diagnosis. In fact, congestive heart failure is an extremely lethal disease with an estimated five-year mortality for a vast majority of both men and women who encounter the disease. Congestive heart failure results from loss of, or impairment of, normal heart function. This loss or impairment reduces cardiac output. This, in turn, results in a reduction in both blood flow and blood pressure in the kidneys. This reduction in flow and pressure causes a renin-angiotensin response that exacerbates congestive heart failure. Blood volume is increased because angiotensin Il stimulates secretion of aldosterone from the adrenal cortex which, in turn, causes an increase in salt and water retention in the kidneys. The increase in blood volume and the corresponding vasoconstriction cause an increase in blood pressure and hence fluid overload on the heart which causes further deterioration of the heart condition.

To treat CHF, physicians put patients on a strict low sodium diet and their fluid intake is monitored. Some patients are limited to as little as one liter of fluid a day. The most important drugs in the physician's arsenal to combat fluid overload are the class of drugs called diuretics. Diuretics affect the kidney function in such a way that the reabsorption of fluid is suppressed. As a result, there is more urine output contrary to neurohormonal commands that the kidney is receiving. Physicians can treat the patient with agents that improve the pumping ability of the heart, increase blood pressure, and attempt to reactivate a more normal behavior of the body's control system. In general, this is effective in sustaining life of many heart failure patients. Nevertheless, in hundreds of thousands of patients, treatments with drugs and diet alone fail. When the patient is in an edematous state and is experiencing fluid overload, gastrointestinal absorption can be compromised, thus limiting the effectiveness of oral diuretics. As a result, the patient is often instructed to increase the dosage of oral diuretics putting further strain on the patient's kidneys. Eventually, oral diuretics become insufficient to remove excess fluid causing the patients to seek intravenous diuretics to bypass absorption by the gastrointestinal system. Consequently, the patients are often repeatedly admitted to the hospital for intensive care and administration of iv diuretics and are at risk (with each event) of over-diuresis once gastrointestinal absorption is restored. Ultimately, the over-diuresis can result in kidney failure. When available treatment can no longer achieve adequate fluid removal with existing kidney function, renal replacement therapies such as hemofiltration or dialysis have been increasingly used as a method of removing fluid in the acute CHF state. Acute heart failure can be treated with the Continuous Renal Replacement Therapy (a.k.a., an artificial kidney or dialysis machine) in the ICU of a hospital.

Therefore, there remains a need for treatment options for patients with heart failure in acute distress from fluid overload, such as to reduce the risk of hospitalizations and kidney failure.

SUMMARY OF THE INVENTION

The invention features compositions and methods for the treatment of edema refractory to oral diuretics.

In a first aspect, the invention features a pharmaceutical composition including (i) an aqueous solution having a pH of between about 5 and about 9 (e.g., a pH of 5±1, 6±1, 7±1, 8±1, or 9±1), (ii) between about 4 mg/ml and about 20 mg/mL (e.g., 4±1, 5±1, 6±1, 7±1, 8±1, 9±1, 10±1, 11±1, 12±1, 13±1, 14±1, 15±1, 16±1, 17±1, 18±1, 19±1, or 20±1 mg/mL) potassium bumetanide salt, and (iii) one or more pharmaceutically acceptable excipients.

In some embodiments, the pharmaceutical composition includes an aqueous solution having between about 5 mg/mL and about 10 mg/ml (e.g., 5±1, 6±1, 7±1, 8±1, 9±1, 10±1, 11±1, 11.5+1, 12±1, 13±1 or 14±1 mg/ml) of potassium bumetanide salt, one or more pharmaceutically acceptable excipients, and the aqueous solution has a pH of between about 6 and about 8 (e.g., pH 6+1,7±1,8±1)

In a related aspect the invention features a pharmaceutical composition including an aqueous solution of arginine bumetanide salt and one or more pharmaceutically acceptable excipients. The aqueous solution can include between about 4 mg/ml and about 15 mg/mL (e.g., 4 to 12, 5 to 10, 5±1, 6±1, 7±1, 8±1, 9±1, 10±1, 11±1, 11.5±1, 12±1, 13±1 or 14±1 mg/ml) of the arginine bumetanide salt, and the aqueous solution can have a pH of between about 5 and about 9 (e.g., a pH of 5 ±1, 6±1, 7±1, 8±1, or 9±1), and one or more pharmaceutically acceptable excipients.

In one embodiment of any of the above pharmaceutical compositions, the pharmaceutically acceptable excipients include a surfactant or a permeation enhancer. In some embodiments, the pharmaceutical composition includes a permeation enhancer present in an aqueous emulsion.

In another embodiment of any of the above aspects, the pharmaceutical composition is formulated for intranasal, sublingual, or subcutaneous administration.

In one embodiment of any of the above pharmaceutical compositions, the aqueous solution has a pH of between about 6 and about 8.

In some embodiments of any of the above pharmaceutical compositions, the one or more pharmaceutically acceptable excipients includes low viscosity sodium carboxymethyl cellulose, or a pharmaceutically acceptable salt thereof.

In other embodiments of any of the above pharmaceutical compositions, the one or more pharmaceutically acceptable excipients further includes (a) a viscosity enhancer; (b) a buffering agent; (c) a preservative; and/or (d) a tonicity agent.

The invention further features method of administering potassium salt of bumetanide to a subject transmucosally, wherein the potassium salt of bumetanide is administered intranasally or sublingually. In some embodiments, the potassium bumetanide is pharmaceutical composition of the invention. In other embodiments, the potassium salt of bumetanide is administered transmucosally for the treatment of edema. The invention further features a method of treating edema in a subject in need thereof, the method including administering to the subject an effective amount of a pharmaceutical composition of the invention. The administering can include delivering a dose volume of from 25 μl to 250 μl (e.g., 35±10, 50±10, 75±25, 125±25, 150±25, or 200±50

μl) of the pharmaceutical composition intranasally, sublingually, or subcutaneously to the subject. In particular embodiments, the dose is delivered not more than from 1 to 4 times over a six hour period. In certain embodiments, four doses of about 100 μL each are delivered over a period of 1 hour. In particular embodiments, two doses of about 100 μL each are delivered to a subject followed by two more does of about 100 μL each after a period of about 30 to 60 minutes. In other embodiments, the subject is suffering from edema refractory to oral diuretics. In certain embodiments, the subject has congestive heart failure. In particular embodiments, the subject is suffering from edema in the lung (e.g., pulmonary edema). In some embodiments, the pharmaceutical composition is administered intranasally to the subject in an outpatient setting. In certain embodiments, the pharmaceutical composition is self-administered.

The method can be of particular benefit where the subject has failed to achieve diuresis with oral diuretic therapy prior to the intranasally or sublingually administering. The subject to be treated may be experiencing swelling of the legs, shortness of breath, difficulty breathing, or chest pain unresolved with oral diuretic therapy prior to the intranasally or sublingually administering. In some embodiments, the subject is experiencing reduced intestinal motility prior to the intranasally or sublingually administering.

In a related aspect, the invention a method of treating edema refractory to oral diuretics in a subject with congestive heart failure, the method including administering to the subject an effective amount of a pharmaceutical composition including any one of the pharmaceutical compositions described herein. In some embodiments, the pharmaceutical composition is administered transmucosally (e.g., intranasally or sublingually). In particular embodiments, the pharmaceutical composition is administered intranasally or sublingually.

In particular embodiments, from 0.5 mg to 10 mg (e.g., 0.75±0.25, 1.0±0.5, 1.5±0.5, 2.5±0.5, 5.0±2.0, or 7.5±2.5 mg) of the bumetanide, or a pharmaceutically acceptable salt thereof, is delivered to the subject in not more than from 1 to 4 doses over a six hour period. In particular embodiments, the pharmaceutical composition includes (i) an aqueous solution having a pH of between about 5 and about 9 (e.g., a pH of 5±1, 6±1, 7±1, 8±1, or 9±1), (ii) between about 5 mg/ml and about 23 mg/ml (e.g., 5 ±1, 6±1, 7±1, 8±1, 9±1, 10±1, 11±1, 12±1, 13±1, 14±1, 15±1, 16±1, 17±1, 18±1, 19±1, or 20±3 mg/mL) of the bumetanide, or a pharmaceutically acceptable salt thereof, and (iii) one or more pharmaceutically acceptable excipients. In certain embodiments, the aqueous solution has a pH of between about 6 and about 8. In other embodiments, the one or more pharmaceutically acceptable excipients includes (a) a viscosity enhancer; (b) a buffering agent; (c) a preservative; (d) a surfactant; (e) a permeation enhancer; and/or (f) a tonicity agent. In some embodiments, the administering includes delivering a dose of from 25 μl to 250 μl (e.g., 35±10, 50±10, 75±25, 125±25, 150±25, or 200±50 μl) of the pharmaceutical composition intranasally to the subject. In certain embodiments, the administering includes delivering a dose of from 25 μl to 250 μl (e.g., 35±10, 50±10, 75±25, 125±25, 150±25, or 200±50 μl) of the pharmaceutical composition sublingually to the subject. In some embodiments, the administering includes delivering a dose of from 25 μl to 250 μl (e.g., 35±10, 50±10, 75±25, 125±25, 150±25, or 200±50 μl) of the pharmaceutical composition subcutaneously to the subject. The method can be of particular benefit where the subject has failed to achieve diuresis with oral diuretic therapy prior to the administering. The subject to be treated may be experiencing swelling of the legs, shortness of breath, difficulty breathing, or chest pain unresolved with oral diuretic therapy prior to the administering. In some embodiments, the subject is experiencing reduced intestinal motility prior to the administering.

In an embodiment of any of the above methods, the patient is upright during the administration and for at least 30 minutes, 1 hour, 2 hours, or 3 hours post-administration.

In an embodiment of any of the above methods, the patient is in a supine position during intranasal administration and for at least 2 minutes (e.g., at least 5 minutes, at least 30 minutes, or at least 1 hour) post-administration.

In an embodiment of any of the above methods, the subject has been treated with at least one dosage of an oral diuretic within the last 24 hours prior to the administering. The at least one oral diuretic can be selected from loop diuretics, such as bumetanide, furosemide or torsemide, or potassium-sparing diuretics, such as amiloride or spironolactone.

In some embodiments of any of the above methods, the patient does not receive more than a total of about 10 mg of the bumetanide salt over a 12 hour period. In some embodiments, the patient consults a physician having administered more than a total of 10 mg of the bumetanide salt over a 12 hour period.

In some embodiments of any of the above methods, the subject's risk of hospitalization due to complications associated with edema is reduced.

In an embodiment of any of the above methods, the pharmaceutical composition is administered in one, two, three or four doses over a 12 hour period. In some embodiments, the pharmaceutical composition is administered in a single dose. In some embodiments, the dosage over a 12 hour period from 1 to 2.5 mg of the bumetanide salt is administered in one, two, three, or four doses. In some embodiments, the dosage over a 12 hour period is from 2 to 5 mg of the bumetanide salt is administered in one, two, three or four doses. In some embodiments, the dosage over a 12 hour period is from 3 to 7.5 mg of bumetanide salt is administered in one, two, three or four doses. In some embodiments, the dosage over a 12 hour period is from 4 to 10 mg of bumetanide salt is administered in one, two, three or four doses.

In some embodiments of any of the above methods, the pharmaceutical composition is an aqueous composition having a pH of between about 5 and about 9 (e.g., a pH of 5±1, 6±1, 7±1, 8±1, or 9±1), and comprising between about 4 mg/ml and about 15.0 mg/ml (e.g., 4 to 12, 5 to 10, 5±1, 6 ±1, 7±1, 8±1, 9±1, 10±1, 11±1, 11.5±1, 12±1, 13±1 or 14±1 mg/mL) arginine bumetanide salt, and one or more acceptable excipients.

In some embodiments of any of the above methods, the pharmaceutical composition is an aqueous composition having a pH of between about 5 and about 9 (e.g., a pH of 5±1, 6±1, 7±1, 8±1, or 9±1), and comprising between about 4 mg/mL and about 20.0 mg/ml (e.g., 4 to 12, 5 to 10, 5±1, 6+1, 7±1, 8±1, 9±1, 10±1, 11±1, 11.5±1, 12±1, 13±1 or 14±1, 15±1, 16±1, 17±1, 18±1 or 19±1 mg/mL) bumetanide potassium salt, and one or more acceptable excipients.

In some embodiments of any of the above methods, the pharmaceutical composition is an aqueous composition having a pH of between about 6 and about 8 (e.g., a pH of 6±1, 7±1, 8±1 and comprising between about 5 mg/ml and about 10 mg/ml (e.g., 5±1, 6±1, 7±1, 8±1, 9±1, 10±1) potassium bumetanide salt, and one or more pharmaceutically acceptable excipients.

In a related aspect, the invention features a method of treating edema in a subject with congestive heart failure, the method including subcutaneously administering to the subject a dose of from 100 µl to 300 µl (e.g., 125±25, 150±50, 175±50, 200±25, 250±50, or 275±25 µl) of an aqueous emulsion having a pH of between about 5 and about 9 (e.g., a pH of 5±1, 6±1, 7±1, 8±1, or 9±1), and comprising between about 7.0 mg/ml and about 15.0 mg/ml (e.g., 8±1, 9±1, 10±1, 11±1, 12±1, 13±1 or 14±1 mg/mL) arginine bumetanide salt. In particular embodiments, the aqueous emulsion includes medium chain glycerides (MCT), lecithin (E80), polysorbate surfactants and/or polyglycolized glycerides. In some embodiments, the formulation provides an extended release of bumetanide such that not more than 2 doses are administered to the subject over a 48 hour period or not more than 1 dose is administered to the subject over a 72 hour period.

In certain embodiments of any of the above methods, the pharmaceutical composition includes a surfactant, a permeation enhancer, a buffering agent, a preservative, a viscosity enhancer, or a tonicity agent (e.g., any surfactant, permeation enhancer, buffering agent, preservative, viscosity enhancer, or tonicity agent described herein). In particular embodiments, the pharmaceutical composition includes a surfactant selected from glycerides, alkyl saccharides, ester saccharides, polyglycolized glycerides, and polysorbate surfactants (e.g., any glyceride, alkyl saccharide, ester saccharide, polyglycolized glyceride, or polysorbate surfactant described herein).

In some embodiments of any of the above methods where the pharmaceutical composition is formulated for intranasal administration, the pharmaceutical composition is administered intranasally and the pharmaceutical composition includes a permeation enhancer.

In some embodiments of any of the above methods where the pharmaceutical composition is formulated for sublingual administration, the pharmaceutical composition is administered sublingually, and the pharmaceutical composition optionally includes a permeation enhancer. In some embodiments of any of the above methods, the pharmaceutical composition includes an emulsion (e.g., a nanoemulsion). The emulsion can include medium chain glycerides (MCT), lecithin (E80), polysorbate surfactants, and/or polyglycolized glycerides. In particular embodiments, the emulsion is a nanoemulsion including soy lecithin and glycocholic acid. In some embodiments, the pharmaceutical composition of any of the above methods is free from any emulsions. In certain embodiments, the pharmaceutical composition is free from any surfactant. In some embodiments, the pharmaceutical composition is free from any permeation enhancer. In certain embodiments, the pharmaceutical composition is free from any buffer.

In some embodiments of any of the above methods, the subject is a mammal. In certain embodiments, the subject is a dog. In particular embodiments, the subject is a human.

In one embodiment of any of the above aspects, the pharmaceutical composition includes about 0.5 to 2 percent bumetanide (wt/wt), about 0.1 percent sodium carboxymethyl cellulose (low viscosity) (wt/wt), about 0.5 percent benzyl alcohol (wt/wt), about 0.078 to 0.31 percent potassium (e.g., the potassium ion) (wt/wt) and about 2 to 4 percent mannitol (wt/wt) with a concentration between 5 mg/ml and 20 mg/ml and a pH in solution between about 6 and about 8 in water.

In another embodiment of any of the above aspects, the pharmaceutical composition includes about 0.5 to 1.5 percent bumetanide (wt/wt), about 0.1 percent sodium carboxymethyl cellulose (low viscosity) (wt/wt), about 0.5 percent benzyl alcohol (wt/wt), about 0.45 to 1.35 percent L-arginine (wt/wt), and about 2-4.0 percent mannitol (wt/wt) with an arginine salt of bumetanide concentration between 5 mg/mL and 15 mg/mL and a pH in solution between about 6 and about 8 in water.

In another aspect, the invention features a solid including arginine bumetanide salt.

US 12,558,330 B2

7 bumetanide salt formulation (F69), the potassium bumetanide salt formulation (F70), the bumetanide emulsion (FE-9), and the bumetanide nano-emulsion (FNE-1) on a logarithmic scale.

Figure 10:
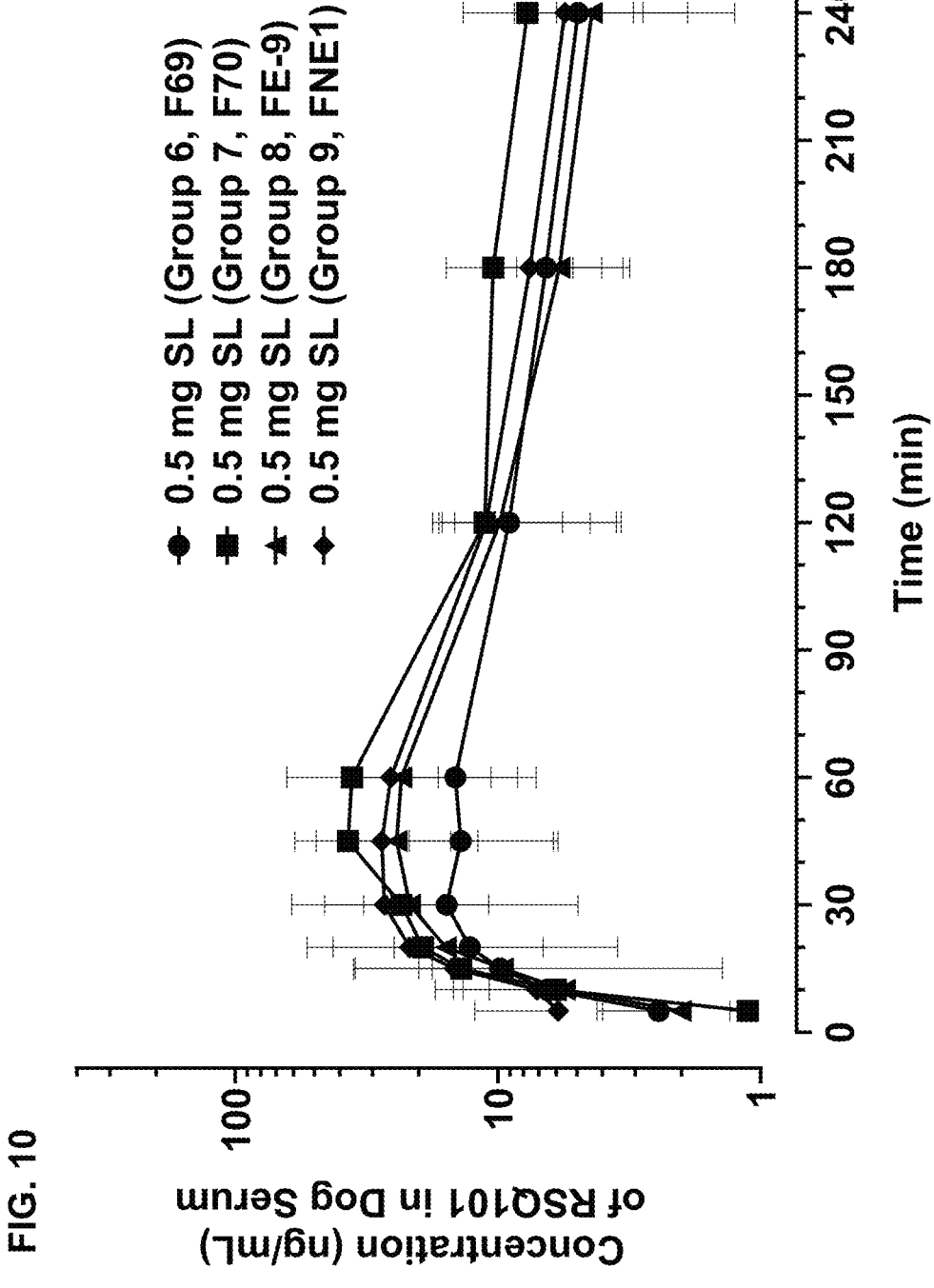

FIG. 10 is a graph showing the concentration (ng/mL) of bumetanide in the serum of dogs over a period of 2 minutes to 240 minutes after sublingual (SL) administration of 0.5 mg of a bumetanide compound including the arginine bumetanide salt formulation (F69), the potassium bumetanide salt formulation (F70), the bumetanide emulsion (FE-9), and the bumetanide nano-emulsion (FNE-1) on a logarithmic scale.

Figure 11:
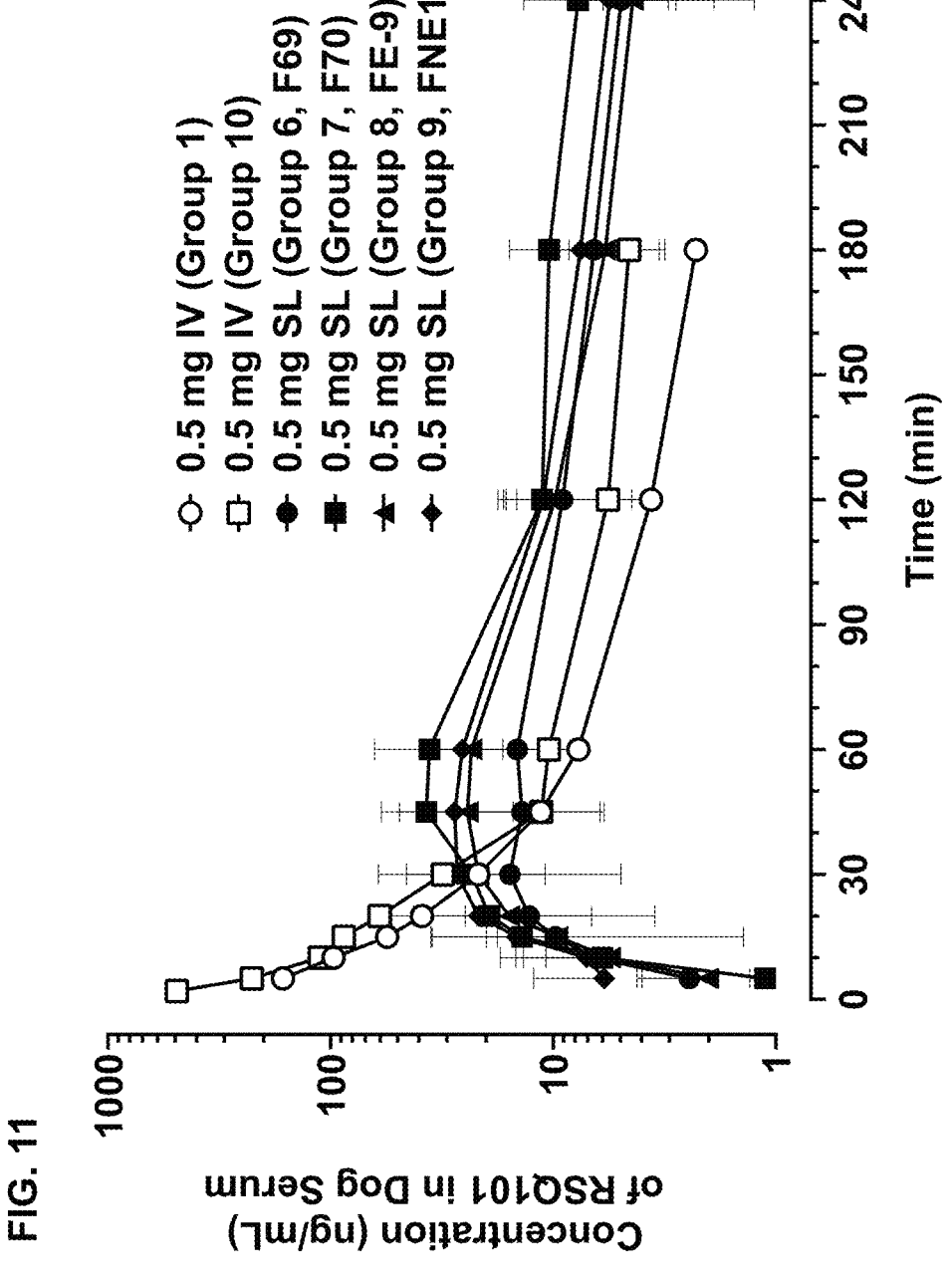

FIG. 11 is a graph showing the concentration (ng/ml) of bumetanide in the serum of dogs over a period of 2 minutes to 240 minutes after IV administration of 0.5 mg of commercially available bumetanide or sublingual administration (SL) of 0.5 mg of a bumetanide compound including the arginine bumetanide salt formulation (F69), the potassium bumetanide salt formulation (F70), the bumetanide emulsion (FE-9), and the bumetanide nano-emulsion (FNE-1) on a logarithmic scale.

Figure 12:
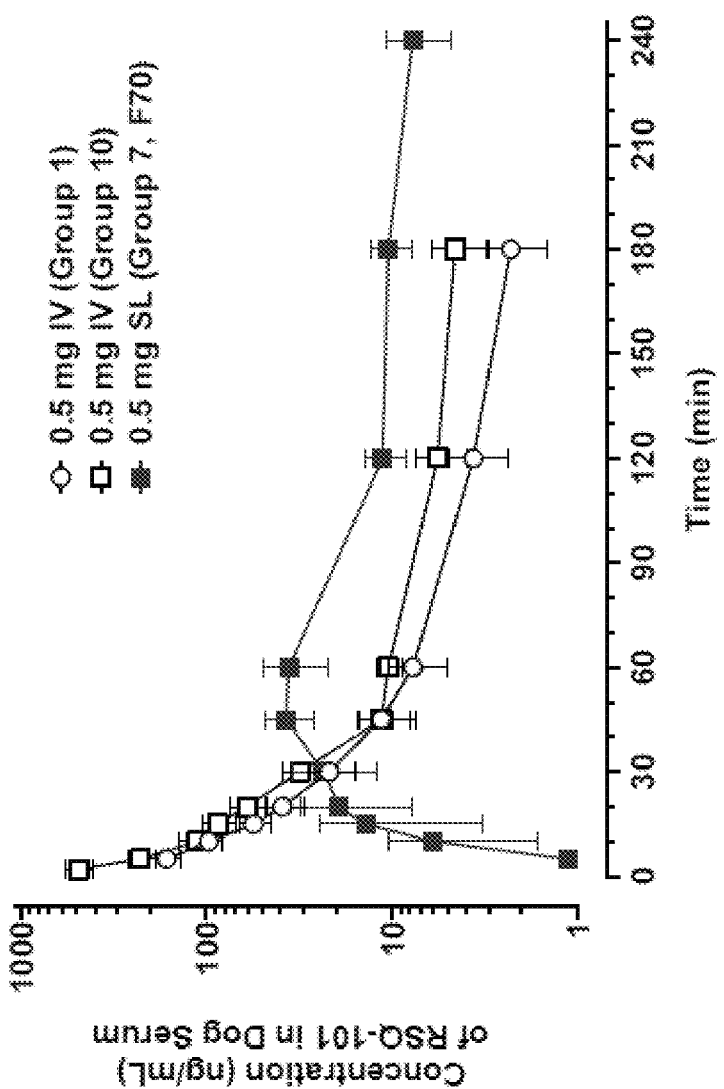

FIG. 12 is a graph showing the concentration (ng/ml) of bumetanide in the serum of dogs over a period of 2 minutes to 240 minutes after IV administration of 0.5 mg of commercially available bumetanide versus the concentration of bumetanide achieved with sublingual administration of potassium bumetanide (F70) on a logarithmic scale.

Figure 13:
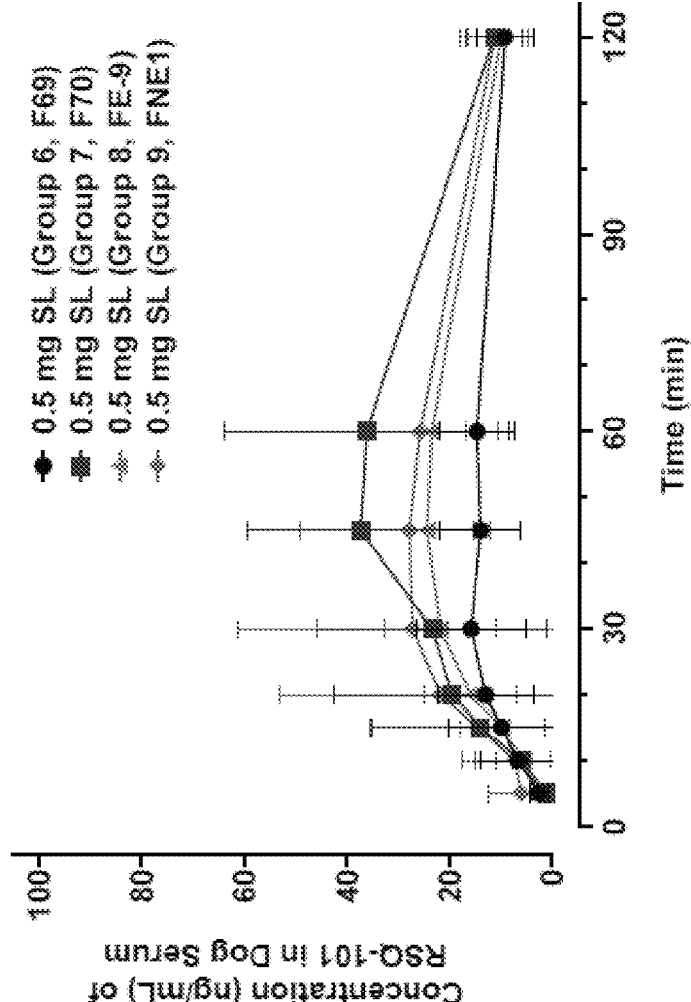

FIG. 13 is a graph showing the concentration (ng/ml) of bumetanide in the serum of dogs over a period of 2 minutes to 120 minutes SL administration of 0.5 mg of the F69, F70, FE-9, or the FNE-1 bumetanide compound on a linear scale.

Figure 14:
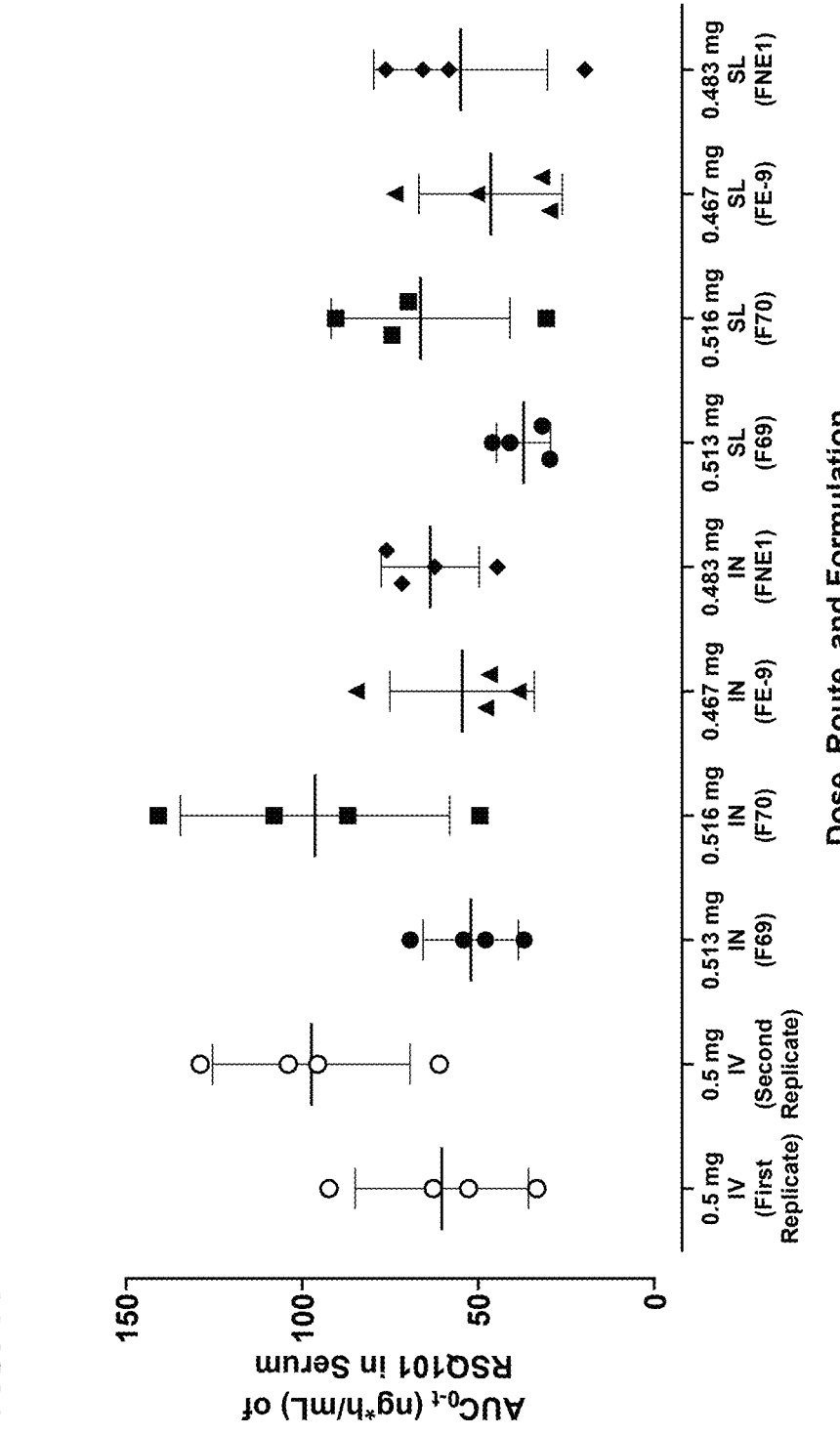

FIG. 14 is a graph showing the area under the curve (AUC) of the concentration of bumetanide in the serum of dogs over a time period of 2 to 240 minutes (ng*h/mL) after IV administration of 0.5 mg of commercially available bumetanide, or IN or SL administration of 0.5 mg of the F69, F70, FE-9, or the FNE-1 bumetanide formulations.

Figure 15:
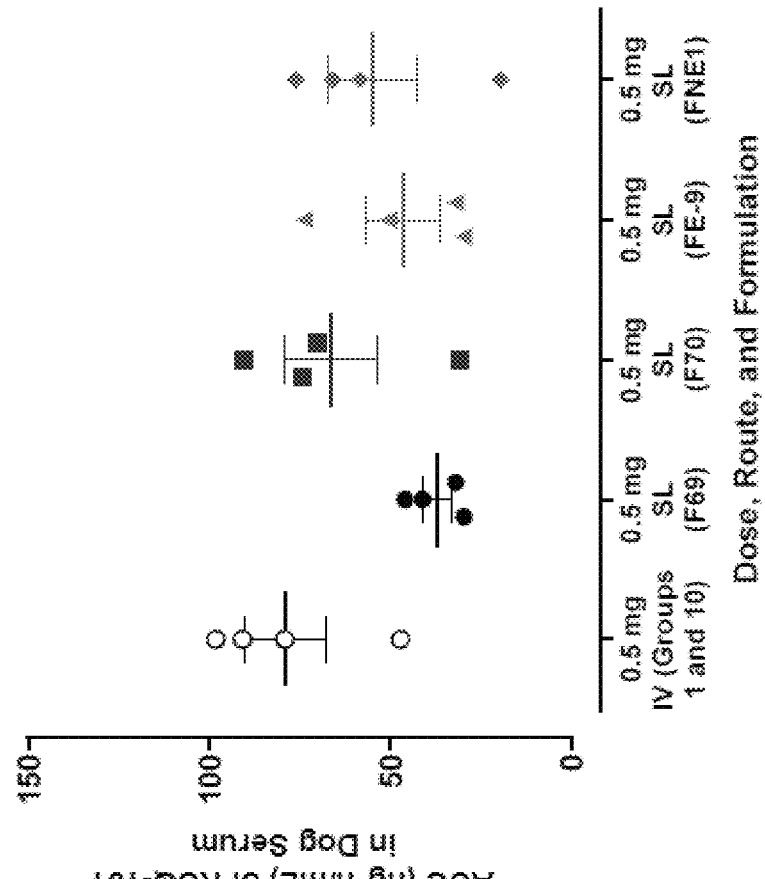

FIG. 15 is a graph showing the area under the curve (AUC) of the concentration of bumetanide in the serum of dogs over a time period of 2 to 240 minutes (ng*h/mL) after IV administration of 0.5 mg of commercially available bumetanide or SL administration of 0.5 mg of the F69, F70, FE-9, or the FNE-1 bumetanide formulations.

Figure 16:
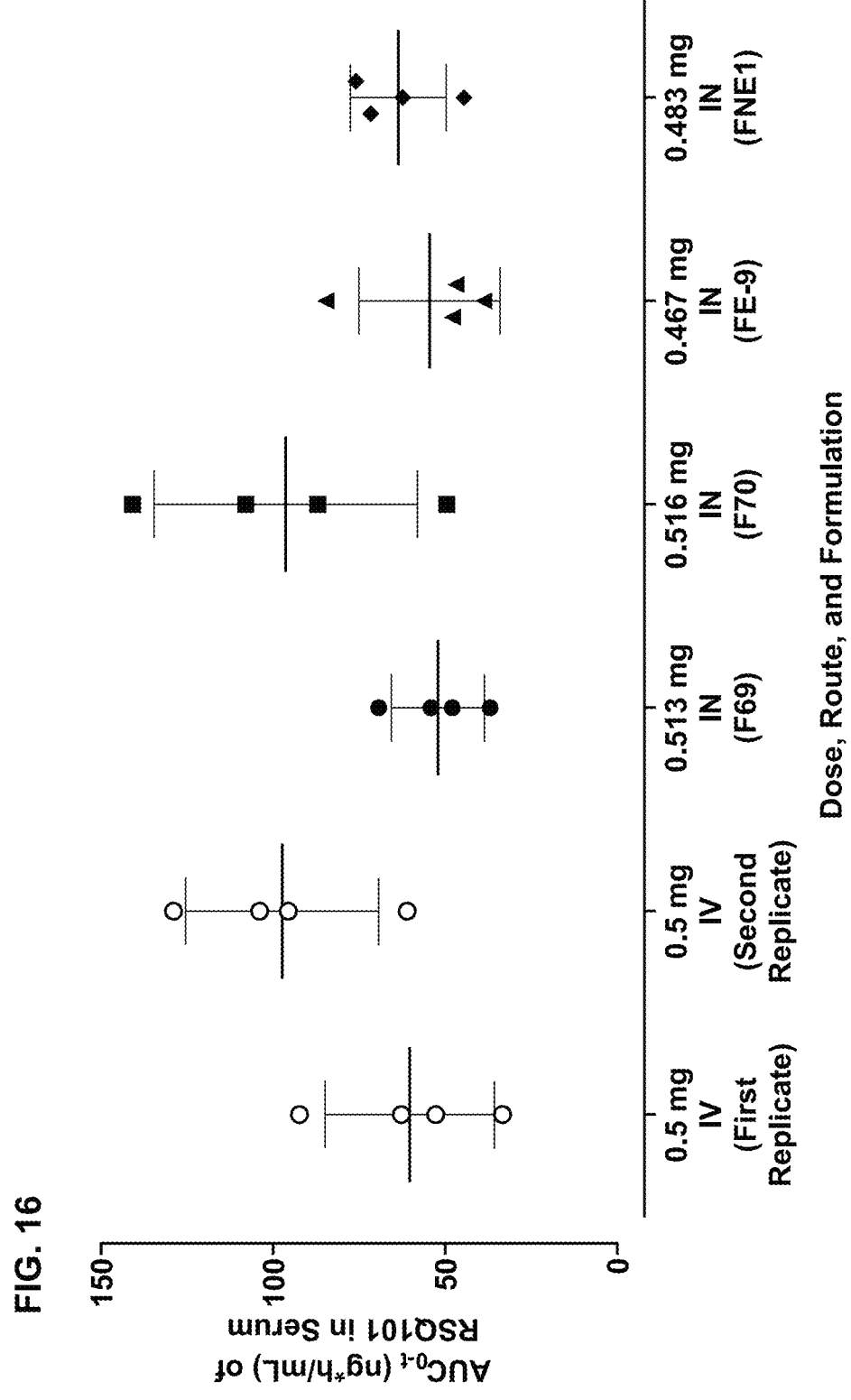

FIG. 16 is a graph showing the area under the curve (AUC) of the concentration of bumetanide in the serum of dogs over a time period of 2 to 240 minutes (ng*h/mL) after IV administration of 0.5 mg of commercially available bumetanide or IN administration of 0.5 mg of the F69, F70, FE-9, or the FNE-1 bumetanide formulations.

Definitions

As used herein, the term "about" refers to a value that is within 10% above or below the value being described. For instance, the phrase "about 6 mg/mL" refers to a value between 5.4 and 6.6 mg/mL.

As used herein, the term "effective amount," refers to a quantity of a pharmaceutical composition sufficient to, when administered to the subject, for example a human subject, effect beneficial or desired results, such as clinical results. For example, in the context of edema, described herein, this term refers to an amount of the composition sufficient to achieve a reduction in the symptoms of edema as compared to the response obtained without administration of the composition. The quantity of a given composition described herein that will correspond to such an amount depending upon various factors, such as the given agent, the pharmaceutical formulation, the route of administration, the identity of the subject (e.g., age, sex, weight) being treated, and the like.

As used herein, "emulsion" is meant a two-phase colloidal system, such as a mixture of two or more immiscible liquids, which can be added to a pharmaceutical composition as an excipient. Liquid emulsions are those in which both the dispersed and the continuous phases are liquid. Energy input through shaking, stirring, homogenizing, or spray processes are typically needed to form an emulsion. For example, the emulsion can include an aqueous phase and a nonaqueous phase, and can include a self emulsifying system, or the emulsion can be nano-particulate containing an aqueous phase and a nonaqueous phase (e.g., a nanoemulsion or microemulsion). By "nanoemulsion or microemulsion" is meant a clear, stable, isotropic liquid mixture of oil, water, and surfactant, optionally in combination with a cosurfactant. The aqueous phase may contain salt(s) and/or other ingredients in addition to a biologically active agent. In contrast to ordinary emulsions, microemulsions form upon simple mixing of the components and do not require the high shear conditions generally used in the formation of ordinary emulsions. The two basic types of microemulsions are direct (oil dispersed in water, o/w) and reversed (water dispersed in oil, w/o).

As used herein, the terms "edema in the lung" or "pulmonary edema" refer to a condition where the patient has excess fluid in the lungs, which results in difficulty breathing. Edema in lungs may be caused by conditions related to heart failure, pneumonia, trauma, an allergic reaction, or another cause.

As used herein, the term "edema refractory to oral diuretics" refers to edema that is not responsive to oral diuretic treatment, such that diuresis is not achieved and excessive bodily fluid persists despite treatment with oral diuretics, thus resulting in persistence of the edematous state.

As used herein, the term "failed to achieve diuresis" refers to a patient's lack of increased voiding of bodily fluid and consequent persistence of an edematous state despite administration of oral diuretics.

As used herein, the term "intranasal" or "intranasally" refers to a method of administration of a pharmaceutical composition wherein the composition is delivered by way of the nasal cavity.

As used herein, the term "loop diuretic" means a drug used in patients with congestive heart failure or renal insufficiency to reduce symptoms of hypertension and edema. A loop diuretic belongs to a class of diuretic agents that reduce reabsorption of sodium and chloride by the kidney leading in an increased secretion of urine.

As used herein, the term "low viscosity sodium carboxymethyl cellulose" or "low viscosity sodium CMC" refers to sodium carboxymethyl cellulose which has a viscosity of between 30 cP and 45 cP (e.g., 30±1 cP, 31±1 cP, 32±1 cP, 33±1 cP, 34±1 cP, 35±1 cP, 36±1 cP, 37±1 cP, 38±1 cP, 39±1 cP, 40±1 cP, 41±1 cP, 42±1 cP, 43±1 cP, 44±1 cP, and 45±1 cP) in 2% aqueous solution at 25° C. or between 50-200 cP in 4% aqueous solution at 25° C. Low viscosity sodium carboxymethyl cellulose can have a molecular weight of approximately 90 kDa.

As used herein, the term "pharmaceutically acceptable" refers to those compounds, materials, compositions and/or dosage forms, which are suitable for contact with the tissues of a subject, such as a mammal (e.g., a human) without excessive toxicity, irritation, allergic response, and other problem complications commensurate with a reasonable benefit/risk ratio.

As used herein, the term "pharmaceutically acceptable salt," represents those salts which are suitable for use in the treatment of humans without undue toxicity. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use,* (Eds. P. H. Stahl and C. G. Wermuth), Wiley-VCH, 2008. The salts can be prepared, for example, in situ during the final isolation and purification of the compounds described herein or separately by reacting the free base group with a suitable organic acid. Representative acid addition salts include, without limitation, acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include, without limitation, sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, L-a-phosphatidylethanolamine, bis(2-ethylhexyl)amine, soy Lecithin and the like. Representative amino acid salts include lysine, arginine, glycine, histidine, and the like. One of skill in the art will recognize that any mention of a drug compound includes within its scope the pharmaceutically acceptable salts of the indicated drug compound.

As used herein, the term "potassium-sparing diuretics" refers to a kind of diuretic drug that does not promote the secretion of potassium into urine, thus increasing fluid voiding. These diuretics can be used alone or in conjunction with loop or thiazide diuretics.

As used herein, the term "reduced intestinal motility" refers to a slowing of the activity of the gastrointestinal tract in a subject. One effect of the slowed activity can be reduced absorption, thus preventing effective absorption of pharmaceutical compositions. For example, this reduced intestinal motility can be caused by edema (e.g., such as fluid overload resulting from congestive heart failure) and prevents adequate absorption of the oral diuretics necessary for the treatment of the edema.

As used herein, the term "risk of hospitalization" refers to the potential likelihood that a patient is hospitalized for the treatment of edema, instead of effectively treating the edema without hospitalization by self-administering bumetanide using a method of the invention. A reduced risk of hospitalization is assessed for a given diseased population (e.g., patients suffering from congestive heart failure) of a particular severity comparing hospitalization rates for the treatment of edema in patients self-administering bumetanide to patients relying solely upon oral diuretics to treat the edema. Using the bumetanide methods of the invention, the hospitalization rates for the treatment of edema in a population of patients can be reduced by at least 10%, 20%, 30%, or 50%, and so the risk of hospitalization in individual patients using bumetanide can be reduced.

As used herein, the terms "sublingual" and "sublingually" refer to a method of administration of a pharmaceutical composition wherein the composition is delivered under the tongue, and the pharmaceutical composition diffuses into the blood through tissues under the tongue including the mucous gland.

As used herein, the term "supine" when used in reference to the positioning of the patient during treatment refers to the patient maintaining a prostrate position during administration of the pharmaceutical composition, and/or for a period of time post-administration. If the patient is unable to lie prostrate, the patient may recline or have their head facing up.

As used herein, "treatment" and "treating" refer to therapy for a subject in need of diuresis, such as therapy to ameliorate one or more symptoms of edema in a subject suffering from edema, or prophylactically reducing the risk of one or more symptoms of edema in a subject at risk of from edema.

As used herein, the term "unit dose" or "dosage" when used in reference to a therapeutic composition refers to physically discrete units suitable as unitary dosage for the subject, each unit containing a predetermined quantity of active material calculated to produce the desired therapeutic effect in association with the required diluent, i.e., carrier, or vehicle.

As used herein, the term "upright" when used in reference to the positioning of the patient during treatment refers to the patient maintaining a vertical posture of their torso and/or entire body. Specifically, the patient is not lying down prostrate during administration of the pharmaceutical composition, and/or for a period of time post-administration.

DETAILED DESCRIPTION

The invention features pharmaceutical compositions and methods for the treatment of edema refractory to oral diuretics. Bumetanide can be formulated for intranasal, sublingual, or subcutaneous delivery in salt forms that permit therapeutically effective amounts of bumetanide to be delivered in small volumes (about 100-150 L) particularly suitable for intranasal delivery. It is optimal for the concentration of the bumetanide to by 5 mg/ml or 10 mg/mL such that an ideal dosage can be achieved in this small volume. Concentrations of the bumetanide salt in solution approach their limit of saturation as changes in solubility occurring as a result of change in temperature and storage conditions need to be considered to ensure suitable shelf-life stability of the pharmaceutical. This further emphasizes the need addressed by this invention for salt forms capable of stability at least 5 mg/mL.

With these concentrations of bumetanide salts, intranasal, sublingual, or subcutaneous administration of bumetanide to patients who are experiencing edema refractory to oral diuretics due to their edematous state (e.g., an occurrence found in patients suffering from edema related reduced intestinal motility) can relieve the edema and restore the effectiveness of orally administered diuretics without the need for hospitalization. Subjects may be able to self-administer the pharmaceutical composition based on their symptoms, therefore, preventing the need for hospitalization, or the pharmaceutical composition may be administered by a medical professional (e.g., medical doctor, emergency responder or nurse) when a subject is experiencing acute distress.

Furthermore, the methods of the invention can reduce the risk of kidney failure in certain patients, such as those suffering from congestive heart failure. When such patients are in an edematous state and experiencing fluid overload, gastrointestinal absorption can be compromised, thus limiting the effectiveness of oral diuretics. As a result, the patient is often instructed to increase the dosage of oral diuretics putting further strain on the patient's kidneys. Eventually, oral diuretics become insufficient to remove excess fluid causing the patients to be hospitalized to receive intravenous diuretics to bypass the gastrointestinal system. Consequently, the patients are at risk of over-diuresis once gastrointestinal absorption is restored. This over-diuresis can result in kidney failure.

Pharmaceutical Compositions

The bumetanide formulations of the invention can be solutions, suspensions, or emulsions. The formulations can include surfactants, antioxidants, pH adjusting agents (e.g., an acid or a base), buffering agents, preservatives, tonicity agents, viscosity enhancers (e.g., carboxymethylcellulose), surfactants, and/or permeation enhancing agents. The formulations may be administered as an aqueous solution on in the form of an emulsion, including nanoemulsions and microemulsions. The formulations may be provided in a single or multidose form. The formulation may be administered subcutaneously, sublingually, or intranasally. In the case of a dropper or pipette, dosing may be achieved by the subject administering an appropriate, predetermined volume of the solution. In the case of a spray, this may be achieved, for example, by means of a metering atomizing spray pump. The metered spray pump may be a single metered spray pump device (e.g., APTAR® Unidose, Unidose®Xtra) or may be a multi-dose metered pump device (e.g., APTAR® Bidose (BDS), MK® pump).

Emulsions

Emulsions can be obtained by adding an emulsifier and purified water to an active ingredient; emulsifying them by an appropriate method to uniformize the components. That is, the components of the emulsion preferably include, but are not limited to, at least an active ingredient, solvent, emulsifier, buffering agent, and isotonicity agent. Examples of emulsifying agents that can be used in the formulations of the invention include carboxyvinyl polymer, carmellose sodium, highly purified yolk lecithin, glycerin, hydrogenated soy-bean phospholipid, squalane, squalene, polyoxyl 45 stearate, stearic acid, polyoxyl 55 stearate, purified soybean lecithin, purified yolk lecithin, sorbitan sesquioleate, sorbitan esters of fatty acid, soy-bean lecithin, hydroxypropyl cellulose, partially hydrogenated soy-bean phospholipid, propylene glycol, polyoxyethylene hydrogenated castor oil, polyoxyethylene hydrogenated castor oil 5, polyoxyethylene hydrogenated castor oil 10, polyoxyethylene hydrogenated castor oil 20, polyoxyethylene hydrogenated castor oil 40, polyoxyethylene hydrogenated castor oil 50, polyoxyethylene hydrogenated castor oil 60, polyoxyethylene castor oil, polyoxyethylene behenyl ether, polyoxyethylene (160) polyoxypropylene (30)glycol, polyoxyethylene (1) polyoxypropylene (1) cetyl ether, polyoxyethylene (1 0) polyoxypropylene (4) cetyl ether, polyoxyethylene (20) polyoxypropylene (4) cetyl ether, polyoxyethylene (20) polyoxypropylene (8) cetyl ether, polysorbate 80, macrogol 400, cottonseed oil-soy-bean oil mixture, and sorbitan monostearate. Preferable examples include highly purified yolk lecithin, hydrogenated soy-bean phospholipid, squalane, squalene, polyoxyl 45 stearate, polyoxyl 55 stearate, purified soy-bean lecithin, purified yolk lecithin, sorbitan sesquioleate, sorbitan esters of fatty acid, soy-bean lecithin, partially hydrogenated soy-bean phospholipid, polyoxyethylene hydrogenated castor oil, polyoxyethylene hydrogenated castor oil 5, polyoxyethylene hydrogenated castor oil 10, polyoxyethylene hydrogenated castor oil 20, polyoxyethylene hydrogenated castor oil 40, polyoxyethylene hydrogenated castor oil 50, polyoxyethylene hydrogenated castor oil 60, polyoxyethylene castor oil, polyoxyethylene behenyl ether, polyoxyethylene (160) polyoxypropylene (30) 15 glycol, polyoxyethylene (1) polyoxypropylene (1) cetyl ether, polyoxyethylene (10) polyoxypropylene (4) cetyl ether, polyoxyethylene (20) polyoxypropylene (4) cetyl ether, polyoxyethylene (20) polyoxypropylene (8) cetyl ether, and sorbitan monostearate. Preferred emulsifiers include poloxamers (e.g., low molecular weight poloxamers (e.g., poloxamers having an average molecular weight of less than 10 kDa, e.g., poloxamer 188), polysorbates (e.g. Polysorbate 80 and Polysorbate 20), polyoxyethylene alkyl ethers (Brij), alkylphenylpolyoxyethylene ethers (Triton-X), sodium dodecyl sulphate (SDS), medium chain triglycerides (MCT), glycolic acid, polyvinylpyrrolidone (PVP), 1,2-propylene glycol, cremophor EL, cremophor RH40, lecithin (E-80), soy lecithin (PL90G), tert-butanol, ethanol, or polyoxyethylene stearate. Preferred emulsifiers are polysorbates, lecithin, MCT and glycolic acid. For example, polysorbate 80 may be used in intranasal pharmaceutical compositions (e.g., solutions) at concentrations, e.g., 1% (w/w) to 15% (w/W (e.g., 1% (w/w) to 15% (w/w), 1% (w/w) to 10% (w/w), 1% (w/w) to 5% (w/w), 2% (w/w) to 5% (w/W), 2% (w/w) to 10% (w/w), 2% (w/w) to 15% (w/w), 3% (w/w) to 5% (w/w), 3% (w/w) to 10% (w/w), 3% (w/w) to 15% (w/w), 4% (w/w) to 5% (w/w), 4% (w/w) to 10% (w/w), 4% (w/w) to 15% (w/w), 5% (w/w) to 10% (w/w), 5% (w/w) to 15% (w/w). 0.003% (w/v) to 0.1% (w/v), 0.1% (w/v) to 5% (w/v), 0.1% (w/v) to 4% (w/v), 0.1% (w/v) to 3% (w/V), Surfactants In some embodiments of the pharmaceutical composition, a surfactant may be added and may be cationic, anionic, non-ionic or Zwitterionic. A surfactant may be added to the composition to increase the solubility of bumetanide. Surfactants that can be useful in the formulations of the invention include, without limitation, tetradecyl-B-D-maltoside, soy lecithin, distearoyl glycerol-3-phosphatidylamine, L-α-phosphatidylethanolamine and bis(2-ethylhexyl)amine. Examples of surfactants that can be used in the pharmaceutical compositions of the invention include, without limitation, glycerides, alkyl saccharides, ester saccharides, polyglycolized glycerides, soy lecithin, lecithin (E80), and polysorbate surfactants.

Glycerides

Glycerides can be used in the pharmaceutical compositions of the invention. Glycerides are fatty acid mono-, di-, and tri-esters of glycerol. Glycerides include saturated and unsaturated monoglycerides, diglycerides (1,2- and 1,3-diglycerides), and triglycerides, with mixed and unmixed fatty acid composition. Each glyceride is herein designated as (Cn: m), where n is the length of the fatty acid side chain and m is the number of double bonds (cis- or trans-) in the fatty acid side chain. Examples of commercially available monoglycerides include: monocaprylin (C8; i.e., glyceryl monocaprylate) (Larodan), monocaprin (C10; i.e., glyceryl monocaprate) (Larodan), monolaurin (C12; i.e., glyceryl monolaurate) (Larodan), monopalmitolein (C16:1) (Larodan), glyceryl monomyristate (C14) (Nikkol® MGM, Nikko), glyceryl monooleate (C18:1) (PECEOL®, Gattefosse), glyceryl monooleate (Myverol®, Eastman), glycerol monooleate/linoleate (OLICINE®, Gattefosse), glycerol monolinoleate (Maisine, Gattefosse), and monoelaidin (C18:1) (Larodan). Examples commercially available mono/di and tri glycerides include Capmul MCM C8EP, (C8:C10 mono/di glycerides) and Capmul MCM C10 (mono/di glycerides). Examples commercially available diglycerides include: glyceryl laurate (Imwitor® 312, Huls), glyceryl caprylate/caprate (Capmul® MCM, ABITEC), caprylic acid diglycerides (Imwitor® 988, Huls), caprylic/capric glycerides (Imwitor® 742, Huls), dicaprylin (C8) (Larodan), dicaprin (C10) (Larodan), dilaurin (C12) (Larodan), glyceryl dilaurate (C12) (Capmul® GDL, ABITEC®). Examples commercially available triglycerides include: tricaprylin (C8; i.e., glyceryl tricaprylate) (Larodan), capatex 100 (C10), tricaprin (C10; i.e., glyceryl tricaprate) (Larodan), trilaurin (C12; i.e., glyceryl trilaurate) (Larodan), dimyristin (C14) (Larodan), dipalmitin (C16) (Larodan), distearin (Larodan), glyceryl dilaurate (C12) (Capmul® GDL, ABITEC), glyceryl dioleate (Capmul® GDO, ABITEC®), glycerol esters of fatty acids (GELUCIRER 39/01, Gattefosse), dipalmitolein (C16:1) (Larodan), 1,2 and 1,3-diolein (C18:1) (Larodan), dielaidin (C18:1) (Larodan), and dilinolein (C18:2) (Larodan).

Polyglycolized Glycerides

Polyglycolized glycerides can be used in the pharmaceutical compositions of the invention. Polyglycolized glycerides include polyethylene glycol glyceride monoesters, polyethylene glycol glyceride diesters, polyethylene glycol glyceride triesters, and mixtures thereof containing a variable amount of free polyethylene glycol, such as a polyethylene glycol-oil transesterification product. The polyglycolized glyceride can include either monodisperse (i.e., single molecular weight) or polydisperse polyethylene glycol moieties of a predetermined size or size range (e.g., PEG2 to PEG 40). Polyethylene glycol glycerides include, for example: PEG glyceryl caprate, PEG glyceryl caprylate, PEG-20 glyceryl laurate (Tagat® L, Goldschmidt), PEG-30 glyceryl laurate (Tagat® L2, Goldschmidt), PEG-15 glyceryl laurate (Glycerox L series, Croda), PEG-40 glyceryl laurate (Glycerox L series, Croda), PEG-20 glyceryl stearate (Capmul® EMG, ABITEC), and Aldo® MS-20 KFG, Lonza), PEG-20 glyceryl oleate (Tagat®) O, Goldschmidt), and PEG-30 glyceryl oleate (Tagat® O2, Goldschmidt). Caprylocapryl PEG glycerides include, for example, caprylic/capric PEG-8 glyceride (Labrasol®, Gattefosse), caprylic/capric PEG-4 glyceride (Labrafac® Hydro, Gattefosse), and caprylic/capric PEG-6 glyceride (SOFTIGEN@767, Huls). Oleoyl PEG glyceride include, for example oleoyl PEG-6 glyceride, (Labrafil® M1944 CS, Gattefosse). Lauroyl PEG glycerides includes, for example, lauroyl PEG-32 glyceride (Gelucire® ELUCIRE 44/14, Gattefosse). Stearoyl PEG glycerides include, for example stearoyl PEG-32 glyceride (Gelucire® 50/13, Gelucire® 53/10, Gattefosse). PEG castor oils include PEG-3 castor oil (Nikkol® CO-3, Nikko), PEG-5, 9, and 16 castor oil (AC-CONON® CA series, ABITEC), PEG-20 castor oil, (Emalex® C-20, Nihon Emulsion), PEG-23 castor oil (Emulgante® EL23), PEG-30 castor oil (Incrocas® 30, Croda), PEG-35 castor oil (Incrocas-35®, Croda), PEG-38 castor oil (Emulgante® EL 65, Condea), PEG-40 castor oil (Emalex® C-40, Nihon Emulsion), PEG-50 castor oil (Emalex® C-50, Nihon Emulsion), PEG-56 castor oil (Eumulgin® PRT 56, Pulcra SA), PEG-60 castor oil (Nikkol® CO-60TX, Nikko), PEG-100 castor oil, PEG-200 castor oil (Eumulgin® PRT 200, Pulcra SA), PEG-5 hydrogenated castor oil (Nikkol® HCO-5, Nikko), PEG-7 hydrogenated castor oil (Cremophor® WO7, BASF), PEG-10 hydrogenated castor oil (Nikkol HCO-10, Nikko), PEG-20 hydrogenated castor oil (Nikkol® HCO-20, Nikko), PEG-25 hydrogenated castor oil (Simulsol® 1292, Seppic), PEG-30 hydrogenated castor oil (Nikkol® HCO-30, Nikko), PEG-40 hydrogenated castor oil (Cremophor® RH 40, BASF), PEG-45 hydrogenated castor oil (Cerex ELS 450, Auschem Spa), PEG-50 hydrogenated castor oil (Emalex® HC-50, Nihon Emulsion), PEG-60 hydrogenated castor oil (Nikkol® HCO-60, Nikko), PEG-80 hydrogenated castor oil (Nikkol® HCO-80, Nikko), and PEG-100 hydrogenated castor oil (Nikkol® HCO-100, Nikko). Additional polyethylene glycol-oil transesterification products include, for example, stearoyl PEG glyceride (Gelucire® 50/13, Gattefosse). The polyglycolized glycerides useful in the formulations of the invention can include polyethylene glycol glyceride monoesters, diesters, and/or triesters of acetic, propionic, butyric, valeric, hexanoic, heptanoic, caprylic, nonanoic, capric, lauric, myristic, palmitic, heptadecanoic, stearic, arachidic, behenic, lignoceric, a-linolenic, stearidonic, eicosapentaenoic, docosahexaenoic, linoleic, y-linolenic, dihomo-γ-linolenic, arachidonic, oleic, elaidic, eicosenoic, erucic, or nervonic acid, or mixtures thereof. The polyglycol moiety in a polyglycolized glyceride can be polydisperse; that is, they can have a variety of molecular weights.

Alkyl Saccharides

Alkyl saccharides can be used in the o pharmaceutical compositions of the invention. Alkyl saccharides are sugar ethers of a hydrophobic alkyl group (e.g., typically from 9 to 24 carbon atoms in length). Alkyl saccharides include alkyl glycosides and alkyl glucosides. In particular embodiments, the cefepime is formulated with a C8-14 alkyl ether of a sugar. Alkyl glycosides that can be used in the oral dosage forms of the invention include, without limitation, C8-14 alkyl (e.g., octyl-, nonyl-, decyl-, undecyl-, dodecyl-, tridecyl-, or tetradecyl-) ethers of a or B-D-maltoside, -glucoside or -sucroside, alkyl thiomaltosides, such as heptyl, octyl, dodecyl-, tridecyl-, and tetradecyl-B-D-thiomaltoside; alkyl thioglucosides, such as heptyl- or octyl 1-thio a- or -D-glucopyranoside; alkyl thiosucroses; and alkyl maltotriosides. For example, the bumetanide can be formulated with octyl maltoside, dodecyl maltoside, tridecyl maltoside, or tetradecyl maltoside. Alkyl glucosides that can be used in the oral dosage forms of the invention include, without limitation, C8-14 alkyl (e.g., octyl-, nonyl-, decyl-, undecyl-, dodecyl-, tridecyl-, or tetradecyl-) ethers of glucoside, such as dodecyl glucoside or decyl glucoside.

Ester Saccharides

Ester saccharides can be used in the pharmaceutical compositions of the invention. Ester saccharides are sugar esters of a hydrophobic alkyl group (e.g., typically from 8 to 24 carbon atoms in length). Ester saccharides include ester glycosides and ester glucosides. In particular embodiments, the cefepime is formulated with a C8-14 alkyl ester of a sugar. Ester glycosides that can be used in the oral dosage forms of the invention include, without limitation, C8-14 alkyl (e.g., octyl-, nonyl-, decyl-, undecyl-, dodecyl-, tridecyl-, or tetradecyl-) esters of a or B-D-maltoside, -glucoside or -sucroside. For example, the bumetanide can be formulated with sucrose mono-dodecanoate, sucrose mono-tridecanoate, or sucrose mono-tetradecanoate. Ester glucosides that can be used in the oral dosage forms of the invention include, without limitation, C8-14 alkyl (e.g., octyl-, nonyl-, decyl-, undecyl-, dodecyl-, tridecyl-, or tetradecyl-) esters of glucoside, such as glucose dodecanoate or glucose decanoate.

Polysorbate Surfactants

Polysorbate surfactants can be used in the pharmaceutical compositions of the invention. Polysorbate surfactants are oily liquids derived from pegylated sorbitan esterified with fatty acids. Common brand names for Polysorbates include Alkest, Canarcel and Tween. Polysorbate surfactants include, without limitation, polyoxyethylene 20 sorbitan monolaurate (TWEEN® 20), polyoxyethylene (4) sorbitan monolaurate (TWEEN® 21), polyoxyethylene 20 sorbitan monopalmitate (TWEEN® 40), polyoxyethylene 20 sorbitan monostearate (TWEEN® 60); and polyoxyethylene 20 sorbitan monooleate (TWEEN® 80).

Viscosity Enhancers

Viscosity enhancers can be used in the pharmaceutical compositions of the invention formulated for nasal administration. Viscosity enhancers that can be used in accordance with the present invention include, without limitation, cellulose derivatives, carbomers (Carbopol), gums, and hyaluronic acids (hyaluronates), dextrans, polyvinyl alcohol, polyacrylic acids, povidone, polyethylene glycol, polyols (e.g., glycerol), propylene glycol and chitosans; where for cellulose derivatives particularly preferred are one or more of carboxymethyl cellulose ("CMC") high molecular weight blend, CMC low molecular weight blend, CMC moderate molecular weight blend, Sodium CMC (low viscosity), methylcellulose, methyl cellulose 4000, hydroxymethyl cellulose, hydroxypropyl cellulose ("HPC"), hydroxypropylmethyl cellulose high molecular weight blend ("HPMC"), hydroxyl propyl methyl cellulose 2906, carboxypropylmethyl cellulose high molecular weight blend ("CPMC"), hydroxyethyl cellulose, or hydroxyethyl cellulose and hyaluronic acid. In particular embodiments, the viscosity enhancer is sodium CMC, preferably in combination with a polyol selected from the group consisting of mannitol, xylitol, sorbitol, isosorbide, erythritol, glycerol, maltitol and combinations thereof.

Tonicity Agents

Tonicity agents can be utilized in the pharmaceutical compositions of the invention to modulate the tonicity of the liquid pharmaceutical composition. Tonicity in general relates to the osmotic pressure of a solution and is typically assessed relative to that of human blood serum. Tonicity agents may be included in pharmaceutical compositions (e.g., pharmaceutical dosage forms) to increase osmolality. Non-limiting examples of tonicity agents include substantially neutral buffering agents (e.g., phosphate buffered saline, tris buffer, or artificial perilymph), dextrose, mannitol, trehalose, sucrose, sorbitol, glycerin (aka glycerol), potassium chloride, and sodium chloride (e.g., as a hypertonic, isotonic, or hypotonic saline) as well amino acids (e.g., arginine, glycine, ornithine, lysine, histidine, glutamic acid, aspartic acid, isoleucine, leucine, alanine, phenylalanine, tyrosine, tryptophan, methionine, serine, and proline). Pharmaceutical compositions (e.g., pharmaceutical dosage forms) include sufficient amount of tonicity agents to provide for administration to a subject a hypertonic pharmaceutical dosage form.

Buffering Agents

In some embodiments, the pharmaceutical composition includes a buffering agent. A buffering agent may be included in the pharmaceutical composition to increase stability of the composition by maintaining a consistent pH range. A buffering agent may improve the ability of the composition to be absorbed by the subject. Additionally, the buffering agent may act to increase the solubility of the composition. A buffering agent may increase the solubility of the drug by maintaining a high solubility of the drug at a constant pH range, preferably pH 6-8. The buffering agents that can be used in accordance with the present invention include but are not limited to, potassium hydroxide, arginine, and Lysine. One or more components of the pharmaceutical composition (e.g., potassium hydroxide, arginine, and Lysine) may act as the counter ion species of the buffer in which the bumetanide also functions as a buffering agent. A buffering agent may be added to the pharmaceutical composition depending on if the method of administration requires a specific pH range be maintained.

Preservatives

In some embodiments of the pharmaceutical composition, a preservative is included as part of the pharmaceutical composition in order to increase the stability and/or shelf-life of the pharmaceutical composition. A preservative may be in the form of an antioxidant, an antimicrobial agent, or a chelating agent for example. An antioxidant may be added to the pharmaceutical composition in order to prevent the oxidation of other components in the composition that may be sensitive to oxidation in the presence of oxygen or sunlight. An antimicrobial agent may be included in the pharmaceutical composition in order to inhibit contamination of the pharmaceutical composition by microbes. A chelating agent may be added to the pharmaceutical composition to bind the pharmaceutically active ingredient to protect it from deterioration and increase stability. The preservatives that can be used in accordance with the present invention include, without limitation, benzyl alcohol, benzoic acid, and ethylenediaminetetraacetic acid (EDTA).

Permeation Enhancers

In some embodiments of the pharmaceutical compositions for nasal administration, a permeation enhancer may be included in the formulation to increase the intranasal bioavailability of the bumetanide. Examples of permeation enhancers that can be used in the pharmaceutical compositions of the invention include alcohol, aprotinin, benzalkonium chloride, benzyl alcohol, capric acid, ceramides, cetylpyridinium chloride, chitosan, cyclodextrins, deoxycholic acid, glycocholic acid, decanoyl, dimethyl sulfoxide, glyceryl monooleate, glycofurol, glycosylated sphingosines, glycyrrhetinic acids, 2-hydroxypropyl-P-cyclodextrin, laureth-9, lauric acid, lauroyl carnitine, sodium lauryl sulfate, lysophosphatidylcholine, menthol, poloxamer 407 or F68, poly-L-arginine, polyoxyethylene-94auryl ether, isopropyl myristate, isopropyl palmitate, lanolin, linoleic acid, medium chain triglycerides (MCT) menthol, myristic acid, myristyl alcohol, oleic acid, or salt thereof, oleyl alcohol, palmitic acid, polysorbate 80, propylene glycol, polyoxyethylene alkyl ethers, polyoxylglycerides, pyrrolidone, quillaia saponin, salicylic acid, sodium salt, b-sitosterol b-D-glucoside, sucrose cocoate, taurocholic acid, taurodeoxycholic acid, taurodihydrofusidic acid, thymol, tricaprylin, triolein, and alkylsaccharides, and combinations thereof, including but not limited to dodecyl maltoside, dodecyl-D-maltoside, tetradecyl maltoside, tetradecyl-b-D-maltoside and sucrose dodecanoate. Certain permeation enhancers can also function as surfactants (solubilizers) of bumetanide including, without limitation, glycerides, alkyl saccharides, ester saccharides, polyglycolized glycerides, and polysorbate surfactants. In particular embodiments, the permeation enhancer used in the pharmaceutical composition of the invention is selected from tetradecyl-B-D-maltoside, soy lecithin, lecithin (E80)distearoyl glycerol-3-phosphatidylamine, and L-a-phosphatidylethanolamine and bis (2-ethylhexyl)amine.

Dosing Regimens

The dosing regimen used for the treatment methods described herein can vary depending on many factors, e.g., the age, health, and weight of the recipient; the nature and extent of the symptoms of edema; and the frequency and type of concurrent treatment, if any. One of skill in the art can determine the appropriate dosage based on the above factors. The compounds used in the methods described herein may be administered initially in a suitable dosage that may be adjusted as required, depending on the individual response. In general, a suitable dose of bumetanide according to the invention will be in the range of between 0.5 and 10 mg (e.g., 0.5, 2.0, and 5 mg) of bumetanide in from 1 to 4 doses over a 1 to 4 hour period until the patient is no longer in an edematous state. Four doses of 100 µL per dose of the pharmaceutical composition may be delivered to the subject over a period of less than 1 hour. Alternatively, two doses of about 100 µL per dose may delivered to a subject followed by two more does of about 100 µL each after a period of about 30 to 60 minutes. The bumetanide can be administered to a patient at the onset of symptoms of edema, alternatively, the bumetanide is administered to a patient after symptoms persist following the failure of previously administered oral diuretics to treat the edema. If oral diuretics have been administered without effect, the patient may be restricted to an initial dose of less than 5 mg of bumetanide for a period of least 1 or 2 hours to further reduce the risk of over-diuresis, which may present as symptoms of dehydration and low blood pressure in the subject suffering from over-diuresis.

For the extended release formulation administered as a subcutaneous depot, the suitable dose of bumetanide according to the invention will be in the range of between 0.75 and 10 mg (e.g., 1.5±0.5, 2.5 ±0.5, 3.5±0.5, 4.5±0.5, 5.5±0.5, 6.5±0.5, 7.5±0.5, 8.5±0.5, and 9.5±0.5 mg) of bumetanide in from 1 to 2 doses over a 1 to 5 day period. The subcutaneous depot of bumetanide can be administered to a patient to prophylactically treat symptoms of edema and reduce the risk of rehospitalization.

Oral Diuretics

The disclosure features methods and compositions for the treatment of edema refractory to oral diuretics. Oral diuretics have long been used to relieve fluid retention, a hallmark of congestive heart failure. Aggressive use of diuretics, even in people taking ACE inhibitors, can reduce hospitalizations and improve exercise capacity. Diuretics act on the kidneys to rid the body of excess salt and water. They reduce the accumulation of fluid in the legs, abdomen and lungs, lower blood pressure and improve the efficiency of the circulation. Side effects of diuretics include low blood pressure, dehydration, and kidney dysfunction; they also may trigger gout, increase blood sugar and triglyceride, LDL, and overall cholesterol levels and may deplete the B vitamin thiamin. Although many diuretics are available, they are generally categorized as thiazides and loop diuretics, used with or without potassium-sparing agents. It is important to note that a recent study found an increased incidence of hospitalization in patients who were taking nonsteroidal anti-inflammatory drugs (NTHEs) along with diuretics. Common NSAIDS include aspirin, ibuprofen, and naproxen. Thiazides, including hydrochlorothiazide (HydroDIURIL, Esidrix), chlorothiazide (Diuril), metolazone (Zaroxolyn), and chlorthalidone (Hygroton), are usually prescribed for patients with mild heart failure and good kidney function.

Loop diuretics, such as furosemide (Lasix), bumetanide (BumeX), and ethacrynic acid (Edecrine), are generally used for more severe heart failure, especially when kidney function is impaired. Loop diuretics are used intravenously to treat pulmonary edema and acute congestive heart failure, a thiazide and a loop diuretic may be administered simultaneously. Fluid may persist in the lungs even after standard treatment for congestive failure, limiting the patient's ability to function normally. One study treated patients with this condition very aggressively with furosemide to further reduce fluids, but no improvement was observed. Another method using a filtration technique was more successful.

Potassium loss is a major problem with diuretic use. Unless patients are also taking ACE inhibitors, which raise potassium levels, the physician may recommend a potassium supplement or the use of a potassium-sparing diuretic, such as spironolactone (Aldactone), amiloride (Midamor), and triamterene (Dyrenium), along with a thiazide or loop diuretic. All patients receiving diuretics with or without potassium-sparing drugs should have their blood potassium levels checked at regular intervals.

The methods of the invention can include the bumetanide therapy described herein used in combination with oral diuretics, such as loop diuretics, potassium-sparing diuretics, thiazides, or other oral diuretics, to manage edema in patients. Typically, the intranasally or subcutaneously administered bumetanide is administered to a patient having taken oral diuretics previously, for example, within the past 1 hour, 2 hours, or 4 hours, for edema that is discovered to be refractory to oral diuretics. For example, the patient may be taking oral diuretics, such as high ceiling loop diuretics (e.g., furosemide, ethacrynic acid, torsemide and bumetanide), thiazides (e.g., hydrochlorothiazide acid), carbonic anhydrase inhibitors (e.g., acetazolamide and methazolamide), potassium-sparing diuretics (e.g., aldosterone antagonists: spironolactone, and epithelial sodium channel blockers: amiloride and triamterene), and/or calcium-sparing diuretics. The patient can continue with their regular regimen of oral diuretics following successful treatment of the acute edematous state using the methods of the invention.

Selection of Subject

The methods and compositions of the invention can be used in patients generally at risk of edema. The edema may be, for example, pedal edema, peripheral edema, lung edema (e.g., pulmonary edema). The methods and compositions of the invention may be used where the subject is a mammal. Specifically, the subject may be a dog, where the dog is need of veterinary care. Additionally, the subject may be a human. Subjects that may be treated using the methods described herein are subjects having a diagnosis of congestive heart failure. Congestive heart failure (CHF) is characterized by an inability of the heart to generate sufficient cardiac output to meet the body's demands. Patients having CHF experience signs and symptoms of intravascular and interstitial volume overload, including shortness of breath, rapid heart rate, fluid in the lungs, and edema, along with indicators of inadequate tissue perfusion, including fatigue and/or poor exercise tolerance. Subjects that may be treated include those that have heart failure diagnosed by the standard and routine diagnostic procedures known in the art (e.g., electrocardiogramaction fraction), radionuclide imaging, magnetic resonance imaging, computed tomography imaging, cardiac catheterization with angiography, heart muscle biopsy, and/or assessment of atrial natriuretic peptide (ANP) and/or B-type natriuretic peptide levels in the blood (BNP)).

Subjects that may be treated are currently experiencing symptoms known to be associated with congestive heart failure, such as shortness of breath (e.g. dyspnea), fatigue, weakness, peripheral edema, or fluid overload. Subjects may be taking a daily dosage of oral diuretics, such as loop diuretics, potassium-sparing diuretics, or thiazides, to reduce the fluid overload and edema along with any one of the symptoms associated with congestive heart failure.

Subjects that may be treated using the methods described herein are experiencing symptoms of renal insufficiency caused by a reduction in blood flow, such as decreased urine output, swelling of the legs, ankles, feet, or abdomen, shortness of breath or fatigue caused by fluid overload as a result of the renal insufficiency. Subjects may experience fluid overload to the level wherein intestinal mobility becomes compromised preventing normal absorption of ingested nutrients, leading to inadequate gastrointestinal absorption, making for reduced bioavailability of pharmaceutical compositions administered orally.

Subjects that may be treated using the methods described herein can be experiencing symptoms of refractory edema as a result of congestive heart failure along with decreased intestinal mobility, thus preventing the subject's oral diuretics from effectively causing diuresis to remove excess bodily fluid. As a result of the persistence of symptoms of edema such as fatigue, shortness of breath and swollen limbs and abdomen, the subject seeks hospitalization to be administered intravenous diuretics, which then have the potential to put the subject at risk for kidney failure.

The subcutaneous administration of an extended release depot formulation can be used to prophylactically treat a patient and allow the patient to benefit from a reliable diuretic effect over a period of days without complications. The extended release therapy can be used to treat a patient at risk of rehospitalization. For example, following hospitalization for the treatment of congestive heart failure, the patient can receive treatment after discharge from the hospital, such that diuresis is achieved and symptoms such as shortness of breath, fatigue, and edema are relieved for an extended period of time (e.g., days).

EXAMPLES

The following examples are put forth so as to provide those of ordinary skill in the art with a description of how the compositions and methods described herein may be used, made, and evaluated, and are intended to be purely exemplary of the disclosure and are not intended to limit the scope of what the inventors regard as their disclosure.

Example 1. Solubility of Bumetanide in Water in the Presence and Absence of Surfactant Bumetanide, 10 mg, in its free acid form was added to 1 mL of deionized water and mixed using a vortex and sonicator. The solution was filtered using a 0.22 µm nylon syringe filter. To 900 L deionized water, 100 µL of the filtered bumetanide solution was added before being characterized for the concentration of the bumetanide in solution using HPLC. The concentration of bumetanide was determined using a standard curve generated by bumetanide solutions of known concentrations. Nearly no bumetanide in the free acid form was soluble water. Therefore, to the 10 mg of bumetanide, 1 mL of deionized water containing 1.0%, 0.5% or 0.1% of the surfactant tetradecyl-B-D-maltoside. The bumetanide was then solubilized using a vortex and sonicator, after which it was filtered using a 0.22 µm nylon syringe filter. To 900 µL deionized water, 100 µL of the filtered bumetanide solution was added before being characterized for the concentration of the bumetanide in solution using HPLC. The resulting bumetanide concentrations are recorded in Table 1.

TABLE 1

| Measured solubility of bumetanide with a non-ionic surfactant | | | | |
|---|---|---|---|---|
| Sample | Calculated conc. (mg/mL) | pH | Surfactant added | Amount added (% wt) |
| F39 | 0.01 | 4 | Tretradecycl-β-D-Maltoside | 0.1% |
| F40 | 0.08 | 4 | (non-ionic solubilizer) | 0.5% |
| F41 | 0.21 | 4 | | 1.0% |

While addition of the surfactant, did improve the amount of bumetanide able to be solubilized in water, these results clearly show that when bumetanide is not in a salt form, it has incredibly low solubility in water despite the presence of a surfactant.

Example 2. Solubility of Bumetanide Salts

The acid form of bumetanide was weighed out to 20 mg and dissolved in 1 mL of deionized water by mixing with a vortex to form a low-pH solution of bumetanide. To this low pH bumetanide solution, a determined amount of base was added and mixed using a vortex for 2 minutes, to form a solution having a pH suitable for nasal administration. With the increasing pH the bumetanide salt formed in situ precipitated, in part, to form a saturated solution of the resulting salt form. The saturated solution was then filtered through a 0.22 µm filter to remove all precipitated bumetanide salt. The filtrate was collected, and its pH was measured. An aliquot of the saturated solution was assayed for bumetanide by HPLC to determine the maximum concentration achievable for the salt form in water at about neutral pH.

This procedure was repeated for various bases, including arginine, lysine, potassium, sodium, glycine, histidine, and the cationic lipophilic surfactants soy lecithin, distearoyl glycerol-3-phosphatidylamine, L-a-phosphatidylethanolamine and bis(2-ethylhexyl)amine, in order to determine the maximum solubility of each bumetanide salt solution. The concentration of bumetanide in solution for each bumetanide salt form is recorded in Table 2 in order to determine the maximum solubility of each bumetanide salt.

TABLE 2

| Measured solubility of bumetanide salt with various bases | | | | | |
|---|---|---|---|---|---|
| Sample | Calculated conc. (mg/mL) | pH | Base added | Base added (mg) | Bumetanide:Base (Salt ratio) |
| F22 | 8.94 | 6.98 | Arginine | 4.94 | |
| F23 | 5.65 | 6.94 | MW 174.2 | 5.14 | |
| F24 | 11.65 | 7.04 | | 5.84 | |
| F25 | 12.60 | 7.10 | | 7.94 | (1.1:1) |

TABLE 2-continued

Measured solubility of bumetanide salt with various bases

| Sample | Calculated conc. (mg/mL) | pH | Base added | Base added (mg) | Bumetanide:Base (Salt ratio) |
|---|---|---|---|---|---|
| F26 | 5.89 | 6.87 | Lysine | 3.94 | |
| F27 | 4.56 | 6.85 | MW 146.19 | 5.12 | |
| F28 | 6.07 | 6.83 | | 6.00 | |
| F29 | 7.08 | 6.93 | | 6.93 | (1.1:1) |
| F30 | 7.75 | 7.14 | KOH | 1.12 | |
| F31 | 14.04 | 7.13 | MW 56.11 | 2.24 | |
| F32 | 16.97 | 7.23 | | 2.81 | (1:1) |
| F33 | 20.19 | 7.27 | | 3.37 | (1:1.1) |
| F34 | 5.67 | 7.03 | NaOH | 0.80 | |
| F35 | 5.58 | 6.99 | MW 39.998 | 1.60 | |
| F36 | 5.62 | 9.39 | | 2.00 | |
| F37 | 6.59 | 10.19 | | 2.40 | (1:1) |
| F45 | 0.03 | 5.11 | Glycine | 4.14 | (1:1) |
| F46 | 0.04 | 5.16 | MW 75.1 | 6.28 | |
| F47 | 0.05 | 5.15 | | 8.34 | |
| F48 | 0.06 | 5.18 | | 10.06 | (1:2) |
| F49 | 2.04 | 6.47 | Histidine | 4.04 | |
| F50 | 3.42 | 6.50 | MW 155.2 | 5.02 | |
| F51 | 3.23 | 6.62 | | 6.09 | |
| F52 | 3.52 | 6.68 | | 8.03 | (1:1) |
| F53 | 0.25 | 4.56 | Soy Lecithin (Cationic surfactant) | 10.14 | |
| F57 | 0.00 | 6.05 | Distearoyl glycerol-3- | 20.87 | |
| F58 | 0.00 | 6.03 | phosphatidylamine | 25.78 | |
| F59 | 0.00 | 5.05 | MW 748.1 | 32.6 | |
| F60 | 0.00 | 4.54 | | 41.78 | (1:1) |
| F71 | 0.01 | 4.07 | L-α- | 4.98 | |
| F72 | 0.01 | 3.97 | Phosphatidylethanolamine | 6.02 | |
| F73 | 0.01 | 3.68 | (di-ionic surfactant) | 7.97 | |
| F74 | 0.00 | 3.72 | (MW 523.68) | 9.99 | |
| F75 | 0.19 | 5.45 | Bis(2-ethylhexyl)amine | 6.47 | |
| F76 | 0.19 | 5.51 | MW 241.61 | 8.31 | |
| F77 | 0.18 | 5.79 | | 9.83 | |
| F78 | 0.18 | 5.8 | | 12.98 | (1:1) |

Figure 1:
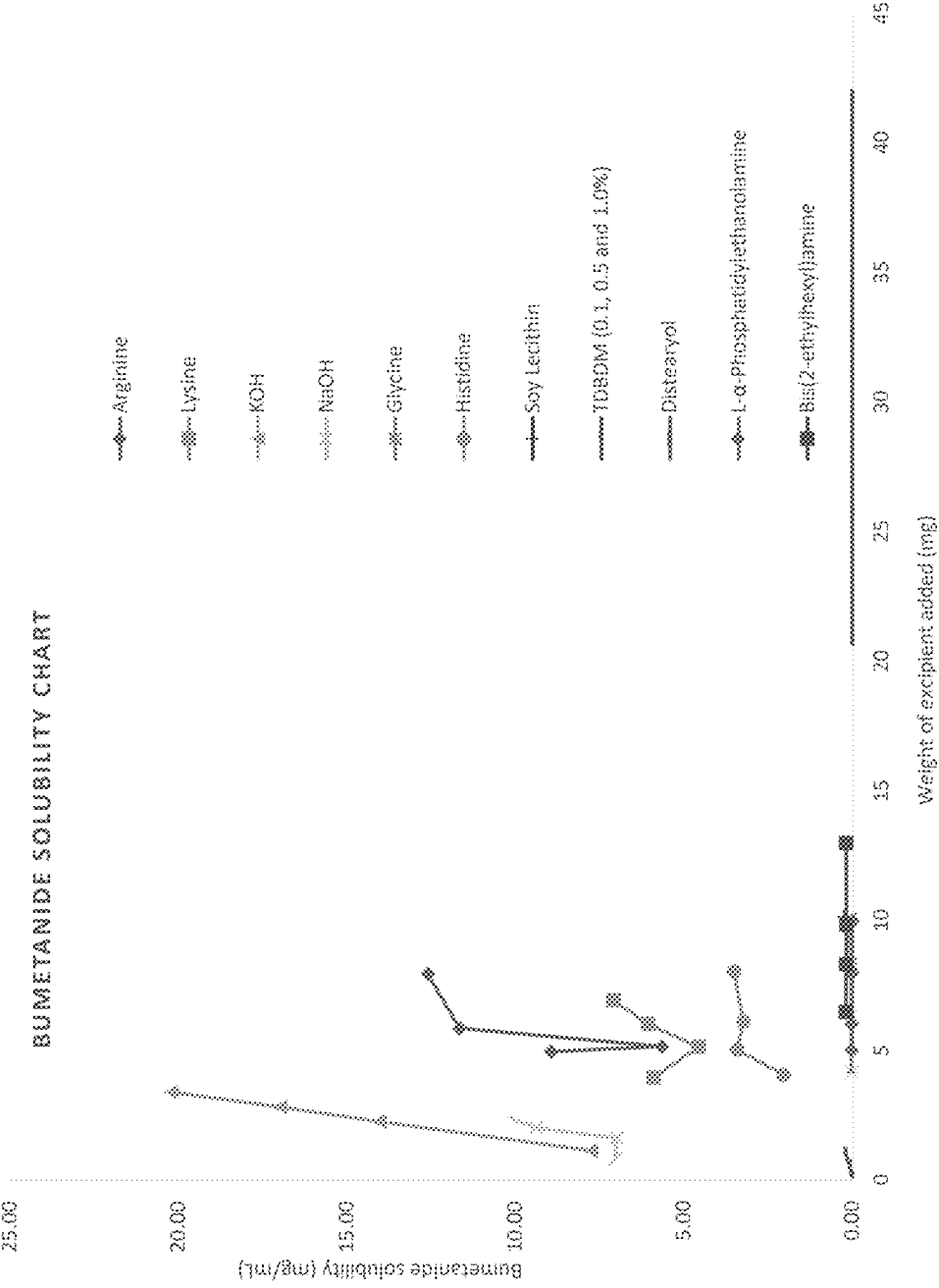
FIG. 1 is a graph showing the solubility (mg/ml) of various bumetanide salt forms compared to the weight (mg) of the excipient that was added per 20 mg of bumetanide.

This solubility data clearly shows the highest concentration of bumetanide salt in solution is achieved when either arginine or potassium are acting as the base with their greatest concentrations measured to be 12.6 mg/mL and 20.19 mg/mL respectively. The solubility of the bumetanide salt is significantly increased when potassium hydroxide acting as the base as opposed to another base such as sodium hydroxide which has a measured solubility of 6.59 mg/mL, as is shown in FIG. 1. It is surprising that the solubility of the bumetanide salt is significantly increased when arginine is acting as the base as opposed to another amino acid base such as lysine, which has a measured solubility of 7.08 mg/mL. As shown in FIG. 1, the potassium salt of bumetanide achieves the highest solubilities at pharmaceutically desirable pHs (e.g., pH 6-8) with the lowest mass burden to the transmucosal formulation, resulting in concentrations that (as shown in the animal studies) can produce a PK performance similar to that produced with IV injection without the complications and risks associated with IV administration.

Example 3. Solubility of Bumetanide in Different pH Buffers

The solubility of bumetanide was assessed in various pH buffers. 10 mg of bumetanide was weighed into a 3 mL glass vial. To the vial, 2 mL of buffer with a desired pH was added. The solution was then sonicated for 2 hours at room temperature (25° C.) and then rotated overnight. The solution was then filtered through a 0.2 µm nylon syringe filter, and the first 0.5 mL was discarded. The filtrate was then diluted 10× and at least 0.5 mL was aliquoted into an HPLC vial. 1 M sodium citrate was used for F1 to F4, and 1 M sodium phosphate buffer was used for F5 to F9. The resulting concentration of bumetanide in solution was measured for each pH buffer and the results are summarized in Table 3.

TABLE 3

Solubility of Bumetanide in solution in various pH buffers

| Sample | pH | Inj#1 | Inj#2 | Avg PA | R.T. (min) | Conc.(µg/mL) (API solubility in buffer solutions) |
|---|---|---|---|---|---|---|
| F1 | 4.0 | N/D | N/D | — | — | — |
| F2 | 4.5 | 18.2 | 19.5 | 18.9 | 11.79 | 7.2 |
| F3 | 5.0 | 87.0 | 89.4 | 88.2 | 11.80 | 33.8 |
| F4 | 5.5 | 180.8 | 184.3 | 182.6 | 11.80 | 69.9 |
| F5 | 6.0 | 83.4 | 84.9 | 84.2 | 11.81 | 32.2 |
| F6 | 6.5 | 157.2 | 159.6 | 158.4 | 11.81 | 60.6 |
| F7 | 7.0 | 356.3 | 360.8 | 358.6 | 11.81 | 137.3 |
| F8 | 7.5 | 564.0 | 565.9 | 565.0 | 11.82 | 216.3 |
| F9 | 8.0 | 760.1 | 752.6 | 756.4 | 11.81 | 289.6 |

1 g of Kolliphor RH40 and 9 g of ethanol was added to a 15 mL Falcon tube. The solution was mixed and vortexed as needed. 50 mg of bumetanide salt was weighed out and transferred into the solution and mixed, vortexed, or sonicated as needed to dissolve solids to form a 5 mg/g stock solution. If all solids dissolved, 10 more mg of bumetanide salt was added. 1.0 g of this stock solution was added to a 10 mL glass vial using a 0.22 µm nylon syringe filter. The pH of the solution was measured and adjusted with 0.1 N HCl or NaOH such that was within the target pH by ±/−0.1. If there was no precipitate in the vial, 0.5 mL of each formulation was aliquoted into a 1.5 mL HPLC vial for a total of 20 vials. If there was precipitate, the solution was transferred with the precipitate into a 10 ml syringe and filtered through a 0.45 μm filter. The filtrate was collected and aliquoted into 0.5-1.0 mL of each formulation in a 1.5 mL HPLC vial for total 15 vials. Each vial was crimp sealed. 4 vials were placed at 40° C., 4 vials were placed at 50° C., and 4 vials were placed at 60° C. 2 vials were placed at −80° C. for back up. The last vial was used for T0 assay analysis. The pH and concentration of the various formulations was measured on the day of, 3 days, 7 days, and 10 days of being stored at the indicated temperatures. The results are summarized in Table 4. The percent bumetanide recovery was also measured on these days, and the results are summarized in Table 5.

TABLE 4

Solubility of Bumetanide in solution in various pH buffers at variable temperature T0 assay:

| Sample | Inj#1 | Inj#2 | Avg PA | Conc.(mg/g) |
|---|---|---|---|---|
| F5 pH 6.1 | 13643.6 | 13620.1 | 13631.9 | 5.23 |
| F6 pH 6.5 | 12914.5 | 12956.2 | 12935.4 | 5.24 |
| F7 pH 7.0 | 14852.8 | 14814.2 | 14833.5 | 5.74 |
| F8 pH 7.6 | 15101.9 | 15050.4 | 15076.2 | 5.79 |
| F9 pH 8.0 | 15108.2 | 15095.6 | 15101.9 | 5.90 |

T 3DAY assay:

| Sample | 25° C. | | 40° C. | | 50° C. | | 60° C. | |
| | pH | Conc.(mg/g) | pH | Conc.(mg/g) | pH | Conc.(mg/g) | pH | Conc.(mg/g) |
|---|---|---|---|---|---|---|---|---|
| F5 | 7.0 | 5.78 | 7.5 | 5.84 | 7.5 | 5.83 | 7.5 | 5.78 |
| F6 | 6.8 | 5.92 | 6.9 | 5.99 | 6.9 | 5.96 | 6.9 | 5.92 |
| F7 | 7.5 | 5.92 | 7.7 | 5.91 | 7.8 | 5.85 | 7.8 | 5.87 |
| F8 | 7.9 | 5.88 | 8.2 | 5.85 | 8.3 | 5.81 | 8.2 | 5.81 |
| F9 | 8.5 | 5.98 | 8.5 | 5.95 | 8.4 | 5.92 | 8.3 | 5.92 |

T 7DAY assay:

| Sample | 25° C. | | 40° C. | | 50° C. | | 60° C. | |
| | pH | Conc.(mg/g) | pH | Conc.(mg/g) | pH | Conc.(mg/g) | pH | Conc.(mg/g) |
|---|---|---|---|---|---|---|---|---|
| F5 | 7.2 | 5.79 | 7.2 | 5.82 | 7.3 | 5.82 | 7.3 | 5.79 |
| F6 | 6.8 | 5.99 | 6.8 | 5.94 | 6.9 | 5.95 | 6.9 | 5.96 |
| F7 | 7.6 | 5.90 | 7.8 | 5.88 | 7.7 | 5.89 | 7.8 | 5.87 |
| F8 | 8.1 | 5.79 | 8.1 | 5.80 | 8.1 | 5.79 | 8.0 | 5.85 |
| F9 | 8.2 | 5.94 | 8.3 | 5.90 | 8.3 | 5.87 | 8.2 | 5.90 |

T 10DAY assay

| Sample | 25° C. | | 40° C. | | 50° C. | | 60° C. | |
| | pH | Conc.(mg/g) | pH | Conc.(mg/g) | pH | Conc.(mg/g) | pH | Conc.(mg/g) |
|---|---|---|---|---|---|---|---|---|
| F5 | 7.2 | 5.82 | 7.2 | 5.82 | 7.3 | 5.80 | 7.3 | 5.85 |
| F6 | 6.8 | 5.98 | 6.8 | 5.98 | 6.8 | 5.91 | 6.8 | 5.98 |
| F7 | 7.6 | 5.90 | 7.6 | 5.88 | 7.5 | 5.85 | 7.6 | 5.90 |
| F8 | 7.9 | 5.85 | 8.0 | 5.77 | 8.0 | 5.80 | 7.9 | 5.84 |
| F9 | 8.2 | 5.92 | 8.1 | 5.91 | 8.0 | 5.85 | 7.8 | 5.92 |

TABLE 5

Percent recovery of bumetanide at various temperatures over time

| Sample | Time (day) | 25° C. Assay Recovery % over TO | 40° C. Assay Recovery % over TO | 50° C. Assay Recovery % over TO | 60° C. Assay Recovery % over TO |
|---|---|---|---|---|---|
| F5* | 0 | — | — | — | — |
|  | 3 | 110.6 | 111.6 | 111.4 | 110.5 |
|  | 7 | 110.8 | 111.2 | 111.2 | 110.8 |
|  | 10 | 111.3 | 111.2 | 110.8 | 111.9 |
| F6* | 0 | — | — | — | — |
|  | 3 | 112.9 | 114.3 | 113.8 | 113.0 |
|  | 7 | 114.2 | 113.3 | 113.4 | 113.8 |
|  | 10 | 114.0 | 114.0 | 112.8 | 114.1 |
| F7 | 0 | — | — | — | — |
|  | 3 | 103.2 | 102.9 | 102.0 | 102.3 |
|  | 7 | 102.8 | 102.4 | 102.5 | 102.3 |
|  | 10 | 102.7 | 102.4 | 102.0 | 102.8 |
| F8 | 0 | — | — | — | — |
|  | 3 | 101.5 | 101.0 | 100.4 | 100.4 |
|  | 7 | 100.1 | 100.2 | 100.0 | 101.1 |
|  | 10 | 101.1 | 99.6 | 100.1 | 100.9 |
| F9 | 0 | — | — | — | — |
|  | 3 | 101.4 | 101.0 | 100.4 | 100.5 |
|  | 7 | 100.7 | 100.1 | 99.6 | 100.1 |
|  | 10 | 100.4 | 100.3 | 99.2 | 100.4 |

Example 4. Emulsion Formulations of Bumetanide Salts

Emulsion formulations of bumetanide salts were developed for increased adsorption of bumetanide during intranasal administration. Glycerol (2.25% weight), medium chain triglycerides (MCT) (10% weight) and lecithin (E-80) (1.2% weight) were weighed out and dissolved by way of sonication for 30 minutes, which was followed by addition of 86% weight deionized water and additional mixing until a clear and colorless solution was obtained to generate the FEV-1 product described in Table 6. FEV-2 was generated by weighing out MCT and lecithin into a tared 50 mL falcon tube and sonicated for about 30 min at 50° C. to ensure all solid dissolved. DI-water was mixed in with the solution and a white emulsion was obtained, as described in Table 6.

TABLE 6

Composition and compounding of FEV-1 and FEV-2

| Ingredient | FEV-1 (%, wt) | FEV-1 (mg/10 g) | FEV-2 (%, wt) | FEV-2 (mg/10 g) |
|---|---|---|---|---|
| MCT | 10 | 1000 | 10 | 1000 |
| Glycerol | 2.25 | 225 | — | — |
| Lecithin (E-80) | 1.2 | 120 | 1.2 | 120 |
| DI-water | 86.0 | 8600 | 88.8 | 8880 |

The FE-V1 product was used to prepare emulsions FE-1-FE-7 with various emulsifying agents. The FE-V2 product was used to prepare the FE-8 emulsion. These emulsions were prepared by weighing out bumetanide, an emulsifying agent (e.g. polysorbate 80, polysorbate 20 or PEG 400), and benzyl alcohol in the cases of FE-3-FE-6 as are described in Table 7. Each emulsion formulation was brought to 1000 mg using the FEV-1 solution and BB for 30 seconds for each formulation. The appearance is checked visually, and the pH is measured. For FE-6, the pH was adjusted to 5.7 using 1N NaOH, and for FE-7, the pH was adjusted to 6.5 using 1N NaOH. Each emulsion formulation was then filtered using a 0.22 µm filter syringe. The resulting filtrate was characterized using HPLC for their respective bumetanide concentrations as well as for any impurities.

TABLE 7

Compositions for formulations FE-1 to FE-7

| Ingredient | %, wt | | | | | | | | |
|---|---|---|---|---|---|---|---|---|---|
|  | FE-1 | FE-2 | FE-3 | FE-4 | FE-5 | FE-6 | FE-7 | FE-8 | FE-9 |
| Bumetanide | 0.5 | 0.5 | 1.0 | 1.0 | 1.0 | 0.6 | 0.6 | 0.5 | 0.5 |
| Polysorbate 80 | 5.0 | — | 5.0 | 8.0 | 8.0 | 8.0 | — | 8.0 | — |
| Polysorbate 20 | — | 5.0 | — | — | — | — | — | — | — |
| PEG 400 | — | — | 10.0 | — | 10.0 | — | — | — | — |
| Benzyl alcohol | — | — | 0.5 | 0.5 | 0.5 | 0.5 | 0.5 | 0.5 | — |
| FEV-1 | 94.5 | 94.5 | 83.5 | 90.5 | 80.5 | 90.9 | 98.9 | — | 99.5 |
| FEV-2 | — | — | — | — | — | — | — | 100 | — |
| pH | As is | As is | As is | As is | As is | 5.7 | 6.5 | | 6.1 |

The measured concentrations of bumetanide showed the highest concentrations were obtained with the emulsion formulation FE-6 with a bumetanide concentration of 6.55 mg/g as shown in Table 8.

TABLE 8

Measured bumetanide concentrations for emulsion compositions

| ID | FE-1 | FE-2 | FE-3 | FE-4 | FE-5 | FE-6 | FE-7 |
|---|---|---|---|---|---|---|---|
| Appearance | Translucent sol. | Translucent sol. with PPT | Milky liquid | Milky liquid | Milky liquid | Milky solution | Clear solution with PPT |

TABLE 8-continued

| Measured bumetanide concentrations for emulsion compositions | | | | | | | |
|---|---|---|---|---|---|---|---|
| ID | FE-1 | FE-2 | FE-3 | FE-4 | FE-5 | FE-6 | FE-7 |
| Filterable through 0.22 μm filter | Yes | Yes | Yes | Yes | Yes | Yes | Yes |
| pH | 4.11 | 3.86 | 3.23 | 2.92 | 3.07 | 5.74 | 6.46 |
| Conc. (mg/g) | 3.79 | 4.50 | 2.07 | 3.02 | 2.86 | 6.55 | 3.60 |

To test stability of FE-9 at various temperatures, FE-9 was filled into spray vials and were placed in a stability chamber at 2-8° C., vials were placed in a stability chamber at 25° C., and vials were placed at −20° C. A remaining vial was used to measure initial concentration and impurities. After 1 week, 2 weeks, and 4 weeks, a sample was removed from the stability chambers and their appearance was checked visually. The samples were then prepared for HPLC for assay and impurity analysis. At this time, the pH and osmolality of the formulation was measured. The osmolality was at TO

TABLE 8

| | | | | | | | QS | HPLC | | |
|---|---|---|---|---|---|---|---|---|---|---|
| | | | | | | Sample | to | conc. | Calculated | Recovery |
| Time | | | PA of | PA of | Average | Size | Volume | (mg/ | conc. | vs. |
| (weeks) | Sample | pH | Inj. 1 | Inj. 2 | PA | (mL) | (mL) | mL) | (mg/g) | T0 (%) |
| 0 | FE-9, T0 | 6.1 | 11571.3 | 11544 | 11557.7 | 0.518 | 5 | 0.48 | 4.59 | 100.0 |
| 1 | FE-9, 2-8° C. | 6.1 | 11468.4 | 11462.9 | 11465.7 | 0.501 | 5 | 0.47 | 4.69 | 102.2 |
| | FE-9, 25° C. | 6.1 | 11383.5 | 11287.4 | 11335.5 | 0.504 | 5 | 0.46 | 4.60 | 100.3 |
| 2 | FE-9, 2-8° C. | 6.1 | 11270.0 | 11256.1 | 11263.1 | 0.497 | 5 | 0.46 | 4.62 | 100.8 |
| | FE-9, 25° C. | 6.1 | 11742.7 | 11743.8 | 11743.3 | 0.518 | 5 | 0.48 | 4.63 | 100.9 |
| 4 | FE-9, 2-8° C. | 6.1 | 11225.1 | 11155.4 | 11190.3 | 0.501 | 5 | 0.46 | 4.59 | 100.1 |
| | FE-9, 25° C. | 6.1 | 11354.8 | 11333.8 | 11344.3 | 0.494 | 5 | 0.47 | 4.72 | 102.9 |

TABLE 9

FE-9 Actuation dose

| | Actuation Dose (mg) per 100 ul spray | | | |
|---|---|---|---|---|
| Sample | 1st | 2nd | 3rd | Average |
| FE-9, 2-8° C., 1 week | 113 | 122 | 122 | 119 |
| FE-9, 25° C., 1 week | 118 | 122 | 123 | 121 |
| FE-9, 2-8° C., 2 weeks | 100 | 121 | 112 | 111 |
| FE-9, 25° C., 2 weeks | 122 | 121 | 112 | 118 |
| FE-9, 2-8° C., 4 weeks | 93 | 91 | 87 | 90 |
| FE-9, 25° C., 4 weeks | 121 | 123 | 123 | 122 |

Particle size distribution analysis was performed to determine the average particle size for the FE-9 bumetanide emulsion was less than 200 nm using dynamic light scattering on a Malvern Panalytical Zetasizer. The FE-9 sample was prepared for analysis by performing two passes of the emulsion through a microfluidizer prior to particle size distribution analysis. This process was repeated if measured average particle size was greater than 200 nm. The average particle sizes for FE-9 stored both at room temperature and 2-8° C. over a period of 4 weeks were 112-120 nm as described in Table 10.

TABLE 10

| Particle size analysis for FE-9 emulsion | | | | | | |
|---|---|---|---|---|---|---|
| | T | Z-Ave | | D | D | D |
| Sample Name | (° C.) | (d.nm) | Pdl | (v, 0.1) | (v,0.5) | (v, 0.9) |
| FE-9_T0 | 25 | 112.0 | 0.173 | 41.4 | 74.8 | 227.0 |
| FE-9_2-8° C. 1 week | 25 | 112.5 | 0.140 | 53.9 | 87.9 | 216.0 |
| FE-9_25° C. 1 week | 25 | 115.0 | 0.117 | 59.2 | 94.0 | 212.0 |
| FE-9_2-8° C. 2 weeks | 25 | 118.4 | 0.111 | 62.6 | 99.4 | 217 |
| FE-9_25° C. 2 weeks | 25 | 119.5 | 0.127 | 58.3 | 94.5 | 237 |
| FE-9_2-8° C. 4 weeks | 25 | 118.3 | 0.126 | 62 | 99.5 | 220 |
| FE-9_25° C. 4 weeks | 25 | 119.8 | 0.122 | 60.6 | 97.1 | 234 |

FE-8 was prepared by weighing out each excipient into a tared 15 mL Falcon tube (see Table 7), and brought to QS with FEV-2. The pH was adjusted to 6.0 with 1N NaOH and vortexed to ensure no solid was in the mixture; sonication was used if necessary. The final pH was kept at 6.0 and the visual appearance was checked, pH was measured, and osmolality was measured. The solution was filtered through a 0.22 μm filter, and the filtrate was collected, and 1.0 mL was aliquoted into a 3 mL glass vial, which were crimped to seal the vial for total 8 vials.

To test stability at various temperatures, 3 vials were placed in a stability chamber at 2-8° C., 3 vials were placed in a stability chamber at 25° C., and 2 vials were placed at −20° C. The remaining vial was used to measure initial concentration and impurities. After 4 weeks, the samples were removed from the stability chambers and their appearance was checked visually. The samples were then prepared for HPLC for assay and impurity analysis. At this time, the pH and osmolality of the formulation was measured. Before the osmolality was measured, the 0.2 mL of the formulation was diluted with 1.8 mL of DI-water. The resulting concentration of bumetanide and the percent recovery for the samples stored at the various temperatures after 2 weeks is summarized in Table 11 and the osmolality was measured to be 5 mOsm with a dilution factor of 10 at TO.

TABLE 11

| | | | | FE-8 Stability Test after 2 weeks | | | | |
| Sample | PA of Inj. 1 | PA of Inj. 2 | Average PA | Sample Size (mL) | QS to Volume (mL) | HPLC conc. (mg/mL) | Calculated conc. (mg/g) | Recovery vs. T0 (%) |
|---|---|---|---|---|---|---|---|---|
| FE-8, −20° C. | 5763.8 | 5709.9 | 5736.9 | 0.25 | 5 | 0.24 | 4.76 | 102.0 |
| FE-8, 2-8° C. | 5831.4 | 5817.3 | 5824.4 | 0.25 | 5 | 0.24 | 4.78 | 102.4 |
| FE-8, 25° C. | 5711.1 | 5685.5 | 5698.3 | 0.25 | 5 | 0.23 | 4.67 | 100.1 |

Example 5. Nano-Emulsion Formulations for Bumetanide Salts

Nano-emulsion formulations of bumetanide salts were developed to improve mucosal absorption. Nano-emulsions were prepared by first generating the FNEV-1 formulation by weighing out glycocholic acid (46.8 mg) and suspending in sterile water for injection (SWFI) (600 mg) using a vortex as described in Table 12. To this solution, 10 N NaOH was added (10 µL) and mixed until the solution became clear. Soy lecithin (PL90G) and benzyl alcohol were added as described in Table 12 and dissolved completely using a vortex and a sonicator if necessary. The solution was brought to a final weight with deionized water as described in Table12 and mixed. The pH of this solution was measured and adjusted to a final pH of 7.0 after which the solution was allowed to shaker overnight to generate the FNEV-1 product.

TABLE 12

| | | Composition and compounding of FNEV-1 |
| | | FNEV-1 | |
| Excipient | Mg/g | 20 g Batch amount (mg) |
|---|---|---|
| Bumetanide | 0 | 0 |
| Soy lecithin (PL90G) | 100 | 2000 |
| Glycocholic acid | 46.8 | 936 |
| Benzyl alcohol | 9 | 180 |
| NaOH (10N) adjust pH to 7.0 | | |
| DI-H2O Q.S. to | 1 g | 20000 |

The FNEV-1 product was used to prepare the FNE-1 nano-emulsions with various pH values. The bumetanide nano-emulsions were prepared by weighing out bumetanide and dissolving in the FNEV-1 solution, as described in Table 13, using a vortex, and adjusting the pH to 5.0 or 6.0 using 1.0 N NaOH or 1.0 N HCl. The solutions were left standing overnight, after which the pH was measured. The solutions were filtered using a 0.22 µm centrifuge tube filter. The filtrates were then diluted by a factor of 20 and mixed using a vortex such that 0.25 mL of filtrate was diluted to a final volume of 5 mL before transferring the solution to the HPLC.

TABLE 13

| Composition of nano-emulsion FNE-1 | | |
| Ingredient | mg/g | 100 g Batch amount (g) |
|---|---|---|
| Bumetanide | 5 | 0.509* |
| FNEV-1 | 995 | 99.5 |
| Dextrose | | adjust osmolarity to about 290 |

*After taking Bumetanide purity (98.3%) into consideration.

The concentration of bumetanide in the FNE-1 solutions having final pH values of 5.3, 5.6, and 6.1 were measured using HPLC by comparison to solutions of known bumetanide concentration as shown in Table 14. The FNE-1 formulation with a pH of 6.1 showed the highest concentration of bumetanide in solution with a calculated concentration of 10.1 mg/mL. The results show the concentration of bumetanide in solution more than doubles when the pH of the nano-emulsion is changed from 5.3 to 6.1, thus, indicating that a pH of about 6 is optimal for concentrations of bumetanide in solution that are 5 mg/ml or greater.

TABLE 14

| | | | | | | Measured bumetanide concentrations for FNE-1 with various pH values | | |
| Sample | pH | PA of Inj. 1 | PA of Inj. 2 | Average PA | Sample Size (mL) | QS to Volume (mL) | HPLC conc. (mg/mL) | Calc. conc. (mg/g) |
|---|---|---|---|---|---|---|---|---|
| FNE-1, pH5.3 | 5.3 | 3740.6 | 3733.8 | 3737.2 | 0.25 | 5 | 0.16 | 3.1 |
| FNE-1, pH5.6 | 5.6 | 5579.3 | 5591.5 | 5585.4 | 0.25 | 5 | 0.23 | 4.7 |
| FNE-1, pH6.1 | 6.1 | 12005 | 11957.4 | 11981.2 | 0.25 | 5 | 0.50 | 10.1 |

Particle size distribution analysis was performed to determine the average particle size for the FNE-1 bumetanide nano-emulsion using dynamic light scattering on a Malvern Panalytical Zetasizer. The average particle sizes for FNE-1 with pH 6.0 stored both at room temperature and 2-8° C. over a period of 4 weeks were 9-11 nm as described in Table 15.

TABLE 15

| | | Particle size analysis of FNE-1 nano-emulsion | | | | |
|---|---|---|---|---|---|---|
| Sample Name | T (° C.) | Z-Ave (d.nm) | Pdl | D (v, 0.1) | D (v, 0.5) | D (v, 0.9) |
| FNE-1_2-8 C. 1 week | 25 | 9.883 | 0.544 | 1.01 | 1.41 | 2.29 |
| FNE-1_25 C. 1 week | 25 | 11.27 | 0.609 | 0.98 | 1.35 | 2.23 |
| FNE-1_2-8 C. 2 weeks | 25 | 9.681 | 0.535 | 0.93 | 1.30 | 2.18 |
| FNE-1 25 C. 2 weeks | 25 | 8.924 | 0.496 | 1.07 | 1.43 | 2.21 |
| FNE-1_2-8 C. 4 weeks | 25 | 10.5 | 0.573 | 0.981 | 1.34 | 2.19 |
| FNE-1_25 C. 4 weeks | 25 | 8.661 | 0.483 | 1.03 | 1.41 | 2.24 |

To test stability at various temperatures, filled spray vials were placed in a stability chamber at 2-8° C., vials were placed in a stability chamber at 25° C., and vials were placed at −20° C. A remaining vial was used to measure initial concentration and impurities. After 1 week, 2 weeks, and 4 weeks, the samples were removed from the stability chambers and their appearance was checked visually. The samples were then prepared for HPLC for assay and impurity analysis; at this time, the pH was also measured. The osmolality of the formulation was measured and found to be 140 Osm after a two-fold dilution, and the viscosity was 6 cp conducted at 10 rpm. The resulting concentration of bumetanide and the percent recovery for the samples stored at the various temperatures over 4 weeks is summarized in Table 16. The actuation dose was also measured for these samples and the resulting measurements are summarized in Table 17.

TABLE 16

| | | | | | | Sample | QS to | HPLC | Calculated | Recovery |
|---|---|---|---|---|---|---|---|---|---|---|
| Time (weeks) | Sample | pH | PA of Inj. 1 | PA of Inj. 2 | Average PA | Size (mL) | Volume (mL) | conc. (mg/mL) | conc. (mg/g) | vs. T0 (%) |
| 0 | FNE-1, T0 | 6.0 | 12335.2 | 12286.4 | 12310.8 | 0.499 | 5 | 0.51 | 5.09 | 100 |
| 1 | FNE-1, 2-8° C. | 6.0 | 12321.9 | 12415.2 | 12368.6 | 0.503 | 5 | 0.51 | 5.11 | 100.3 |
| | FNE-1, 25° C. | 6.0 | 11999.7 | 11917.6 | 11958.7 | 0.488 | 5 | 0.50 | 5.09 | 99.9 |
| 2 | FNE-1, 2-8° C. | 6.0 | 12723.7 | 12706.2 | 12715.0 | 0.508 | 5 | 0.52 | 5.08 | 99.8 |
| | FNE-1, 25° C. | 6.0 | 12170.4 | 12107.1 | 12138.8 | 0.495 | 5 | 0.49 | 4.99 | 98.0 |
| 4 | FNE-1, 2-8° C. | 6.0 | 12404.3 | 12466.2 | 12435.3 | 0.504 | 5 | 0.51 | 5.06 | 99.4 |
| | FNE-1, 25° C. | 6.0 | 12091.9 | 12016.5 | 12054.2 | 0.497 | 5 | 0.49 | 4.98 | 97.7 |

TABLE 17

| | | FNE-1 Actuation doses | | | |
|---|---|---|---|---|---|
| | | Actuation Dose (mg) per 100 ul spray | | | |
| Sample | 1st | 2nd | 3rd | Average | |
| FNE-1, 2-8° C., 1 week | 113 | 118 | 127 | 119 | |
| FNE-1, 25° C., 1 week | 121 | 119 | 125 | 122 | |
| FNE-1, 2-8° C., 2 weeks | 99 | 107 | 95 | 100 | |
| FNE-1, 25° C., 2 weeks | 110 | 120 | 123 | 118 | |
| FNE-1, 2-8° C., 4 weeks | 121 | 113 | 115 | 116 | |
| FNE-1, 25° C., 4 weeks | 100 | 92 | 100 | 97 | |

Example 6. Stability of Bumetanide Salts

The stability of the arginine and potassium bumetanide salts was monitored over a four week period with storage at either 2-8° C. or 25° C. for that time period. The bumetanide salt solutions were evaluated on the basis of pH, concentration of bumetanide in solution, the percent assay recovery and the presence of an impurity (see Tables 18 and 19).

TABLE 18

| | | Stability measurements of arginine bumetanide salt | | | | | |
|---|---|---|---|---|---|---|---|
| Measuring | T0 | 1 week | | 2 weeks | | 4 weeks | |
| pH | 7.0 | 5° C. | 25° C. | 5° C. | 25° C. | 5° C. | 25° C. |
| | | 7.0 | 7.1 | 7.0 | 7.0 | 7.0 | 7.1 |
| Assay (mg/mL) | 5.07 | 5° C. | 25° C. | 5° C. | 25° C. | 5° C. | 25° C. |
| | | 5.08 | 5.06 | 4.99 | 4.97 | 4.89 | 4.97 |
| Recovery (%) | 100.0 | 5° C. | 25° C. | 5° C. | 25° C. | 5° C. | 25° C. |
| | | 100.0 | 99.6 | 98.3 | 97.8 | 97.8 | 97.8 |
| Impurity | N/D* | 5° C. | 25° C. | 5° C. | 25° C. | 5° C. | 25° C. |
| | | N/D | N/D | N/D | N/D | N/D | N/D |

TABLE 18-continued

| | | | | | | |
|---|---|---|---|---|---|---|
| Stability measurements of arginine bumetanide salt | | | | | | |
| Measuring | T0 | 1 week | | 2 weeks | | 4 weeks |
| Osmolality (mOsm/kg) | 335 | 5° C. N/D | 25° C. N/D | 5° C. N/D | 25° C. N/D | 5° C. N/D | 25° C. N/D |
| Viscosity (cP) | 1.3 | 5° C. N/D | 25° C. N/D | 5° C. N/D | 25° C. N/D | 5° C. N/D | 25° C. N/D |

*N/D: not determined

TABLE 19

| | | | | | | |
|---|---|---|---|---|---|---|
| Stability measurements of potassium bumetanide salt | | | | | | |
| Measuring | T0 | 1 week | | 2 weeks | | 4 weeks |
| pH | 7.0 | 5° C. 7.0 | 25° C. 7.0 | 5° C. 7.0 | 25° C. 7.1 | 5° C. 7.0 | 25° C. 7.1 |
| Assay (mg/mL) | 5.10 | 5° C. 5.18 | 25° C. 5.10 | 5° C. 4.97 | 25° C. 4.96 | 5° C. 5.00 | 25° C. 5.03 |
| Recovery (%) | 100.0 | 5° C. 101.5 | 25° C. 100.0 | 5° C. 97.4 | 25° C. 97.2 | 5° C. 97.9 | 25° C. 98.6 |
| Impurity | N/D* | 5° C. N/D | 25° C. N/D | 5° C. N/D | 25° C. N/D | 5° C. N/D | 25° C. N/D |
| Osmolality (mOsm/kg) | 317 | 5° C. N/D | 25° C. N/D | 5° C. N/D | 25° C. N/D | 5° C. N/D | 25° C. N/D |
| Viscosity (cP) | 1.3 | 5° C. N/D | 25° C. N/D | 5° C. N/D | 25° C. N/D | 5° C. N/D | 25° C. N/D |

*N/D: not determined

For the arginine bumetanide salt, the initial pH was 7.0 and after four weeks was 7.0 and 7.1 for the sample stored at 5° C. and 25° C. respectively. The concentration of bumetanide in solution was initially found to be 5.07 mg/mL, and after four weeks, the concentrations were 4.89 and 4.97 mg/ml for the sample stored at 5° C. and 25° C. respectively. The percent assay recovery was initially 100% and after four weeks was 97.8% for both the sample stored at 5° C. and 25° C. Lastly, no impurity was detected initially or after four weeks for either sample as detected by HPLC. 10 These data demonstrate that the arginine bumetanide salt is stable for up to four weeks at either 5° C. or 25° C., as shown in Table 18. Additionally, the data demonstrate that the potassium bumetanide salt is stable for up to four weeks at either 5° C. or 25° C., as shown in Table 19.

Example 7. Method for Formulation of the Pharmaceutical Formulation of the Arginine Salt of Bumetanide, Potassium Salt of Bumetanide, and Lysine Salt of Bumetanide The pharmaceutical formulation of the arginine salt of bumetanide for intranasal administration to patients suffering from congestive heart failure was prepared by first dissolving 0.1 g of sodium carboxymethyl cellulose in 100 mL of deionized water and mixing to result in a 0.1% sodium carboxymethyl cellulose solution, which was filtered through a 0.2 μm nylon filter. Mannitol, benzyl alcohol, and 98.3% bumetanide was weighed out to 4 g, 0.5 g, and 0.5 g respectively and mixed. To this mixture, about 16 g of the 0.1% sodium carboxymethyl cellulose solution was added. To this solution, 0.45 g L-arginine was added and mixed using a vortex until the solution becomes clear. The pH of the solution is then adjusted using 1.0 N HCl to reach a final pH of 7.0. The formulation for the arginine salt of bumetanide at both a 1 g and 20 g scale were recorded in Table 20.

TABLE 20

| | | | |
|---|---|---|---|
| Formulation for the arginine salt of bumetanide | | | |
| | | | F69 |
| Excipient | mg/g | 20 g Batch amount (mg) | |
| 98.3%, Bumetanide | 5.0 | 101.72 | |
| Sodium CMC (low viscosity) | 1.0 | 20 | |
| Benzyl Alcohol | 5.0 | 100 | |
| L-Arginine | 4.5 | 90 | |
| Mannitol | 40.0 | 0.8 g | |
| Adjust pH with 1.0N HCl to 7.0 | | | |
| 0.1% CMC-Na | QS* | 20.0 g | |

*QS: quantum sufficit

TABLE 21

| | | | | | | |
|---|---|---|---|---|---|---|
| Formulation composition and compounding table for 10 g batch of arginine salt of bumetanide, potassium salt of bumetanide, and lysine salt of bumetanide | | | | | | |
| | F42 | | F43 | | F44 | |
| Excipient | mg/g | 10 g Batch amount (g) | mg/g | 10 g Batch amount (g) | Mg/g | 10 g Batch amount (g) |
| Bumetanide | 5.0 | 0.05 | 5.0 | 0.05 | 5.0 | 0.05 |
| Sodium CMC (low viscosity) | 1.0 | 0.01 | 1.0 | 0.01 | 1.0 | 0.01 |
| EDETATE DISODIUM dihydrate | 1.0 | 0.01 | 1.0 | 0.01 | 1.0 | 0.01 |
| L-Arginine | 4.5 | 0.045 | 0 | 0 | 0 | 0 |
| 1N KOH | 0 | 0 | 20 | 0.2 | 0 | 0 |
| L-Lysine | 0 | 0 | 0 | 0 | 4.0 | 40 |

TABLE 21-continued

Formulation composition and compounding table for 10 g batch of arginine salt of bumetanide, potassium salt of bumetanide, and lysine salt of bumetanide

| | F42 | | F43 | | F44 | |
|---|---|---|---|---|---|---|
| Excipient | mg/g | 10 g Batch amount (g) | mg/g | 10 g Batch amount (g) | Mg/g | 10 g Batch amount (g) |
| Adjust pH with 1.0N HCl to 7.0 | | | | | | |
| 0.1% CMC-Na Q.S. to | QS | 10.0 | QS | 10.0 | QS | 10.0 |

TABLE 22

Characterization of Arginine and Potassium Salts of Bumetanide

| Sample | Solubility of Bumetanide (mg/mL) | pH | Osmolality (mOsm/kg) | Viscosity |
|---|---|---|---|---|
| F42 | 4.92 | 6.7 | 279 | N/D |
| F43 | 5.04 | 7.0 | 268 | N/D |

A 10 g batch of the arginine salt of bumetanide (F42), potassium salt of bumetanide (F43), and lysine salt of bumetanide (F44) for intranasal administration to patients suffering from congestive heart failure were formulated according to Table 21. To a 250 ml beaker, 0.1 g of sodium CMC was added with stirring bar, and 100 mL of DI-water was added and mix well to get a 0.1% CMC-Na solution. Bumetanide and edetate disodium dihydrate were weighed out into a 15 mL tared falcon tube. To the tube, about 8 g of 0.1% CMC-Na solution was added and mixed. To this solution the amount of arginine, KOH, or lysine as described in Table 21 was added and mixed with a vortex until the solution became clear. Add appropriate amount of base, mix with vortex till get clear solution. At this point the pH was measured and adjusted to pH 7.0 if necessary. The 0.1% CMC-Na solution to a total weight of 10 g and mixed well. About 1 mL of solution was used to test osmolality. The osmolality was adjusted if need to about 290±10 mOsm/kg with either NaCl or mannitol. After the osmolality was adjusted, an assay and impurity analysis were performed, and the solution was measured for the viscosity and spray ability. The measure of solubility, pH, and osmolality are summarized in Table 22.

TABLE 23

Formulation composition and compounding table for arginine salt of bumetanide (F69) and potassium salt of bumetanide (F70)

| | F69 | | F70 | |
|---|---|---|---|---|
| Excipient | mg/g | 100 g Batch amount (mg) | mg/g | 100 g Batch amount (mg) |
| 98.3%, Bumetanide | 5.0 | 508.60 | 5.0 | 508.60 |
| Sodium CMC (low viscosity) | 1.0 | 100 | 1.0 | 100 |
| Benzyl Alcohol | 5.0 | 500 | 5.0 | 500 |
| L-Arginine | 4.5 | 450 | 0 | 0 |
| 1N KOH | 0 | 0 | 20.0* | 2000 |
| Mannitol | 40.0 | 4000 | 40.0 | 4000 |
| Adjust pH with 1.0N HCl to 7.0 | | | | |
| 0.1% CMC-Na | QS | 100.0 g | QS | 100.0 g |

*0.78 mg/g of K+ equivalent

A 100 g batch of the arginine salt of bumetanide (F69) and potassium salt of bumetanide (F70) for intranasal administration to patients suffering from congestive heart failure were formulated according to Table 23. Into a 500 ml beaker, 0.3 g of sodium CMC was added with a stirring bar. 300 mL of DI-water was added and mixed well to get 0.1% CMC-Na solution. The mixture was then filtered through a 0.2 μm nylon filter.

For the arginine salt of bumetanide (F69), bumetanide, benzyl alcohol and mannitol were weighed out in a 125 mL tared Erlenmeyer flask with stir bar. To the flask, about 75 g of 0.1% CMC-Na solution was added and mixed. The appropriate amount of L-arginine was added, and the solution was mixed with vortex until the solution became clear. At this point, the pH was measured and adjusted to pH to 7.0 if necessary. An amount of 0.1% CMC-Na solution was added to bring the total weight to 100 g, and the solution was mixed well.

For the potassium salt of bumetanide (F70), sodium CMC was weighed out into a suitable beaker with stirring to which a volume of DI-water was added, and the solution was mixed well to generate a 0.1% CMC-Na solution. This solution was then filtered through a 0.2 μm nylon filter. Bumetanide, benzyl alcohol, and mannitol were then weighed out and added to a primary formulation container with stirring. To this container about ¾ ths of the 0.1% CMC-Na was added and mixed or stirred. To this solution, an appropriate amount of 1N KOH was titrated slowly in and mixed with stirring, until the solution became clear. The clear solution was allowed to equilibrate to until a steady pH was achieved at the pH range of 6.3 to 7.3. The pH was then measured and re-adjusted to 7.0 if it was necessary using 1N HCl. Enough of the 0.1% CMC-Na solution was added and mixed well to bring the solution to the appropriate weight. The osmolality was measured in order to check that is was in the specified range.

Both F69 and F70 were filtered through a 0.2 μm nylon filter. 3 mL of each solution were aliquoted to a 10 mL nasal spray bottle for total 10 bottles. One vial of each formulation was used to perform an appearance, a pH, an assay/impurity, an osmolality, and an actuation dose test the results of which are summarized in Table 24.

TABLE 24

Characterization of F69 and F70

| ID | Appearance | pH | Assay (mg/g) | Impurity | Actuation dose (mg) (n = 3) per 100 μl spray | Osmolality (mOsm/kg) |
|---|---|---|---|---|---|---|
| F69 | Clear colorless solution | 7.0 | 4.98 | ND | 116.1 | 333 |
| F70 | Clear colorless solution | 7.0 | 4.89 | ND | 113.6 | 321 |

ND: not detected

Example 8. Characterization of Lead Formulations Over 5 Months

The arginine salt of bumetanide (F69), potassium salt of bumetanide (F70), bumetanide emulsion (FE-9), and bumetanide nano-emulsion (FNE-1) were examine for stability over a period of 5 months stored at 25° C. One sample of F70 was observed for 10 months with the bottle open to test stability. The appearance of each of the samples was recorded and summarized in Table 25.

TABLE 25

| | | Appearance of formulations |
|---|---|---|
| Sample | Lot | Appearance |
| F69_5M_25° C. | 338-2-6 | Clear colorless liquid; same as T0 |
| F70_5M_25° C. | 338-2-2 | Clear colorless liquid; same as T0 |
| F70_10M_25° C. (opened bottle) | 338-2-2 | Clear colorless liquid; same as T0 |
| FE-9_5M_25° C. | 338-2-41 | opaque emulsion; same as T0 |

TABLE 25-continued

| | | Appearance of formulations |
|---|---|---|
| Sample | Lot | Appearance |
| FNE-1_5M_25° C. | 338-2-34 | Clear very light yellowish solution with no particles; same as T0 |

The concentration for each of these formulations was measured using HPLC analysis after 5 months at 25° C. and one sample of F69 stored for 10 months. The resulting concentrations are summarized in Table 26. Additionally, the assay recovery over either 5 months or 10 months was calculated (Table 27).

TABLE 26

| | | | | | | QS to | HPLC | Calculated | Conc. |
|---|---|---|---|---|---|---|---|---|---|
| | | PA of | PA of | Average | Sample | Volume | conc. | conc. | at T0 |
| Sample | Lot | Inj. 1 | Inj. 2 | PA | Size (g) | (mL) | (mg/mL) | (mg/g) | (mg/g) |
| F69_5M | 338-2-6 | 12185.7 | 12170.2 | 12177.95 | 0.498 | 5 | 0.511 | 5.13 | 4.98 |
| F70_5M | 338-2-2 | 12271.9 | 12194.7 | 12233.3 | 0.497 | 5 | 0.513 | 5.16 | 4.89 |
| FE-9_5M | 338-2-41 | 11100.7 | 11055.2 | 11077.95 | 0.498 | 5 | 0.465 | 4.67 | 4.59 |
| FNE-1_5M | 338-2-34 | 11590.1 | 11619.3 | 11604.7 | 0.504 | 5 | 0.487 | 4.83 | 5.09 |
| F70_10M | 338-2-2 | 12734.9 | 12707.4 | 12721.15 | 0.503 | 5 | 0.524 | 5.21 | 4.89 |

Concentration stability of formulations

TABLE 27

Assay recovery vs T0

| | | | | Assay | % claim |
|---|---|---|---|---|---|
| | | | Assay | recovery | of 5 |
| | | Assay | at 5M | at 5M | mg/mL |
| | | at T0 | or 10M | or 10M | (Target |
| Sample | Lot | (mg/mL) | (mg/mL) | vs T0 (%) | 95-105%) |
| F69_5M_25° C. | 338-2-6 | 4.98 | 5.13 | 103.01 | 103% |
| F70_5M_25° C. | 338-2-2 | 4.89 | 5.16 | 105.52 | 103% |
| F70_10M_25° C. | 338-2-2 | 4.89 | 5.21 | 106.53 | 104% |
| FE-9_5M_25° C. | 338-2-41 | 4.59 | 4.67 | 101.74 | 93.4% |
| FNE-1_5M_25° C. | 338-2-34 | 5.09 | 4.83 | 94.89 | 102% |

The compositions of the potassium salt of bumetanide formulations are summarized in Table 28 along with each formulation's measured pH, appearance, osmolality, and assay recovery.

TABLE 28

Formulation composition and compounding potassium salt of bumetanide formulation of F70 at 10, 15 and 16.5, 18 and 20 mg/mL bumetanide strengths

| | | % w/w | | | | | |
|---|---|---|---|---|---|---|---|
| Ingredient | Function | F79 | F80 | F81 | F82 | F83 | F84 |
| Bumetanide USP | API | 1 | 1.5 | 2 | 1 | 1.5 | 1.8 |
| Sodium CMC (low viscosity) USP | Viscosity control agent | 0.1 | 0.1 | 0.1 | 0.1 | 0.1 | 0.1 |
| Benzyl Alcohol NF | Preservative | 0.5 | 0.5 | 0.5 | 0.5 | 0.5 | 0.5 |
| 1N KOH ACS | pH modifier and adjust pH | 4 | 6 | 8 | 4 | 6 | 8 |

TABLE 28-continued

| Formulation composition and compounding potassium salt of bumetanide formulation of F70 at 10, 15 and 16.5, 18 and 20 mg/mL bumetanide strengths | | | | | | | |
|---|---|---|---|---|---|---|---|
| Mannitol USP | Tonicity Agent | 4 | 4 | 4 | 2.5 | 2 | 2 |
| Water for Injection USP | Medium | 90.4 | 87.9 | 85.4 | 91.9 | 89.9 | 87.6 |
| 1N HCl, ACS, USP, EP | pH adjustment agent | 6.8 | 6.9 | 7.5 | 7.2-7.4 | 7.2 -7.4 | 7.2 -7.5 |

| Assay, pH and Osmolality: | | | |
|---|---|---|---|
| ID | F79 | F80 | F81 |
| Assay After $1^{st}$ filtration, mg/ml | 10.5 | 15.3 | 19.7 |
| Assay After $3^{rd}$ filtration, mg/ml | 10.1 | 14.9 | 19.6 |
| pH (Before filtration) | 6.69 | 6.79 | 7.54 |
| pH (After $3^{rd}$ filtration) | 6.78 | 6.86 | 7.51 |
| Osmolality (After $1^{st}$ filtration) (mOsm/Kg) | 378 | 420 | 418 |

| Assay, pH, and osmolality: | | | |
|---|---|---|---|
| ID | F82 | F83 | F84 |
| pH (Before filtration) | 7.35 | 7.34 | 7.47 |
| pH (After filtration and overnight @ 2-8° C.) | 7.02 | 7.22 | 7.25 |
| Osmolality (After filtration) (mOsm/Kg) | 286 | 325 | 352 |
| Assay After filtration (0.22 μm) (mg/ml) | 9.80 | 14.18 | 16.58 |

Particle size distribution analysis was performed to determine the average particle size tor the HE-9 and FNE-1 bumetanide emulsions was measured using dynamic light scattering on a Malvern Panalytical Zetasizer. The average particle sizes for FE-9 and FNE-1 stored at room temperature over a period of 5 months are described in Table 29.

TABLE 29

| Particle size analysis FE-9 and FNE-1 emulsions | | | | | | |
|---|---|---|---|---|---|---|
| Sample Name | T (° C.) | Z-Ave (d.nm) | Pdl | D (v, 0.1) | D (v, 0.5) | D (v, 0.9) |
| FE-9_T0 | 25 | 112.0 | 0.173 | 41.4 | 74.8 | 227.0 |
| FE-9_5M 25° C. | 25 | 129.9 | 0.106 | 61.5 | 103 | 254 |
| FNE-1_1W | 25 | 11.3 | 0.609 | 1.0 | 1.4 | 2.2 |
| FNE-1_5M 25° C. | 25 | 5.7 | 0.314 | 1.3 | 1.9 | 3.6 |

At 25° C. storage condition, the assay for F69 after 5 months showed a concentration of 5.13 mg/g, which was close to the TO assay, which was 4.98 mg/g. The assay for F70 after 5 months showed a concentration of 5.16 mg/g, which was close to the TO assay, which was 4.89 mg/g. After 10 months, the assay of F70 showed a concentration of 5.21 mg/g, which was close to the TO assay, which is 4.89 mg/g. After 10 months the assay recovery for F70 was about 106.5% compared to T0. This may have been due to the fact that the sample was sampled from an opened container (previously used) and which may account for the loss of water over time when it was stored at 25° C., The % claim value after 10M at storage at RT was 104%. The assay of FE9 after 5 months measured a concentration of 4.67 mg/g, which was close to the TO assay, which was 4.59 mg/g. The assay of FNE-1 was measured as 4.83 mg/g, which was close to the TO assay, which was 5.09 mg/g. No impurities were observed in all 4 formulations when they were stored at 25° C. for 5 months. At 25° C. for 5 months, for F69, F70, FE-9, and FNE-1 formulations, the assay recoveries vs TO were all more than 94%. Particles, precipitation, and phase separation were not observed in all 4 formulations. These data indicate that all four formulations were stable for 5 months when they were stored at 25° C. Additionally, after 5 months, the particle size distributions of both FE-9 and FNE-1 were close to that of TO or T=1W.

Example 9. Administration of an Intranasal Arginine or Potassium Salt of Bumetanide to a Patient Suffering Congestive Heart Failure with Severe Edema Caused Inadequate Gastrointestinal Absorption According to the methods described herein, a physician of skill in the art can treat a patient, such as a human patient, so as to reduce or alleviate symptoms of edema arising from congestive heart failure. To this end, a physician of skill in the art has the patient administer to themselves a potassium or arginine salt of bumetanide. The potassium or arginine salt of bumetanide is administered by the patient experiencing symptoms of congestive heart failure such as shortness of breath, fatigue or edema that not reduced with the patient's typical daily dosage of an oral diuretic. At this time, the patient administers the potassium or arginine salt of bumetanide intranasally. Typical dosages are administered based on body weight, and are in the range of about 0.5-10 mg of the potassium or arginine salt of bumetanide over a 12 hour period, and not exceeding 10 mg of the potassium or arginine salt of bumetanide over a 12 hour period without consulting a physician of skill in the art.

The potassium or arginine bumetanide salt is administered in one, two, three or four doses over a 4 hour period. Each dose consists of 100-150 μL of buffer containing the potassium or arginine bumetanide salt at a concentration of about 5-25 mg/mL. Each unit dose contains about 0.5-2.5 mg of the potassium or arginine bumetanide salt, such that four doses do not exceed 10 mg of the pharmaceutical composition. The potassium or arginine bumetanide salt is administered to the patient in an amount sufficient to treat the symptoms of congestive heart failure as is self-evaluated by the patient, including reduction of swelling, increase urine output and reduced shortness of breath. The intranasal pharmaceutical composition is administered by the patient who maintains a supine position for at least 30 minutes after the administration of the pharmaceutical composition.

Example 10. Extended Release Formulation for Subcutaneous Administration

The methods and compositions described herein can provide a subcutaneously administered formulation that releases bumetanide to a patient for an extended period of time (e.g., 8 hours, 12 hours, 24 hours, 36 hours, 48 hours, 3 days, or 5 days of diuresis) as a long acting diuretic. The extended release formulation is used to treat a patient at risk for rehospitalization after treatment for congestive heart failure. The use of the long acting diuretic permits such patients to be treated on an outpatient basis, rather than undergo rehospitalization for edema-related symptoms. The extended release formulation is administered as a subcutaneous depot (e.g., a depot formed by an emulsion), which is released from the subcutaneous depot over an extended period of time.

The extended release formulation is formed from an aqueous emulsion of arginine bumetanide salt at a bumetanide concentration of about 7 to 15 mg/mL. Each dose consists of about 100-300 UL of the aqueous emulsion, and the dosing level may be determined by the body weight and health status of the patient. The emulsion is a mixture of formed from glycerol (ca. 2.25% weight), medium chain triglycerides (MCT) (ca. 10% weight) and lecithin (E-80) (ca. 1.2% weight).

The subcutaneous administration of the depot formulation allows the patient to benefit from a reliable diuretic effect over a period of days without complications. As a result of the extended release subcutaneous formulation of the arginine bumetanide emulsion, a patient at risk of rehospitalization following hospitalization for the treatment of congestive heart failure, receives treatment after discharge from the hospital, such that diuresis is achieved and symptoms such as shortness of breath, fatigue, and edema are relieved for an extended period of time.

Example 11. Preparation of Bumetanide Salts

The arginine bumetanide salt was prepared by adding 1.00 g of bumetanide and 0.53 g arginine to a motor. To the arginine and bumetanide in the motor, about 15 mL of 200 proof ethanol diluted 50% with deionized water was added. A slurry was made by granulating manually with a pestle for about 30 minutes. The resulting slurry was transferred to a tared beaker. The slurry was then dried under vacuum at −20° C. overnight. After more than 24 hours drying under vacuum, a loose, fluffy white solid was obtained with a molar ratio of 1:1.1 bumetanide to arginine, as described in Table 31. All chemicals used in generating the arginine bumetanide salt are described in Table 30.

TABLE 30

| Description of Chemicals Used in Arginine Bumetanide Salt Preparation | | | |
|---|---|---|---|
| Description | Grade | Supplier | Lot |
| Bumetanide | N/A | CAYMAN CHEMICAL | 0472995.21 |
| Arginine | USP | Spectrum | 1EG0013 |
| Ethanol 200 proof | USP | Decon Lab, Inc. | 256915 |
| DI-H2O | N/A | Latitude | N/A |

TABLE 31

| Ratio of Bumetanide to Arginine | | | | |
|---|---|---|---|---|
| Description | Weight (g) | MW (g/mol) | Molar (M) | Molar ratio |
| Bumetanide | 1.00 | 364.417 | 0.00192 | 1:1.1 |
| Arginine | 0.53 | 174.200 | 0.00213 | |

The potassium bumetanide salt was prepared by adding 1.0 g of bumetanide to a 20 mL glass vial. To the glass vial, 5 mL of a 200 proof ethanol solution diluted by 50% with deionized water was added and vortexed to mix for about 1 minute. To the wet bumetanide, 3.0 mL of 1 N KOH solution was added and mixed with a vortex or a spatula for about 10 minutes resulting in a white slurry. The mixture was frozen for about 1 hour at −20° C. The mixture was then dried under vacuum overnight at −20° C. Once dried, the white, fluffy soft solid potassium bumetanide, having a molar ratio of 1:1.1 bumetanide to potassium as described in Table 33, was transferred to a clean glass vial. The potassium bumetanide salt was reserved at 2-8° C. for formulation preparation. All chemicals used in generating the potassium bumetanide salt are described in Table 32.

TABLE 32

| Description of Chemicals Used in Potassium Bumetanide Salt Preparation | | | |
|---|---|---|---|
| Description | Grade | Supplier | Lot |
| Bumetanide | N/A | CAYMAN CHEMICAL | 0472995.21 |
| 1.0N KOH | USP | Spectrum | 1EG0013 |
| Ethanol 200 proof | USP | Decon Lab., Inc | 256915 |
| DI-H2O | N/A | Latitude | N/A |

TABLE 33

| Ratio of Potassium to Arginine | | | | |
|---|---|---|---|---|
| Description | Weight (g) | MW | Molar | Molar ratio |
| Bumetanide | 1.0 | 364.417 | 0.0027 | 1:1.11 |
| 1N KOH | 3.0 | 56.11 | 0.0030 | |

Example 12. Effect of Intranasal and Intravenous Administration of Bumetanide Salts to Rabbits The purpose of this study was to assess the pharmacokinetic profiles of a formulation of bumetanide compound, including arginine salt of bumetanide F69, potassium salt of bumetanide F70 a bumetanide emulsion FE-9, and a bumetanide nano-emulsion FNE-1, as described in Table 34, when administered as a single intranasal dose in four formulations in different vehicles when compared to being administered as a single IV dose in male and female New Zealand white (NZW) rabbits.

TABLE 34

| | Intranasal Formulation Components | |
|---|---|---|
| Formulation | Ingredients | Formulation Type |
| F69 | Bumetanide, Sodium CMC (low viscosity), L-Arginine (base), Mannitol, Benzyl alcohol, HCl (acid), DI Water (pH 7.0) | Aqueous solution |
| F70 | Bumetanide, Sodium CMC (low viscosity), KOH (K+ base), Mannitol, Benzyl alcohol, HCl (acid), DI Water (pH 7.0) | Aqueous solution |
| FE-9 | Bumetanide, MCT (medium chain triglyceride), Lecithin (E-80), Polysorbate 80, Glycerol, NaOH (base), Benzyl alcohol, HCl (acid), DI water (pH 6.1) | Emulsion |
| FNE-1 | Bumetanide, Soy lecithin (PL90G), Glycocholic acid, Benzyl alcohol, NaOH (base), Dextrose, HCl (acid), DI water (pH 6.1) | Nano-emulsion |

A total of 8 rabbits were assigned to the study (6 males and 2 females). The rabbits were all young adults of uniform age and with weight uniform as possible (approximately 3.0 to 3.6 kg at the initiation of dosing).

Because bumetanide is a diuretic, 30 minutes prior to dosing with the bumetanide compound, the rabbits received an injection of 40 mL of Lactated Ringer's solution subcutaneously (SQ) for all events. The injection of 40 mL of Lactated-Ringer's solution was repeated 2 hours post-dose.

Dosing events with the various bumetanide formulations were staggered and rabbits were allowed to recover for ~7 days between each of the events described in Table 35.

For intranasal administration, each rabbit was be held in a supine position and administered 50 μL/nostril of a formulation of bumetanide was delivered into each nostril using a displacement pipette for a total of 100 μL/rabbit. The rabbits were held in a supine position for ~60 seconds after dosing. After each application, successful dosing was verified by visual inspection of the pipette tip and the rabbit nostril. Only administrations estimated to at least 80% of the bumetanide formulation was considered acceptable.

For intravenous administration, an injection of the commercially available bumetanide (Walgreens, 0.25 mg/mL)

was used and administered via the marginal ear vein over a period of 30 seconds for a total volume of 2 mL/rabbit.

Detailed clinical observations were conducted at least once daily and whenever an abnormality was observed. Nostrils were observed for any adverse signs post-dose. Additional cage-side observations were conducted by animal care at least once daily. Additionally, urine volume was monitored post-dose to assess diuresis by making observations at 30 min, 1 hour, and 2 hours post-dose. Urine volume was not measured.

Body weights were measured for each animal prior to each dose on the day of dose, and approximately 72 hours after the last dose. Body weights were provided for pharmacokinetic analysis. On each day of dosing, 600 μL of blood was collected from the central ear artery catheter in an uncoated polypropylene tube to obtain serum at the timepoints of before dosing, and 2±1 minutes, 5±1 minutes, 10±2 minutes, 15±2 minutes, 20±3 minutes, 30±3 minutes, 45±3 minutes, 60±4 minutes, 120±5 minutes, and 180±5 minutes after dosing. The blood sample was centrifuged at 5000×g for 10 minutes at 4° C. If the samples were collected outside collection window, they were not considered a protocol deviation; the collection time was provided for the purpose of pharmacokinetic analysis. Serum was stored frozen at −20° C. until shipped to Climax Laboratories, Inc. on dry ice by FedEx overnight shipping. The concentration of bumetanide in the serum samples was quantified by liquid chromatography coupled with tandem mass spectrometry detection (LC-MS/MS). The amount of bumetanide in each dosing regimen was quantified by liquid chromatography. The dosing regimen and calculated bioavailability of F69, F70, FE-9, FNE-1, commercially available bumetanide for IV administration are summarized in Tables 37-41 respectively. The bioavailability for each intranasal formulation is summarized in Table 36.

TABLE 35

| | Description of Bumetanide Dosing Events | | | | |
|---|---|---|---|---|---|
| Event | Formulation | Dose Route | Dose Level (mg/ rabbit) | Dose Volume | Dose Concentration (mg/g or mg/mL) |
| 1 | IV Injection | IV | 0.5 | 2.0 mL | 0.25 mg/mL |
| 2 | F69 | Intra-nasal | 0.5 | 50 μL/ nostril | 5 mg/mL |
| 3 | F70 | Intra-nasal | 0.5 | 50 μL/ nostril | 5 mg/mL |
| 4 | FE-9 | Intra-nasal | 0.5 | 50 μL/ nostril | 5 mg/mL |
| 5 | FNE1 | Intra-nasal | 0.5 | 50 μL/ nostril | 5 mg/mL |

TABLE 36

| Bumetanide Serum Pharmacokinetic Parameters in Rabbits Given a Single Intranasal (IN) or Intravenous (IV) Dose of a Bumetanide Formulation | | | | | | | |
|---|---|---|---|---|---|---|---|
| Route | Formulation | $C_{max}$ (ng/ml) | $T_{max}$ (min) | $AUC_{0-t}$ (ng*h/mL) | Dose (mg) | Dose (mg/kg) | Bioavailability |
| IN | F69 | 54.2 | 5 | 40.2 | 0.513 | 0.162 | 21.5% |
| IN | F70 | 96.8 | 12.5 | 92.5 | 0.516 | 0.173 | 45.9% |
| IN | FE-9 | 42.3 | 5 | 51.2 | 0.467 | 0.140 | 31.1% |
| IN | FNE1 | 77.4 | 10 | 65.7 | 0.483 | 0.140 | 39.5% |
| IV | Solution | — | — | 199 | 0.500 | 0.171 | — |

Values are mean of 4 animals in each group, other than $T_{max}$, which is the median of 4 animals

TABLE 37

Bumetanide Serum Concentrations and Pharmacokinetic Parameters in Rabbits Administered
a 2 × 50 μL Intranasal Dose of Formulation F69

| | Animal ID, Sex, Serum Concentration (ng/ml) and PK Parameters | | | | | |
|---|---|---|---|---|---|---|
| Time (min) | 1502 Female | 1004 Male | 1005 Male | 1006 Male | Mean* | SD |
| 0 (predose) | BQL | BQL | BQL | BQL | BQL | — |
| 2 | 59.8 | 24.1 | 21.4 | 25.2 | 32.6 | 18.2 |
| 5 | 126 | 23.4 | 24.6 | 27.8 | 50.5 | 50.4 |
| 10 | 117 | 14.5 | 22.1 | 23.2 | 44.2 | 48.7 |
| 15 | 92.9 | 19.2 | 38.9 | 14.4 | 41.4 | 36.0 |
| 20 | 71.4 | 14.6 | 25.9 | 12.7 | 31.2 | 27.5 |
| 30 | 36.4 | 4.45 | 8.89 | 8.46 | 14.6 | 14.7 |
| 45 | 17.7 | 7.98 | 15.0 | 11.4 | 13.0 | 4.24 |
| 60 | 20.4 | 3.63 | 8.46 | 6.7 | 9.80 | 7.34 |
| 120 | 9.75 | 2.11 | 9.72 | 10.6 | 8.05 | 3.98 |
| 180 | 16.1 | 3.26 | 8.51 | 4.28 | 8.04 | 5.84 |
| $C_{max}$ (ng/mL) | 126 | 24.1 | 38.9 | 27.8 | 54.2 | 48.3 |
| $T_{max}$ (min) | 5 | 2 | 15 | 5 | 5 | |
| $AUC_{0-t}$ (ng*min/mL) | 4792 | 968 | 2143 | 1750 | 2413 | 1659 |
| $AUC_{0-t}$ (ng*h/mL) | 79.9 | 16.1 | 35.7 | 29.2 | 40.2 | 27.7 |
| Weight (kg) | 3.25 | 3.10 | 3.03 | 3.29 | 3.17 | 0.123 |
| Dose (mg) | 0.513 | 0.513 | 0.513 | 0.513 | 0.513 | |
| Dose (mg/kg) | 0.158 | 0.165 | 0.170 | 0.156 | 0.162 | 0.006 |
| DA $AUC_{0-t}$ (ng*h/mL)/(mg/kg) | 506 | 98.0 | 211 | 187 | 250 | 177 |
| Bioavailability | 43.4% | 8.4% | 18.1% | 16.0% | 21.5% | 15.2% |

*Median for $T_{max}$, DA = Dose Adjusted

TABLE 38

Bumetanide Serum Concentrations and Pharmacokinetic Parameters in Rabbits Administered
a 2 × 50 uL Intranasal Dose of Formulation F70

| | Animal ID, Sex, Serum Concentration (ng/ml) and PK Parameters | | | | | |
|---|---|---|---|---|---|---|
| Time (min) | 1501 Female | 1001 Male | 1002 Male | 1003 Male | Mean* | SD |
| 0 (predose) | BQL | BQL | BQL | BQL | BQL | — |
| 2 | 52.1 | 24.0 | 63.5 | 35.5 | 43.8 | 17.5 |
| 5 | 148 | 68.3 | 95.0 | 31.8 | 85.8 | 48.9 |
| 10 | 45.4 | 84.7 | 91.1 | 53.4 | 68.7 | 22.6 |
| 15 | 35.0 | 70.4 | 63.1 | 24.9 | 48.4 | 21.8 |
| 20 | 32.9 | 87.5 | 59.1 | 16.8 | 49.1 | 31.0 |
| 30 | 22.8 | 82.0 | 49.4 | 24.2 | 44.6 | 27.8 |
| 45 | 12.9 | 48.0 | 37.6 | 27.0 | 31.4 | 15.0 |
| 60 | 67.9 | 19.0 | 35.9 | 6.3 | 32.3 | 26.7 |
| 120 | 5.46 | 7.42 | 21.7 | 56.7 | 22.8 | 23.7 |
| 180 | 13.7 | 28.3 | 17.8 | 12.0 | 18.0 | 7.32 |
| $C_{max}$ (ng/mL) | 148 | 87.5 | 95 | 56.7 | 96.8 | 37.9 |
| $T_{max}$ (min) | 5 | 20 | 5 | 120 | 12.5 | — |
| $AUC_{0-t}$ (ng*min/mL) | 5134 | 5517 | 6117 | 5440 | 5552 | 411 |
| $AUC_{0-t}$ (ng*h/mL) | 85.6 | 91.9 | 101.9 | 90.7 | 92.5 | 6.85 |
| Weight (kg) | 3.06 | 2.94 | 2.86 | 3.11 | 2.99 | 0.114 |
| Dose (mg) | 0.516 | 0.516 | 0.516 | 0.516 | 0.516 | — |
| Dose (mg/kg) | 0.169 | 0.175 | 0.181 | 0.166 | 0.173 | 0.007 |
| DA $AUC_{0-t}$ (ng*h/mL)/(mg/kg) | 507 | 524 | 564 | 546 | 535 | 25 |
| Bioavailability | 43.4% | 44.9% | 48.4% | 46.8% | 45.9% | 2.2% |

*Median for $T_{max}$, DA = Dose Adjusted

TABLE 39

Bumetanide Serum Concentrations and Pharmacokinetic Parameters in Rabbits Administered
a 2 × 50 uL Intranasal Dose of Formulation FE-9

| Time (min) | Animal ID, Sex, Serum Concentration (ng/ml) and PK Parameters | | | | | |
|---|---|---|---|---|---|---|
| | 1502 Female | 1004 Male | 1005 Male | 1006 Male | Mean* | SD |
| 0 (predose) | BQL | 6.54 | BQL | BQL | BQL | — |
| 2 | 28.8 | 16.9 | 15.2 | 22.9 | 21.0 | 6.19 |
| 5 | 45.2 | 29.7 | 31.9 | 39.9 | 36.7 | 7.18 |
| 10 | 33.9 | 13.7 | 46.2 | 26.1 | 30.0 | 13.6 |
| 15 | 31.0 | 9.25 | 45.4 | 18.2 | 26.0 | 15.7 |
| 20 | 23.0 | 9.23 | 54.2 | 16.3 | 25.7 | 19.8 |
| 30 | 27.4 | 7.57 | 40.9 | 15.8 | 22.9 | 14.5 |
| 45 | 16.2 | 5.54 | 29.5 | 18.3 | 17.4 | 9.82 |
| 60 | 14.7 | 5.24 | 31.3 | 13.3 | 16.1 | 10.9 |
| 120 | 8.77 | 6.64 | 11.7 | 11.4 | 9.63 | 239 |
| 180 | 5.06 | 4.68 | 11.4 | 8.45 | 7.40 | 3.16 |
| 240 | 10.2 | 5.67 | 7.70 | 6.64 | 7.55 | 1.95 |
| $C_{max}$ (ng/mL) | 45.2 | 29.7 | 54.2 | 39.9 | 42.3 | 10.2 |
| $T_{max}$ (min) | 5 | 5 | 20 | 5 | 5 | — |
| $AUC_{0-t}$ (ng*min/mL) | 3022 | 1575 | 4775 | 2922 | 3073 | 1312 |
| $AUC_{0-t}$ (ng*h/mL) | 50.4 | 26.3 | 79.6 | 48.7 | 51.2 | 21.9 |
| Weight (kg) | 3.62 | 3.41 | 3.19 | 3.13 | 3.34 | 0.224 |
| Dose (mg) | 0.467 | 0.467 | 0.467 | 0.467 | 0.467 | — |
| Dose (mg/kg) | 0.129 | 0.137 | 0.146 | 0.149 | 0.140 | 0.009 |
| DA $AUC_{0-t}$ (ng*h/mL)/(mg/kg) | 391 | 192 | 544 | 326 | 363 | 146 |
| Bioavailability | 33.5% | 16.4% | 46.7% | 28.0% | 31.1% | 12.5% |

*Median for $T_{max}$, DA = Dose Adjusted

TABLE 40

Bumetanide Serum Concentrations and Pharmacokinetic Parameters in Rabbits
Administered a 2 × 50 μL Intranasal Dose of Formulation FNE-1

| Time (min) | Animal ID, Sex, Serum Concentration (ng/mL) and PK Parameters | | | | | |
|---|---|---|---|---|---|---|
| | 1501 Female | 1001 Male | 1002 Male | 1003 Male | Mean* | SD |
| 0 (predose) | BQL | BQL | BQL | BQL | BQL | — |
| 2 | 78.0 | 37.3 | 29.3 | 16.6 | 40.3 | 26.5 |
| 5 | 46.9 | 82.1 | 77.9 | 47.2 | 63.5 | 19.1 |
| 10 | 75.9 | 90.3 | 78.9 | 62.2 | 76.8 | 11.6 |
| 15 | 47.7 | 85.6 | 42.7 | 36.7 | 53.2 | 22.1 |
| 20 | 37.1 | 77.5 | 38.7 | 33.2 | 46.6 | 20.7 |
| 30 | 19.2 | 52.3 | 30.1 | 20.9 | 30.6 | 15.2 |
| 45 | 16.0 | 51.2 | 18.3 | 13.0 | 24.6 | 17.8 |
| 60 | 10.5 | 28.6 | 10.1 | 16.8 | 16.5 | 8.63 |
| 120 | 6.34 | 17.6 | 9.14 | 7.62 | 10.2 | 5.08 |
| 180 | 3.83 | 13.0 | 5.61 | 5.44 | 6.97 | 4.10 |
| 240 | 5.99 | 6.15 | 5.74 | 7.26 | 6.29 | 0.67 |
| $C_{max}$ (ng/mL) | 78.0 | 90.3 | 78.9 | 62.2 | 77.4 | 11.5 |
| $T_{max}$ (min) | 2 | 10 | 10 | 10 | 10 | — |
| $AUC_{0-t}$ (ng*min/mL) | 2943 | 6397 | 3370 | 3061 | 3943 | 1646 |
| $AUC_{0-t}$ (ng*h/mL) | 49.0 | 107 | 56.2 | 51.0 | 65.7 | 27.4 |
| Weight (kg) | 3.68 | 3.11 | 3.42 | 3.62 | 3.46 | 0.257 |
| Dose (mg) | 0.483 | 0.483 | 0.483 | 0.483 | 0.483 | — |
| Dose (mg/kg) | 0.131 | 0.155 | 0.141 | 0.133 | 0.140 | 0.011 |
| DA $AUC_{0-t}$ (ng*h/mL)/(mg/kg) | 374 | 687 | 398 | 382 | 460 | 151 |
| Bioavailability | 32.1% | 58.9% | 34.1% | 32.8% | 39.5% | 13.0% |

*Median for $T_{max}$, DA = Dose Adjusted

TABLE 41

Bumetanide Serum Concentrations and Pharmacokinetic Parameters in Rabbits Given a
0.5-mg IV Dose of Bumetanide

| | Animal ID, Sex, Serum Concentration (ng/mL) and PK Parameters | | | | | |
| Time (min) | 1501 Female | 1001 Male | 1002 Male | 1003 Male | Mean | SD |
|---|---|---|---|---|---|---|
| 0 (predose) | BQL | BQL | BQL | BQL | BQL | — |
| 2 | 1450 | 1620 | 1100 | 1620 | 1448 | 245 |
| 5 | 482 | 453 | 523 | 660 | 530 | 91.6 |
| 10 | 214 | 336 | 223 | 138 | 228 | 81.6 |
| 15 | 110 | 99.6 | 107 | 94.3 | 103 | 7.12 |
| 20 | 60.7 | 89.2 | 65.1 | 63 | 69.5 | 13.3 |
| 30 | 26.6 | 41.3 | 27.1 | 35 | 32.5 | 7.02 |
| 45 | 9.95 | 25.3 | 13.5 | 17.6 | 16.6 | 6.60 |
| 60 | 3.65 | 13.9 | 9.85 | 9.05 | 9.11 | 4.22 |
| 120 | 1.03 | 2.59 | 1.93 | 2.39 | 1.99 | 0.69 |
| 180 | 0.426 | 0.579 | 0.81 | 0.734 | 0.637 | 0.171 |
| $AUC_{0-t}$ (ng*min/mL) | 11343 | 14087 | 9837 | 12478 | 11936 | 1796 |
| $AUC_{0-t}$ (ng*h/mL) | 189 | 235 | 164 | 208 | 199 | 29.9 |
| Weight (kg) | 3.17 | 2.88 | 2.78 | 2.90 | 2.93 | 0.166 |
| Dose (mg) | 0.500 | 0.500 | 0.500 | 0.500 | 0.500 | — |
| Dose (mg/kg) | 0.158 | 0.174 | 0.180 | 0.173 | 0.171 | 0.009 |
| DA $AUC_{0-t}$ (ng*h/mL)/(mg/kg) | 1198 | 1351 | 912 | 1205 | 1167 | 184 |

DA = Dose Adjusted

Figure 2:
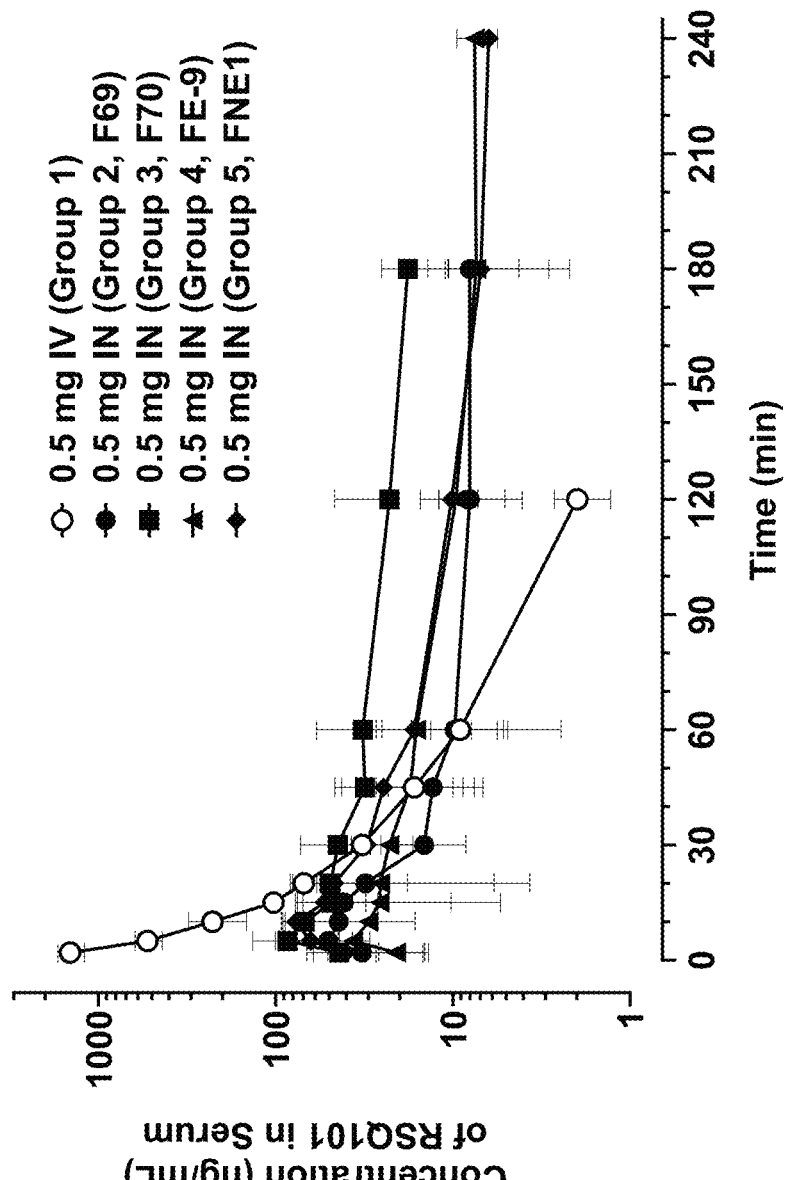
FIG. 2 is a graph showing the concentration (ng/ml) of bumetanide in the plasma of New Zealand White (NZW) rabbits over a period of 2 minutes to 240 minutes after intravenous (IV) administration of about 0.5 mg of commercially available bumetanide or intranasal (IN) of approximately 0.5 mg of a bumetanide compound including the arginine bumetanide salt formulation (F69), the potassium bumetanide salt formulation (F70), the bumetanide emulsion (FE-9), and the bumetanide nano-emulsion (FNE-1) on a logarithmic scale.
Figure 3:
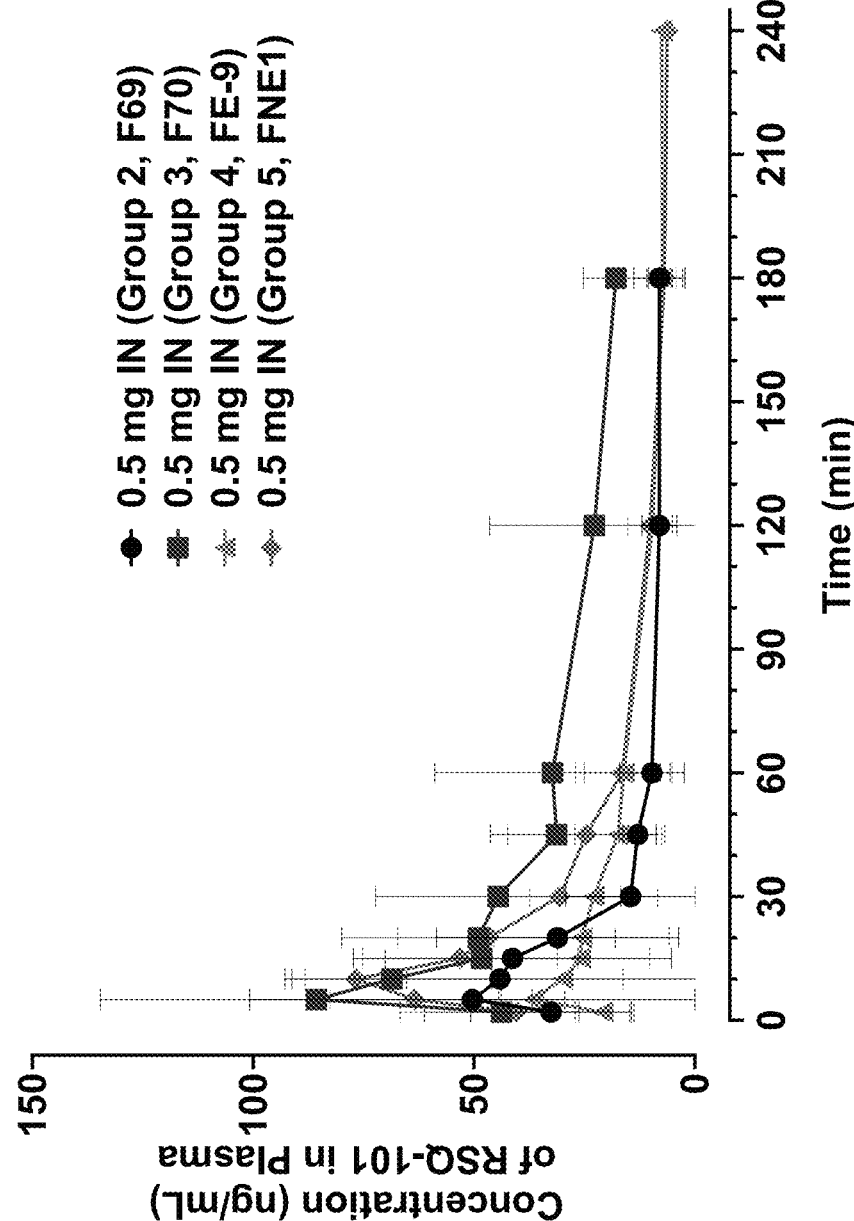
FIG. 3 is a graph showing the concentration (ng/ml) of bumetanide in the plasma of rabbits over a period of 2 minutes to 240 minutes after IN administration of 0.5 mg of the F69, F70, FE-9, or the FNE-1 bumetanide compound on a linear scale.
Figure 4:
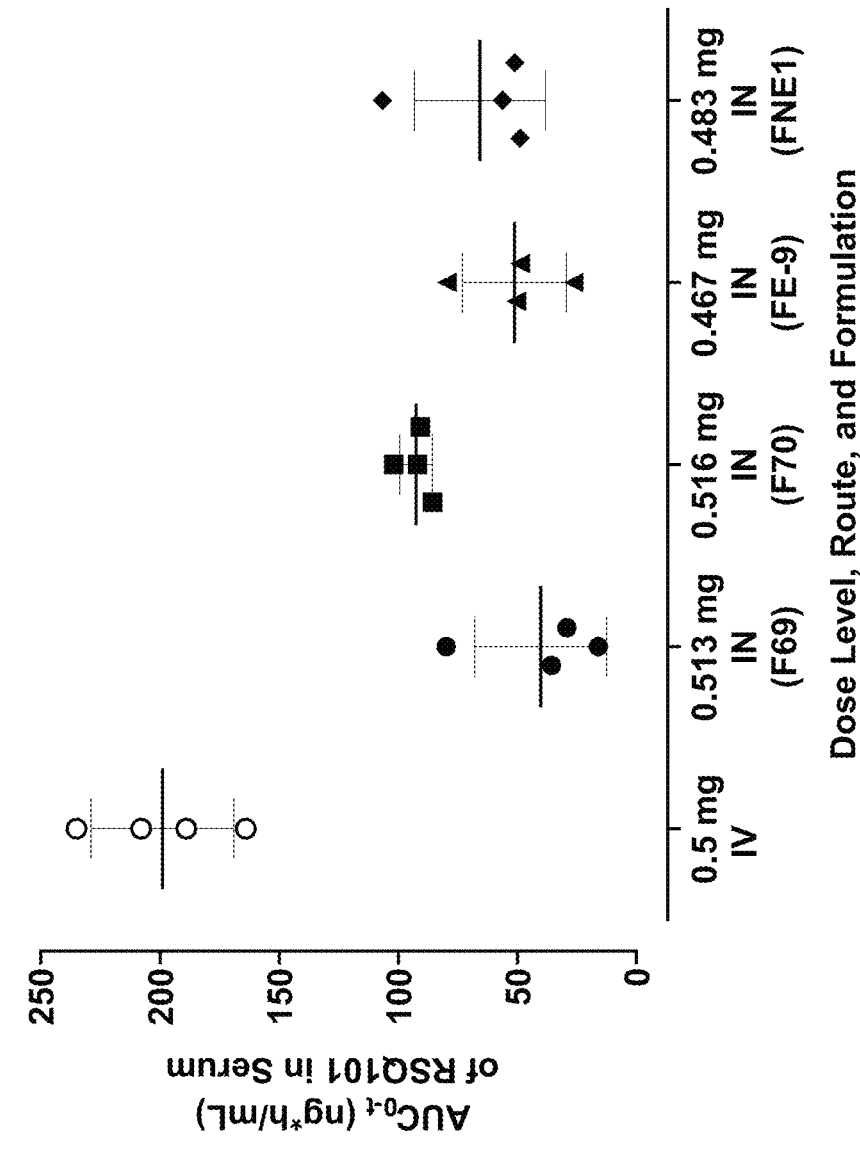
FIG. 4 is a graph showing the area under the curve (AUC) of the concentration of bumetanide in the plasma of rabbits over a time period of 2 to 240 minutes (ng*h/mL) after IV administration of about 0.5 mg of commercially available bumetanide or IN administration of approximately 0.5 mg of the F69, F70, FE-9, or the FNE-1 bumetanide formulations.

All the intranasal formulations were absorbed rapidly into systemic circulation in rabbits, with a median $T_{max}$ of 5 to 12.5 minutes after dosing. The potassium bumetanide salt formulation, F70, showed a greater nasal absorption of bumetanide than the arginine bumetanide formulation, F69, the bumetanide emulsion formulation, FE-9, or the bumetanide nano-emulsion formulation, FNE-1 as shown in FIGS. 2, 3, and 4 and Table 36. The bioavailability of bumetanide trended the same across the species tested. System exposure of F70 following intranasal administration is generally similar to intravenous administration in rabbits as shown in FIG. 2. The variability of bumetanide in the blood when F70 was administered intranasally is similar to the blood concentration level of bumetanide when administered intravenously. F70 showed rapid adsorption upon administration similar to what was observed when the bumetanide was administered intravenously as shown in FIG. 2. Intranasally administered bumetanide also showed persistent blood concentration levels as shown in FIGS. 2 and 3. All rabbits appeared normal during this study. There were no abnormal observations recorded of the nostrils for any animal or event. The formulations were well tolerated by the animals and did not result in death, morbidity, adverse clinical observations or body weight effects, or any visible tissue reactivity or inflammatory response. Animals treated with IV bumetanide and IN bumetanide formulations produced more urine through 2 hours post dose compared to untreated controls.

Example 13. Administration of Salts of Bumetanide to Dogs

The purpose of this study was to assess the pharmacokinetic profiles of various formulations of bumetanide, including arginine bumetanide salts (F69), potassium bumetanide salts (F10), an bumetanide emulsion (FE-9), and a nano-emulsion of bumetanide (FNE-1), which are described in Table 42, when each formulation is administered as a single intranasal dose or as a single sublingual dose in different vehicles when compared to single IV administration dose in male and female beagle dogs.

A total of four dogs were assigned to the study (3 males, 8-12 kg and 1 female, 7-11 kg). Because bumetanide is a diuretic, 30 minutes prior to dosing, the dogs received a 100 mL injection of Lactated Ringer's solution subcutaneously (SQ) for all events. The 100 mL injection was repeated ~2 hours post-dose.

This study was conducted in 9 Events in two phases (A and B) in the same animals, separated by approximately a 48 hour or more washout period between events in each phase and ~2 weeks rest period between phases, meaning Phase B events were initiated after ~2 weeks rest period from completion of Event 5. The dosing regimen for Phase A and Phase B events are described in Table 43 and 44 respectively.

TABLE 42

Intranasal and Sublingual Formulation Components

| Formulation | Ingredients | Formulation Type |
|---|---|---|
| F69 | Bumetanide, Sodium CMC (low viscosity), L-Arginine (base), Mannitol, Benzyl alcohol, HCl (acid), DI Water (pH 7.0) | Aqueous solution |
| F70 | Bumetanide, Sodium CMC (low viscosity), KOH (K+ base), Mannitol, Benzyl alcohol, HCl (acid), DI Water (pH 7.0) | Aqueous solution |
| FE-9 | Bumetanide, MCT (medium chain triglyceride), Lecithin (E-80), Polysorbate 80, Glycerol, NaOH (base), Benzyl alcohol, HCl (acid), DI water (pH 6.1) | Emulsion |
| FNE-1 | Bumetanide, Soy lecithin (PL90G), Glycocholic acid, Benzyl alcohol, NaOH (base), Dextrose, HCl (acid), DI water (pH 6.1) | Nano-emulsion |

TABLE 43

Phase A Dosing Events

| Event | Animal # | Formulation | Route | Dose Level (mg/dog) | Dose Volume | Dose Concentration (mg/mL) |
|---|---|---|---|---|---|---|
| 1 | 1501, 1001, 1002, 1003 | IV Injection | IV | 0.5 | 2.0 mL/animal | 0.25 mg/mL |
| 2 | 1501, 1001, 1002, 1003 | F69 | Intra-nasal | 0.5 | 50 µl/nostril | 5 mg/mL |
| 3 | 1501, 1001, 1002, 1003 | F70 | Intra-nasal | 0.5 | 50 µl/nostril | 5 mg/mL |
| 4 | 1501, 1001, 1002, 1003 | FE-9 | Intra-nasal | 0.5 | 50 µl/nostril | 5 mg/mL |
| 5 | 1501, 1001, 1002, 1003 | FNE1 | Intra-nasal | 0.5 | 50 µl/nostril | 5 mg/mL |

TABLE 44

Phase B Dosing Events

| Event | Animal # | Formulation | Route | Dose Level (mg/dog) | Dose Volume | Dose Concentration (mg/mL) |
|---|---|---|---|---|---|---|
| 6 | 1501, 1001, 1002, | F69 | Sub-lingual | 0.5 | 100 µl/animal | 5 mg/mL |
| 7 | 1501, 1001, 1002, | F70 | Sub-lingual | 0.5 | 100 µl/animal | 5 mg/mL |
| 8 | 1501, 1001, 1002, | FE-9 | Sub-lingual | 0.5 | 100 µl/animal | 5 mg/mL |
| 9 | 1501, 1001, 1002, | FNE1 | Sub-lingual | 0.5 | 100 µl/animal | 5 mg/mL |

For intranasal administration, each dog was held in an upright position with the nose pointing up. The bumetanide compound was delivered intranasally to the dog in a volume of 50 µL/nostril using a positive displacement pipette such that the dog received a total of 100 µL. The nose was held pointing up for ~60 seconds after dosing. After each application, successful dosing was verified by visual inspection of the pipette tip and the dog nostril. Only administrations estimated to be at least 80% of the total volume were accepted.

For intra-oral (i.e., sublingual) administration, 100 µL of the bumetanide compound was delivered into the oral cavity sublingually using a positive displacement pipette such that each dog received a total volume of 100 µL/dog. The mouth was held horizontal for ~60-120 seconds in closed position after dosing. After each application, successful dosing was verified by visual inspection of the pipette tip and the dog mouth. Only administrations estimated to at least 80% of the total volume were accepted. No food or water were allowed 1 hour prior to and 2 hours after administration of the bumetanide compound.

For intravenous administration, the injection of commercially available bumetanide (Walgreens, 0.25 mg/mL) was used and administered via the cephalic vein over a period of 30 seconds (2.0 mL/dog, IV).

Detailed clinical observations were conducted at least once daily for Phase 1 and Phase 2, until 24 hours after Event 5 and 9, and whenever an abnormality was observed. No observations were made between phases otherwise. Nostrils were observed for any adverse signs post-dose. Additional cage-side observations were conducted by animal care staff at least once daily.

Urine volume was monitored post-dose to assess diuresis by making observations at 30 minutes, 1 hour, 2 hours, and 4 hours post-dose. Urine volume was not measured.

Body weights were measured for each animal prior to each dose on the day of dose, and approximately 48 hours post-dose for each event. Body weights were provided for pharmacokinetic analysis.

On each day of dosing for both Phase A and Phase B, ~600 L was collected from the jugular vein in red top tubes with clotting activator (Sarstedt, Inc-41.1392.105 or similar) to obtain serum at the time points of pre-dose, and $2\pm1$ minutes, $5\pm1$ minutes, $10\pm2$ minutes, $15\pm2$ minutes, $20\pm3$ minutes, $30\pm3$ minutes, $45\pm3$ minutes $60\pm4$ minutes, $120\pm5$ minutes, $180\pm5$ minutes, and $240\pm5$ minutes after dosing. However, the 240 minute blood collection was not collected in Event 1 of IV dosing. Blood was centrifuged at 5000×g for 10 minutes at 4° C. If the samples are collected outside the collection window, they were not considered a protocol deviation; the collection time was provided for the purpose of pharmacokinetic analysis. Serum was divided into 2 aliquots of ~150 µL each, with one aliquot serving as a backup, and were stored frozen at −20° C. until one aliquot was shipped for bioanalysis to Climax Laboratories, Inc. on dry ice.

Figure 8:
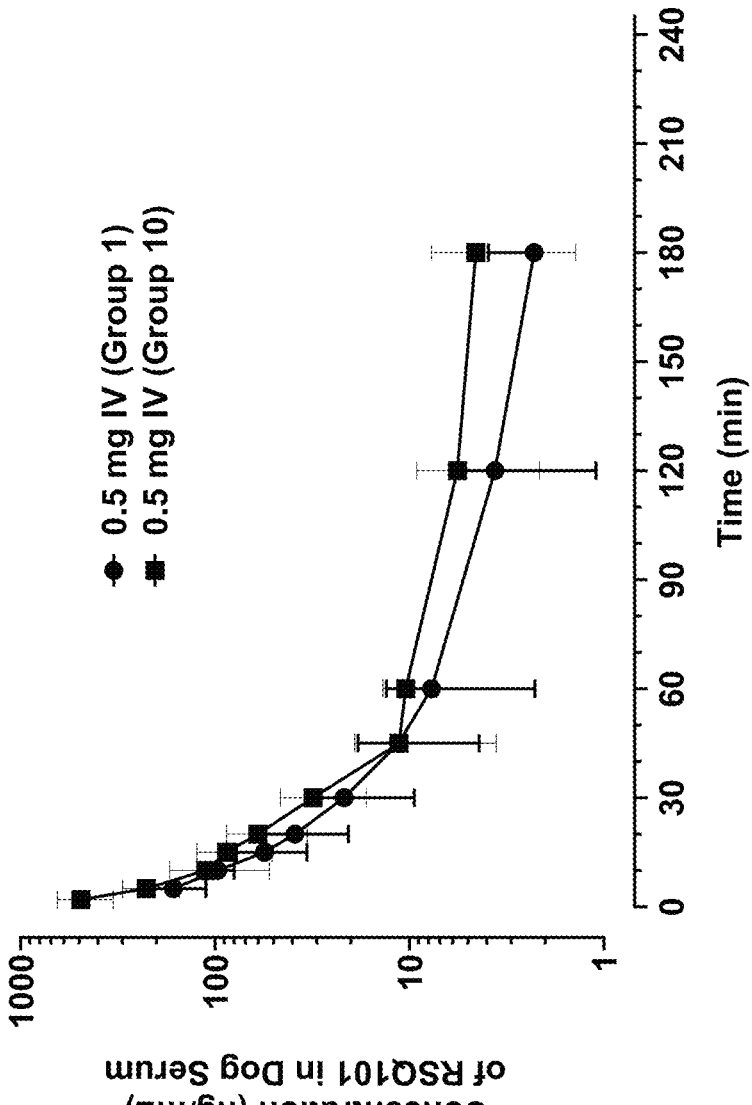
FIG. 8 is a graph showing the concentration (ng/ml) of bumetanide in the serum of dogs over a period of 2 minutes to 180 minutes after IV administration of 0.5 mg of a commercially available bumetanide in two different times in dogs.

Individual serum concentrations and pharmacokinetic parameters of bumetanide following IV administration of commercially available bumetanide to dogs are shown in Table 50 and Table 51 and presented graphically in FIG. 8. Following IV administration of bumetanide, levels of bumetanide also declined rapidly. Due to the early peak and rapid decline of bumetanide concentrations in serum following the IV dose, the IV phase was repeated with the addition of an early time point at 2 min to capture the early AUC more completely. Levels of bumetanide were higher in the second replicate, perhaps in part due to the addition of the early time point at 2 min. Mean IV PK parameters from both IV dosing occasions were used for calculation of bioavailability for the IN and SL dose routes.

When the bumetanide formulation was delivered sublingually, the potassium bumetanide formulation, F70, showed the greatest absorption in comparison to arginine bumetanide formulation, F69, the bumetanide emulsion, FE-9, and the bumetanide nano-emulsion, FNE-1, as shown in FIGS. 10, 11, and 13. Systemic exposure, as measured by the area under the curve, show that the sublingual dose of F70 approaches that of IV administration in dogs as shown in FIGS. 14 and 15. The variability of F70 following sublingual administration is similar to what is observed when the bumetanide is administered intravenously, as shown in FIG. 12. F70 showed rapid absorption, reaching $T_{max}$ between 30 and 60 minutes after administration and maintained persistent levels over 240 minutes, as shown in FIGS. 10, 11, and 13. Individual serum concentrations and pharmacokinetic parameters of bumetanide following SL administration of F69, F70, FE-9, and FNE-1 to dogs are shown in Table 52 through 55 and presented graphically in FIG. 10. Following SL administration of the bumetanide formulations, levels of bumetanide peaked at approximately 30-60 min after dosing declined thereafter.

Figure 5:
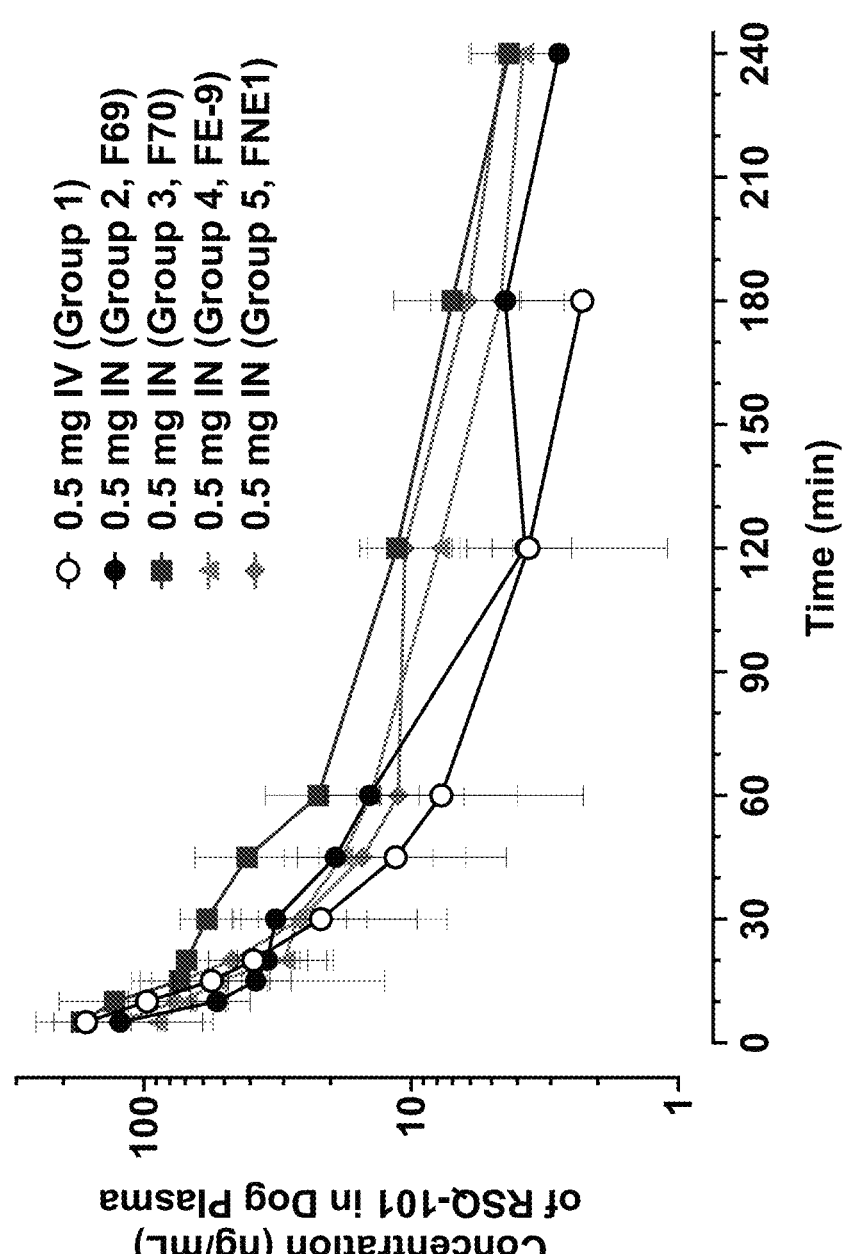
FIG. 5 is a graph showing the concentration (ng/ml) of bumetanide in the serum of dogs over a period of 2 minutes to 240 minutes after IV or IN administration of 0.5 mg to compare the concentration of bumetanide achieved in serum using IV administration of commercially available bumetanide versus the concentration of bumetanide achieved with IN administration of approximately 0.5 mg of the F69, F70, FE-9, or the FNE-1 bumetanide formulations.
Figure 6:
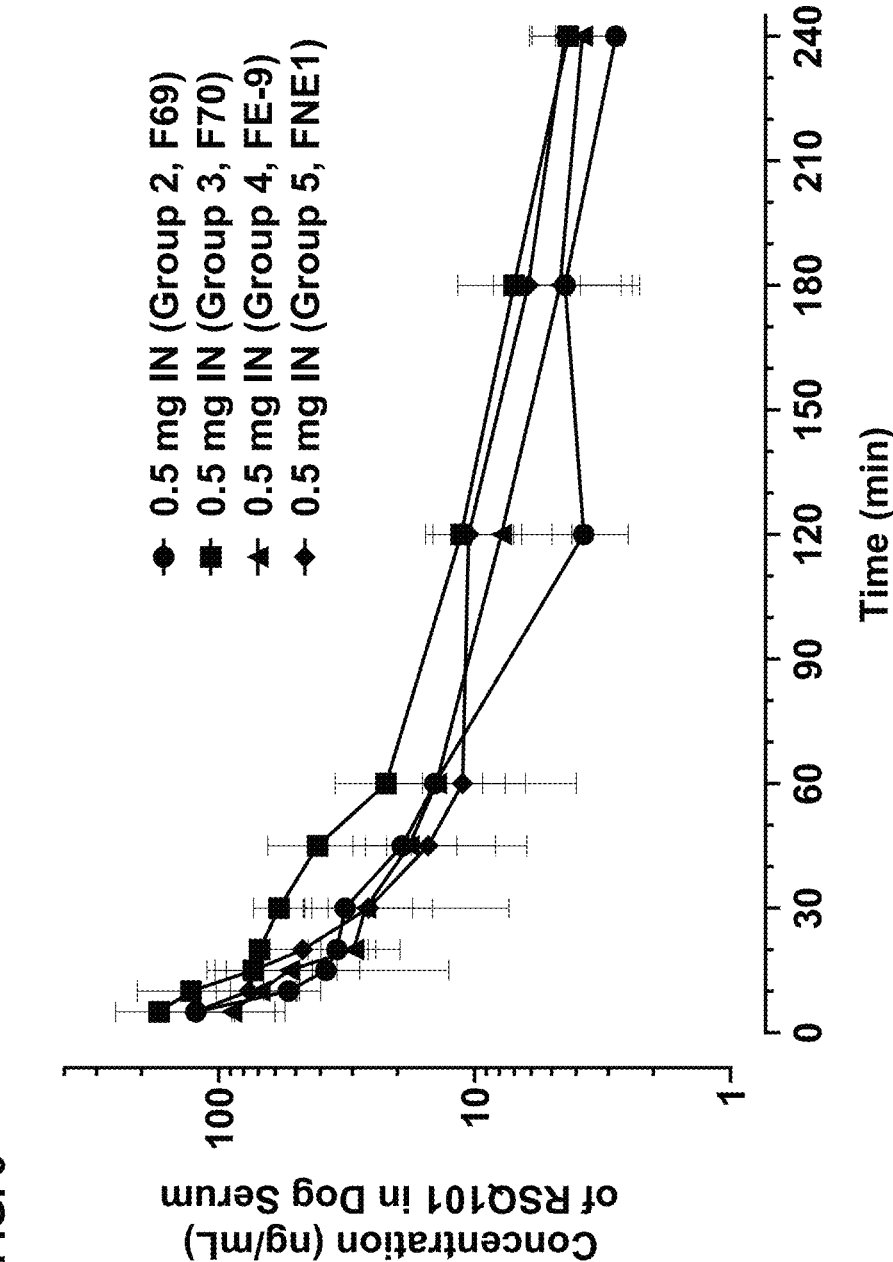
FIG. 6 is a graph showing the concentration (ng/ml) of bumetanide in the serum of dogs over a period of 2 minutes to 240 minutes after IN administration of 0.5 mg of a bumetanide compound including the arginine bumetanide salt formulation (F69), the potassium bumetanide salt formulation (F70), the bumetanide emulsion (FE-9), and the bumetanide nano-emulsion (FNE-1) on a logarithmic scale.
Figure 7:
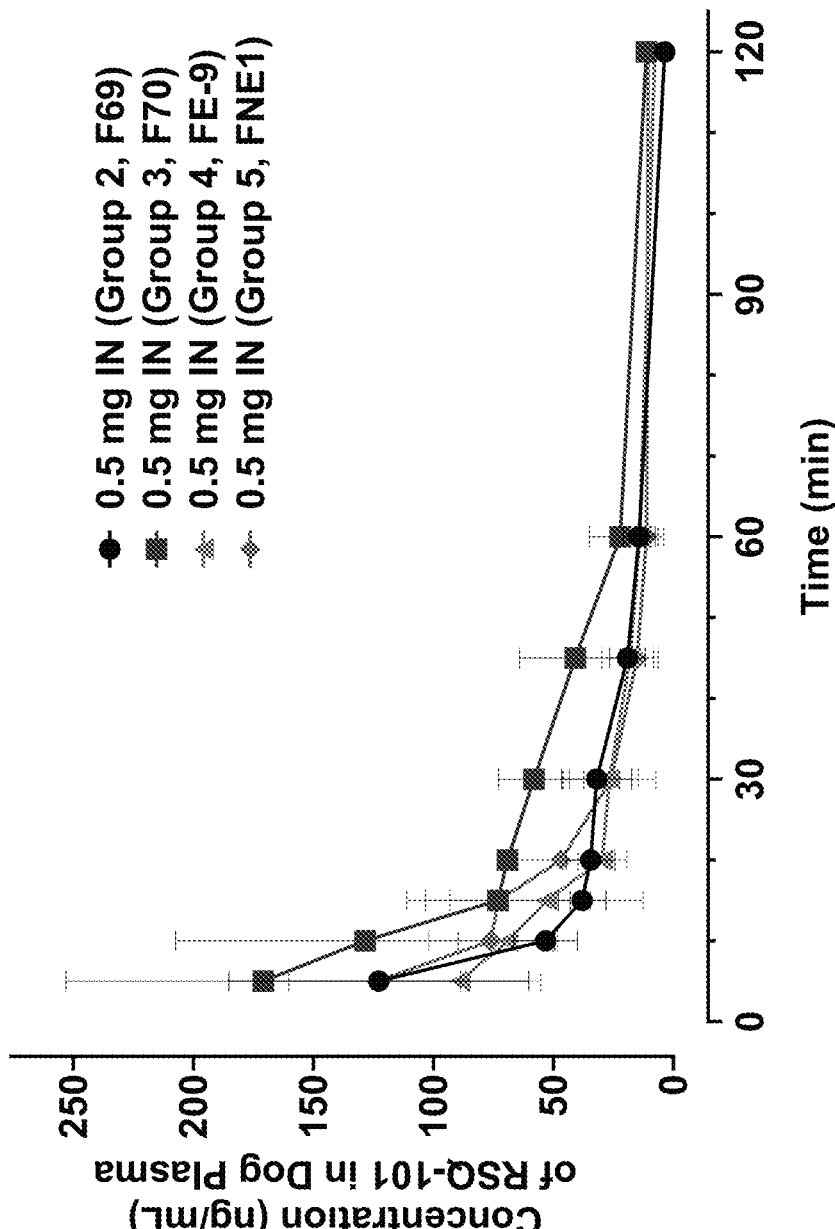
FIG. 7 is a graph showing the concentration (ng/ml) of bumetanide in the serum of dogs over a period of 2 minutes to 240 minutes after IN administration of 0.5 mg of a bumetanide compound including the arginine bumetanide salt formulation (F69), the potassium bumetanide salt formulation (F70), the bumetanide emulsion (FE-9), and the bumetanide nano-emulsion (FNE-1) on a linear scale.
Figure 9:
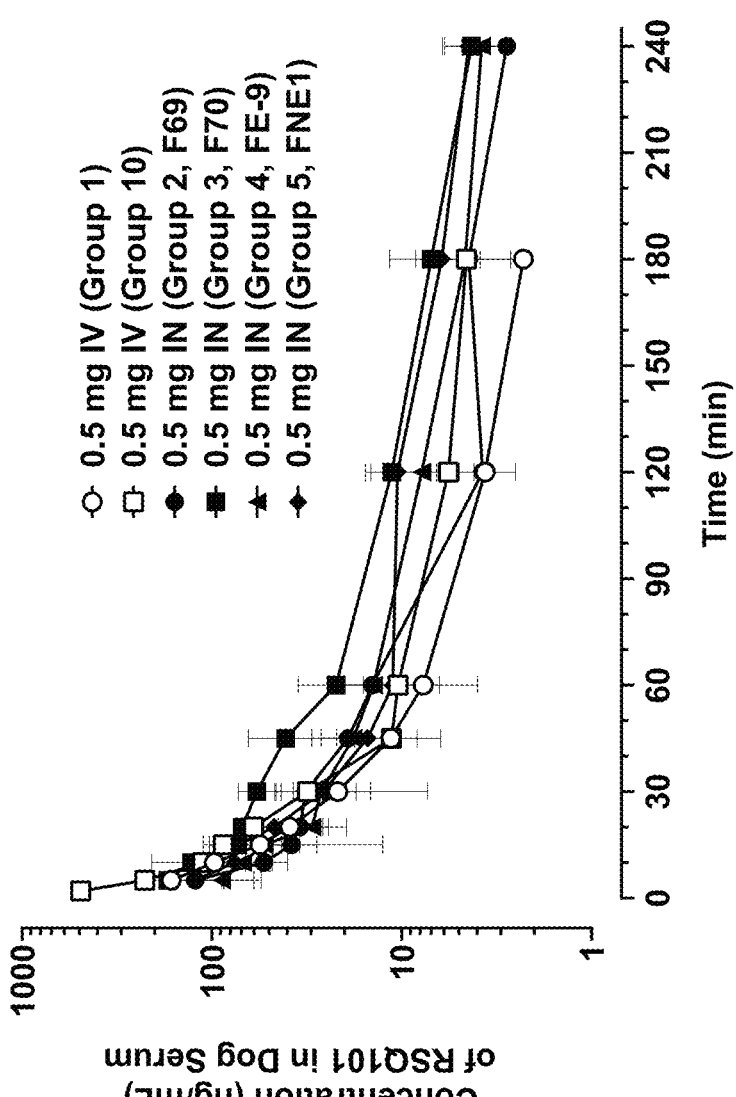
FIG. 9 is a graph showing the concentration (ng/ml) of bumetanide in the serum of dogs over a period of 2 minutes to 240 minutes after two IV administrations of 0.5 mg of a commercially available bumetanide or IN administration of 0.5 mg of a bumetanide compound including the arginine

When the bumetanide formulation was delivered intranasally, the potassium bumetanide formulation, F70, also resulted in the greatest absorption of bumetanide as shown in FIGS. 5, 6, and 7. Likewise, intranasal administration of F70 resulted in generally similar results compared to IV administration of bumetanide as is shown in FIG. 9. Like sublingual administration, intranasal administration resulted in rapid administration of F70 and more persistent levels over time in comparison to IV administration as is shown FIG. 9.

Individual serum concentrations and pharmacokinetic parameters of bumetanide following IN administration of F69, F70, FE-9, and FNE-1 to dogs are shown in Table 46 through Table 49 and presented graphically in FIGS. 6 and 7. Following IN administration of the bumetanide formulations, levels of bumetanide peaked rapidly (usually at 5 to 10 minutes) and immediately declined thereafter. A summary of the calculated bioavailability for intranasal, IV, and sublingual administration of the various bumetanide formulations is described in Table 45. Systemic exposure, as measured by the area under the curve, show that the intranasal dose of F70 approaches that of IV administration in dogs as shown in FIGS. 14 and 16.

TABLE 45

Serum Pharmacokinetic Parameters of Bumetanide in Dogs Given a Single IN, IV, or SL Dose of a Bumetanide Formulation

| Route | Formulation | $C_{max}$ (ng/mL) | $T_{max}$ (min) | $AUC_{0-t}$ (ng*h/mL) | Dose (mg) | Dose (mg/kg) | Bioavailability |
|---|---|---|---|---|---|---|---|
| IN | F69 | 123 | 5 | 52.2 | 0.513 | 0.0538 | 66.8% |
| IN | F70 | 183 | 5 | 96.4 | 0.516 | 0.0551 | 115% |
| IN | FE-9 | 101 | 10 | 54.6 | 0.467 | 0.0495 | 78.1% |
| IN | FNE1 | 124 | 5 | 63.7 | 0.483 | 0.0519 | 84.4% |
| IV | Solution (1st) | — | — | 60.4 | 0.500 | 0.0534 | — |
| IV | Solution ($2^{nd}$) | — | — | 97.4 | 0.500 | 0.0531 | — |
| SL | F69 | 20 | 37.5 | 37.1 | 0.513 | 0.0531 | 49.8% |
| SL | F70 | 45 | 52.5 | 66.4 | 0.516 | 0.0555 | 79.6% |
| SL | FE-9 | 29.2 | 32.5 | 46.5 | 0.467 | 0.0498 | 63.1% |
| SL | FNE1 | 37.9 | 60 | 55.0 | 0.483 | 0.0512 | 70.1% |

Values are mean of 4 animals in each group, other than $T_{max}$, which is the median of 4 animals

TABLE 46

Bumetanide Serum Concentrations and Pharmacokinetic Parameters in Dogs Given a 2 × 50 µL IN Dose, approximately 0.5 mg, of Formulation F69

Animal ID, Sex, Serum Concentration (ng/mL) and PK Parameters

| Time (min) | 1501 Female | 1001 Male | 1002 Male | 1003 Male | Mean* | SD |
|---|---|---|---|---|---|---|
| 0 (predose) | BQL | BQL | BQL | BQL | BQL | — |
| 5 | 96.5 | 61.5 | 125 | 208 | 123 | 62.5 |
| 10 | 68.6 | 56.7 | 36.3 | 51.8 | 53.4 | 13.4 |
| 15 | 45.6 | 24.4 | 36.9 | 45.6 | 38.1 | 10.0 |
| 20 | 37.8 | 19.4 | 41.0 | 39.9 | 34.5 | 10.2 |
| 30 | 28.2 | 14.0 | 37.6 | 48.5 | 32.1 | 14.6 |
| 45 | 16.8 | 9.71 | 25.4 | 24.9 | 19.2 | 7.46 |
| 60 | 11.3 | 7.27 | 15.7 | 22.9 | 14.3 | 6.69 |
| 120 | 4.42 | 4.15 | 4.51 | 1.91 | 3.75 | 1.23 |
| 180 | 2.89 | 7.27 | 2.61 | 4.96 | 4.43 | 2.16 |
| 240 | 2.59 | 2.77 | 2.87 | 2.98 | 2.80 | 0.166 |
| $C_{max}$ (ng/mL) | 96.5 | 61.5 | 125 | 208 | 123 | 62.5 |
| $T_{max}$ (min) | 5 | 5 | 5 | 5 | 5 | — |
| $AUC_{0-t}$ (ng*min/mL) | 2882 | 2220 | 3252 | 4166 | 3130 | 812 |
| $AUC_{0-t}$ (ng*h/mL) | 48.0 | 37.0 | 54.2 | 69.4 | 52.2 | 13.5 |
| Weight (kg) | 8.4 | 10.7 | 9.8 | 9.5 | 9.60 | 0.949 |
| Dose (mg) | 0.513 | 0.513 | 0.513 | 0.513 | 0.513 | — |
| Dose (mg/kg) | 0.0611 | 0.0479 | 0.0523 | 0.0540 | 0.0538 | 0.0055 |
| DA $AUC_{0-t}$ (ng*h/mL)/(mg/kg) | 786 | 772 | 1035 | 1286 | 970 | 243 |
| Bioavailability | 60.8% | 77.5% | 54.3% | 74.5% | 66.8% | 11.0% |

*Median for $T_{max}$, DA = Dose Adjusted

TABLE 17

Bumetanide Serum Concentrations and Pharmacokinetic Parameters in Dogs Given a 2 × 50 µL IN Dose, approximately 0.5 mg, of Formulation F70

Animal ID, Sex, Serum Concentration (ng/mL) and PK Parameters

| Time (min) | 1501 Female | 1001 Male | 1002 Male | 1003 Male | Mean* | SD |
|---|---|---|---|---|---|---|
| 0 (predose) | BQL | BQL | BQL | BQL | BQL | — |
| 5 | 128 | 137 | 294 | 125 | 171 | 82.2 |
| 10 | 104 | 29.1 | 208 | 173 | 129 | 79.1 |

TABLE 17-continued

Bumetanide Serum Concentrations and Pharmacokinetic Parameters in Dogs Given a
2 × 50 μL IN Dose, approximately 0.5 mg, of Formulation F70

Animal ID, Sex, Serum Concentration (ng/mL) and PK Parameters

| Time (min) | 1501 Female | 1001 Male | 1002 Male | 1003 Male | Mean* | SD |
|---|---|---|---|---|---|---|
| 15 | 77.9 | 30.1 | 84.9 | 99.8 | 73.2 | 30.1 |
| 20 | 65.2 | 70.0 | 73.7 | 68.0 | 69.2 | 3.57 |
| 30 | 59.0 | 36.9 | 67.8 | 68.8 | 58.1 | 14.8 |
| 45 | 31.3 | 13.0 | 55.3 | 64.4 | 41.0 | 23.3 |
| 60 | 19.1 | 8.09 | 39.2 | 22.4 | 22.2 | 12.9 |
| 120 | 12.6 | 4.98 | 14.2 | 13.4 | 11.3 | 4.26 |
| 180 | 5.81 | 2.03 | 13.1 | 7.12 | 7.02 | 4.59 |
| 240 | 5.26 | 2.93 | 6.14 | 2.87 | 4.30 | 1.66 |
| $C_{max}$ (ng/mL) | 128 | 137 | 294 | 173 | 183 | 76.5 |
| $T_{max}$ (min) | 5 | 5 | 5 | 10 | 5 | — |
| $AUC_{0-t}$ (ng*min/mL) | 5224 | 2974 | 8456 | 6482 | 5784 | 2298 |
| $AUC_{0-t}$ (ng*h/mL) | 87.1 | 49.6 | 140.9 | 108.0 | 96.4 | 38.3 |
| Weight (kg) | 8.2 | 10.5 | 9.9 | 9.2 | 9.45 | 0.988 |
| Dose (mg) | 0.516 | 0.516 | 0.516 | 0.516 | 0.516 | — |
| Dose (mg/kg) | 0.0629 | 0.0491 | 0.0521 | 0.0561 | 0.0551 | 0.0060 |
| DA $AUC_{0-t}$ (ng*h/mL)/(mg/kg) | 1384 | 1009 | 2704 | 1926 | 1756 | 736 |
| Bioavailability | 107% | 101% | 142% | 112% | 115% | 18.1% |

*Median for $T_{max}$, DA = Dose Adjusted

TABLE 48

Bumetanide Serum Concentrations and Pharmacokinetic Parameters in Dogs Given a
2 × 50 μL IN Dose, approximately 0.5 mg, of Formulation FE-9

Animal ID, Sex, Serum Concentration (ng/mL) and PK Parameters

| Time (min) | 1501 Female | 1001 Male | 1002 Male | 1003 Male | Mean* | SD |
|---|---|---|---|---|---|---|
| 0 (predose) | BQL | 6.54 | BQL | BQL | BQL | — |
| 5 | 72.8 | 128 | 104 | 51.1 | 89.0 | 33.9 |
| 10 | 84.2 | 38.4 | 75.5 | 78.0 | 69.0 | 20.7 |
| 15 | 44.2 | 33.1 | 112 | 22.5 | 53.0 | 40.4 |
| 20 | 28.1 | 24.5 | 44.5 | 21.8 | 29.7 | 10.2 |
| 30 | 22.0 | 7.33 | 53.5 | 23.9 | 26.7 | 19.4 |
| 45 | 4.38 | 21.7 | 32.2 | 13.9 | 18.0 | 11.8 |
| 60 | 18.7 | 2.75 | 25.7 | 9.33 | 14.1 | 10.1 |
| 120 | 4.63 | 11.7 | 10.3 | 4.78 | 7.85 | 3.68 |
| 180 | 2.82 | 5.62 | 6.90 | 3.19 | 4.63 | 1.96 |
| 240 | 3.54 | 4.36 | 4.83 | 2.46 | 3.80 | 1.04 |
| $C_{max}$ (ng/mL) | 84.2 | 128 | 112 | 78.0 | 101 | 23.5 |
| $T_{max}$ (min) | 10 | 5 | 15 | 10 | 10 | — |
| $AUC_{0-t}$ (ng*min/mL) | 2812 | 2872 | 5084 | 2331 | 3274 | 1230 |
| $AUC_{0-t}$ (ng*h/mL) | 46.9 | 47.9 | 84.7 | 38.8 | 54.6 | 20.5 |
| Weight (kg) | 8.2 | 10.7 | 9.8 | 9.4 | 9.53 | 1.037 |
| Dose (mg) | 0.467 | 0.467 | 0.467 | 0.467 | 0.467 | — |
| Dose (mg/kg) | 0.0570 | 0.0436 | 0.0477 | 0.0497 | 0.0495 | 0.0056 |
| DA $AUC_{0-t}$ (ng*h/mL)/(mg/kg) | 823 | 1097 | 1778 | 782 | 1120 | 460 |
| Bioavailability | 63.7% | 110% | 93.2% | 45.3% | 78.1% | 29.1% |

*Median for $T_{max}$, DA = Dose Adjusted

TABLE 49

Bumetanide Serum Concentrations and Pharmacokinetic Parameters in Dogs Given a
2 × 50 μL IN Dose, approximately 0.5 mg, of Formulation FNE-1

Animal ID, Sex, Serum Concentration (ng/mL) and PK Parameters

| Time (min) | 1501 Female | 1001 Male | 1002 Male | 1003 Male | Mean* | SD |
|---|---|---|---|---|---|---|
| 0 (predose) | BQL | BQL | BQL | BQL | BQL | — |
| 5 | 148 | 69.3 | 132 | 145 | 124 | 36.8 |

TABLE 49-continued

Bumetanide Serum Concentrations and Pharmacokinetic Parameters in Dogs Given a
2 × 50 μL IN Dose, approximately 0.5 mg, of Formulation FNE-1

| | Animal ID, Sex, Serum Concentration (ng/mL) and PK Parameters | | | | | |
|---|---|---|---|---|---|---|
| Time (min) | 1501 Female | 1001 Male | 1002 Male | 1003 Male | Mean* | SD |
| 10 | 91.0 | 39.4 | 77.0 | 97.1 | 76.1 | 25.9 |
| 15 | 62.7 | 26.6 | 84.2 | 118 | 72.9 | 38.3 |
| 20 | 53.0 | 19.3 | 46.0 | 69.3 | 46.9 | 20.8 |
| 30 | 31.3 | 10.5 | 36.8 | 25.2 | 26.0 | 11.3 |
| 45 | 19.3 | 5.15 | 20.1 | 16.2 | 15.2 | 6.90 |
| 60 | 15.0 | 4.12 | 13.1 | 12.4 | 11.2 | 4.82 |
| 120 | 4.97 | 14.3 | 12.1 | 10.8 | 10.5 | 3.99 |
| 180 | 3.43 | 8.35 | 5.12 | 7.75 | 6.16 | 2.30 |
| 240 | 3.10 | 4.35 | 6.80 | 3.52 | 4.44 | 1.66 |
| $C_{max}$ (ng/mL) | 148 | 69.3 | 132 | 145 | 124 | 36.8 |
| $T_{max}$ (min) | 5 | 5 | 5 | 5 | 5 | — |
| $AUC_{0-t}$ (ng*min/mL) | 3746 | 2674 | 4301 | 4562 | 3821 | 837 |
| $AUC_{0-t}$ (ng*h/mL) | 62.4 | 44.6 | 71.7 | 76.0 | 63.7 | 13.9 |
| Weight (kg) | 8.1 | 10 | 9.8 | 9.6 | 9.38 | 0.866 |
| Dose (mg) | 0.483 | 0.483 | 0.483 | 0.483 | 0.483 | — |
| Dose (mg/kg) | 0.0596 | 0.0483 | 0.0493 | 0.0503 | 0.0519 | 0.0052 |
| DA $AUC_{0-t}$ (ng*h/mL)/(mg/kg) | 1047 | 923 | 1454 | 1511 | 1234 | 293 |
| Bioavailability | 81.0% | 92.7% | 76.3% | 87.5% | 84.4% | 7.20% |

*Median for $T_{max}$, DA = Dose Adjusted

TABLE 50

Bumetanide Serum Concentrations and Pharmacokinetic Parameters in Dogs Given a
0.5-mg IV Dose of Bumetanide (First Replicate)

| | Animal ID, Sex, Serum Concentration (ng/mL) and PK Parameters | | | | | |
|---|---|---|---|---|---|---|
| Time (min) | 1501 Female | 1001 Male | 1002 Male | 1003 Male | Mean | SD |
| 0 (predose) | BQL | BQL | BQL | BQL | BQL | — |
| 5 | 191 | 94.7 | 216 | 155 | 164 | 52.7 |
| 10 | 93.9 | 89.1 | 122 | 83.5 | 97.1 | 17.1 |
| 15 | 55.2 | 32.1 | 85.2 | 50.5 | 55.8 | 22.0 |
| 20 | 38.0 | 20.5 | 64.0 | 33.2 | 38.9 | 18.3 |
| 30 | 17.1 | 13.1 | 40.0 | 16.9 | 21.8 | 12.3 |
| 45 | 10.7 | 4.58 | 21.2 | 9.20 | 11.4 | 7.02 |
| 60 | 5.87 | 4.19 | 15.8 | 4.97 | 7.71 | 5.44 |
| 120 | 2.61 | 1.61 | 7.35 | 2.99 | 3.64 | 2.54 |
| 180 | 1.91 | 1.15 | 4.71 | 1.39 | 2.29 | 1.64 |
| $AUC_{0-t}$ (ng*min/mL) | 3765 | 2006 | 5545 | 3170 | 3621 | 1476 |
| $AUC_{0-t}$ (ng*h/mL) | 62.8 | 33.4 | 92.4 | 52.8 | 60.4 | 24.6 |
| Weight (kg) | 8.1 | 10.6 | 9.6 | 9.5 | 9.45 | 1.03 |
| Dose (mg) | 0.500 | 0.500 | 0.500 | 0.500 | 0.500 | — |
| Dose (mg/kg) | 0.0617 | 0.0472 | 0.0521 | 0.0526 | 0.0534 | 0.0061 |
| DA $AUC_{0-t}$ (ng*h/mL)/(mg/kg) | 1017 | 709 | 1774 | 1004 | 1126 | 455 |

DA = Dose Adjusted

TABLE 51

Bumetanide Serum Concentrations and Pharmacokinetic Parameters in Dogs Given a
0.5-mg IV Dose of Bumetanide (Second Replicate)

| | Animal ID, Sex, Serum Concentration (ng/mL) and PK Parameters | | | | | |
|---|---|---|---|---|---|---|
| Time (min) | 1501 Female | 1001 Male | 1002 Male | 1003 Male | Mean | SD |
| 0 (predose) | BQL | BQL | BQL | BQL | BQL | — |
| 2 | 583 | 325 | 396 | 659 | 491 | 156 |
| 5 | 273 | 125 | 221 | 287 | 227 | 73.4 |

TABLE 51-continued

Bumetanide Serum Concentrations and Pharmacokinetic Parameters in Dogs Given a
0.5-mg IV Dose of Bumetanide (Second Replicate)

| | Animal ID, Sex, Serum Concentration (ng/mL) and PK Parameters | | | | | |
|---|---|---|---|---|---|---|
| Time (min) | 1501 Female | 1001 Male | 1002 Male | 1003 Male | Mean | SD |
| 10 | 63.2 | 61.7 | 142 | 181 | 112 | 59.4 |
| 15 | 101 | 33.0 | 105 | 111 | 87.5 | 36.6 |
| 20 | 48.8 | 28.1 | 83.8 | 81.2 | 60.5 | 26.8 |
| 30 | 22.2 | 16.2 | 47.7 | 39.6 | 31.4 | 14.7 |
| 45 | 13.9 | 9.40 | 1.82 | 20.3 | 11.4 | 7.77 |
| 60 | 9.51 | 7.01 | 14.8 | 10.6 | 10.5 | 3.25 |
| 120 | 2.05 | 3.33 | 9.32 | 8.01 | 5.68 | 3.53 |
| 180 | 2.30 | 8.23 | 6.15 | 1.58 | 4.57 | 3.16 |
| $AUC_{0-t}$ (ng*min/mL) | 5738 | 3664 | 6244 | 7736 | 5846 | 1684 |
| $AUC_{0-t}$ (ng*h/mL) | 95.6 | 61.1 | 104 | 129 | 97 | 28.1 |
| Weight (kg) | 8.2 | 10.5 | 9.8 | 9.5 | 9.50 | 0.963 |
| Dose (mg) | 0.500 | 0.500 | 0.500 | 0.500 | 0.500 | — |
| Dose (mg/kg) | 0.0610 | 0.0476 | 0.0510 | 0.0526 | 0.0531 | 0.0057 |
| DA $AUC_{0-t}$ (ng*h/mL)/(mg/kg) | 1568 | 1283 | 2040 | 2450 | 1835 | 515 |

DA = Dose Adjusted

TABLE 52

Bumetanide Serum Concentrations and Pharmacokinetic Parameters in Dogs Given a
100-µL SL Dose, approximately 0.5 mg, of Formulation F69

| | Animal ID, Sex, Serum Concentration (ng/mL) and PK Parameters | | | | | |
|---|---|---|---|---|---|---|
| Time (min) | 1501 Female | 1001 Male | 1002 Male | 1003 Male | Mean* | SD |
| 0 (predose) | BQL | BQL | BQL | BQL | BQL | — |
| 5 | 4.90 | 0.782 | 1.75 | 2.36 | 2.45 | 1.76 |
| 10 | 16.8 | 0.992 | 2.63 | 5.57 | 6.50 | 7.12 |
| 15 | 24.8 | 4.39 | 2.59 | 7.49 | 9.82 | 10.2 |
| 20 | 24.5 | 14.9 | 2.37 | 9.54 | 12.8 | 9.32 |
| 30 | 20.4 | 28.0 | 3.62 | 10.7 | 15.7 | 10.7 |
| 45 | 21.1 | 19.3 | 3.90 | 11.1 | 13.9 | 7.93 |
| 60 | 24.7 | 15.0 | 7.87 | 10.6 | 14.5 | 7.38 |
| 120 | 6.86 | 4.23 | 17.0 | 8.24 | 9.08 | 5.53 |
| 180 | 5.42 | 3.72 | 11.2 | 5.96 | 6.58 | 3.23 |
| 240 | 3.56 | 3.08 | 10.5 | 2.71 | 4.96 | 3.71 |
| $C_{max}$ (ng/mL) | 24.8 | 28 | 17 | 11.1 | 20 | 7.6 |
| $T_{max}$ (min) | 15 | 30 | 120 | 45 | 37.5 | — |
| $AUC_{0-t}$ (ng*min/mL) | 2758 | 1914 | 2459 | 1780 | 2227 | 459 |
| $AUC_{0-t}$ (ng*h/mL) | 46.0 | 31.9 | 41.0 | 29.7 | 37.1 | 7.7 |
| Weight (kg) | 8.2 | 10.7 | 10 | 10.1 | 9.75 | 1.079 |
| Dose (mg) | 0.513 | 0.513 | 0.513 | 0.513 | 0.513 | — |
| Dose (mg/kg) | 0.0626 | 0.0479 | 0.0513 | 0.0508 | 0.0531 | 0.0064 |
| DA $AUC_{0-t}$ (ng*h/mL)/(mg/kg) | 735 | 665 | 799 | 584 | 696 | 92.3 |
| Bioavailability | 56.8% | 66.8% | 41.9% | 33.8% | 49.8% | 14.8% |

*Median for $T_{max}$, DA = Dose Adjusted

TABLE 53

Bumetanide Serum Concentrations and Pharmacokinetic Parameters in Dogs Given a
100-µL SL Dose, approximately 0.5 mg, of Formulation F70

| | Animal ID, Sex, Serum Concentration (ng/mL) and PK Parameters | | | | | |
|---|---|---|---|---|---|---|
| Time (min) | 1501 Female | 1001 Male | 1002 Male | 1003 Male | Mean* | SD |
| 0 (predose) | BQL | BQL | BQL | BQL | BQL | — |
| 5 | 0.839 | 1.21 | 1.26 | 1.17 | 1.12 | 0.191 |
| 10 | 2.07 | 0.903 | 2.01 | 19.1 | 6.02 | 8.74 |

TABLE 53-continued

Bumetanide Serum Concentrations and Pharmacokinetic Parameters in Dogs Given a
100-μL SL Dose, approximately 0.5 mg, of Formulation F70

| | Animal ID, Sex, Serum Concentration (ng/mL) and PK Parameters | | | | | |
|---|---|---|---|---|---|---|
| | 1501 | 1001 | 1002 | 1003 | | |
| Time (min) | Female | Male | Male | Male | Mean* | SD |
| 15 | 4.90 | 2.94 | 2.02 | 45.5 | 13.8 | 21.1 |
| 20 | 10.7 | 10.2 | 2.78 | 53.6 | 19.3 | 23.1 |
| 30 | 18.1 | 15.9 | 3.71 | 55.6 | 23.3 | 22.4 |
| 45 | 68.8 | 21.0 | 23.3 | 35.7 | 37.2 | 22.0 |
| 60 | 75.7 | 11.6 | 28.9 | 27.9 | 36.0 | 27.6 |
| 120 | 10.7 | 4.74 | 18.3 | 11.2 | 11.2 | 5.55 |
| 180 | 7.41 | 6.91 | 18.2 | 9.28 | 10.5 | 5.27 |
| 240 | 4.17 | 3.10 | 16.0 | 7.70 | 7.74 | 5.85 |
| $C_{max}$ (ng/mL) | 75.7 | 21 | 28.9 | 55.6 | 45 | 25.1 |
| $T_{max}$ (min) | 60 | 45 | 60 | 30 | 52.5 | — |
| $AUC_{0-t}$ (ng*min/mL) | 5428 | 1843 | 4197 | 4467 | 3984 | 1522 |
| $AUC_{0-t}$ (ng*h/mL) | 90.5 | 30.7 | 69.9 | 74.5 | 66.4 | 25.4 |
| Weight (kg) | 8.00 | 10.4 | 9.6 | 9.5 | 9.38 | 1.001 |
| Dose (mg) | 0.516 | 0.516 | 0.516 | 0.516 | 0.516 | — |
| Dose (mg/kg) | 0.0645 | 0.0496 | 0.0538 | 0.0543 | 0.0555 | 0.0063 |
| DA $AUC_{0-t}$ (ng*h/mL)/(mg/kg) | 1403 | 619 | 1301 | 1371 | 1173 | 372 |
| Bioavailability | 109% | 62.2% | 68.2% | 79.4% | 79.6% | 20.6% |

*Median for $T_{max}$, DA = Dose Adjusted

TABLE 54

Bumetanide Serum Concentrations and Pharmacokinetic Parameters in Dogs Given a
100-μL SL Dose, approximately 0.5 mg, of Formulation FE-9

| | Animal ID, Sex, Serum Concentration (ng/mL) and PK Parameters | | | | | |
|---|---|---|---|---|---|---|
| | 1501 | 1001 | 1002 | 1003 | | |
| Time (min) | Female | Male | Male | Male | Mean* | SD |
| 0 (predose) | BQL | 6.54 | BQL | BQL | BQL | — |
| 5 | 2.72 | 4.46 | 0 | 0.893 | 2.02 | 1.98 |
| 10 | 6.47 | 12.6 | 1.17 | 2.05 | 5.57 | 5.23 |
| 15 | 10.6 | 20.8 | 4.12 | 2.88 | 9.60 | 8.20 |
| 20 | 15.7 | 28.0 | 13.2 | 6.27 | 15.8 | 9.06 |
| 30 | 15.5 | 22.4 | 36.6 | 12.2 | 21.7 | 10.8 |
| 45 | 15.6 | 16.3 | 42.1 | 23.2 | 24.3 | 12.4 |
| 60 | 13.1 | 12.0 | 37.2 | 31.1 | 23.4 | 12.7 |
| 120 | 5.18 | 4.21 | 18.0 | 12.0 | 9.85 | 6.45 |
| 180 | 3.92 | 3.53 | 9.30 | 6.58 | 5.83 | 2.68 |
| 240 | 3.47 | 2.64 | 5.76 | 5.72 | 4.40 | 1.59 |
| $C_{max}$ (ng/mL) | 15.7 | 28.0 | 42.1 | 31.1 | 29.2 | 10.9 |
| $T_{max}$ (min) | 20 | 20 | 45 | 60 | 32.5 | — |
| $AUC_{0-t}$ (ng*min/mL) | 1786 | 1917 | 4420 | 3029 | 2788 | 1223 |
| $AUC_{0-t}$ (ng*h/mL) | 29.8 | 32.0 | 73.7 | 50.5 | 46.5 | 20.4 |
| Weight (kg) | 8 | 10.5 | 9.7 | 9.7 | 9.48 | 1.053 |
| Dose (mg) | 0.467 | 0.467 | 0.467 | 0.467 | 0.467 | — |
| Dose (mg/kg) | 0.0584 | 0.0445 | 0.0481 | 0.0481 | 0.0498 | 0.0060 |
| DA $AUC_{0-t}$ (ng*h/mL)/(mg/kg) | 510 | 719 | 1530 | 1049 | 952 | 445 |
| Bioavailability | 39.4% | 72.2% | 80.2% | 60.7% | 63.1% | 17.7% |

*Median for $T_{max}$, DA = Dose Adjusted

TABLE 55

Bumetanide Serum Concentrations and Pharmacokinetic Parameters in Dogs Given a
100-μL SL Dose, approximately 0.5 mg, of Formulation FNE-1

| | Animal ID, Sex, Serum Concentration (ng/mL) and PK Parameters | | | | | |
|---|---|---|---|---|---|---|
| Time (min) | 1501 Female | 1001 Male | 1002 Male | 1003 Male | Mean* | SD |
| 0 (predose) | BQL | BQL | BQL | BQL | BQL | — |
| 5 | 2.96 | BQL | 5.96 | 14.7 | 5.91 | 6.35 |
| 10 | 22.2 | 1.12 | 4.55 | 0.540 | 7.10 | 10.2 |
| 15 | 45.2 | 1.42 | 10.3 | 1.63 | 14.6 | 20.8 |
| 20 | 68.6 | 2.00 | 11.2 | 4.98 | 21.7 | 31.5 |
| 30 | 76.9 | 2.21 | 9.68 | 19.5 | 27.1 | 34.0 |
| 45 | 55.0 | 3.33 | 21.4 | 31.0 | 27.7 | 21.5 |
| 60 | 27.7 | 12.8 | 29.7 | 32.2 | 25.6 | 8.73 |
| 120 | 5.62 | 5.25 | 15.3 | 18.2 | 11.1 | 6.64 |
| 180 | 7.10 | 2.88 | 11.1 | 9.12 | 7.55 | 3.52 |
| 240 | 3.83 | 3.60 | 5.81 | 9.06 | 5.58 | 2.53 |
| $C_{max}$ (ng/mL) | 76.9 | 12.8 | 29.7 | 32.2 | 37.9 | 27.4 |
| $T_{max}$ (min) | 30 | 60 | 60 | 60 | 60 | — |
| $AUC_{0-t}$ (ng*min/mL) | 4569 | 1181 | 3502 | 3949 | 3300 | 1479 |
| $AUC_{0-t}$ (ng*h/mL) | 76.2 | 19.7 | 58.4 | 65.8 | 55.0 | 24.7 |
| Weight (kg) | 8.1 | 10.6 | 9.7 | 9.7 | 9.53 | 1.04 |
| Dose (mg) | 0.483 | 0.483 | 0.483 | 0.483 | 0.483 | — |
| Dose (mg/kg) | 0.0596 | 0.0456 | 0.0498 | 0.0498 | 0.0512 | 0.0060 |
| DA $AUC_{0-t}$ (ng*h/mL)/(mg/kg) | 1277 | 432 | 1172 | 1322 | 1051 | 417 |
| Bioavailability | 98.8% | 43.4% | 61.5% | 76.5% | 70.1% | 23.5% |

*Median for $T_{max}$, DA = Dose Adjusted

Bumetanide was absorbed rapidly into systemic circulation from all of the IN formulations in dogs, with median Tmax of 5-10 minutes after dosing and declined rapidly thereafter. Following IV administration of bumetanide, levels of bumetanide also declined rapidly. Following sublingual administration of bumetanide, levels of bumetanide peaked at approximately 30-60 min after dosing declined thereafter. All animals appeared normal during this study. Based on the results of this study, administration of bumetanide as a single intranasal dose or as a single sub-lingual dose in four formulations in different vehicles when compared to single IV administration dose in male and female Beagle dogs was well tolerated and did not result in death or morbidity, biologically, or toxicologically relevant clinical observations, body weight change, abnormal body condition score, clinical chemistry, hematology or urinalysis changes. After IV, IN, and sub-lingual dosing, a diuretic effect was observed within 30 to 120 minutes following dosing and the effect lasted over 4 hours post-dosing for the duration of observations.

The F70 formulation including the potassium salt of bumetanide showed greater nasal absorption of bumetanide than the other three formulations, which included other bumetanide salts. The F70 formulation also showed greater sub-lingual absorption in comparison to the other three formulations tested. Additionally, the systemic exposure of F70 following IN administration was generally similar to IV administration in dogs, and the variability of F70 following IN administration was similar to IV administration of F70 which showed rapid absorption, similar to intravenously administered bumetanide, and had more persistent levels.

OTHER EMBODIMENTS

Various modifications and variations of the described disclosure will be apparent to those skilled in the art without departing from the scope and spirit of the disclosure. Although the disclosure has been described in connection with specific embodiments, it should be understood that the disclosure as claimed should not be unduly limited to such specific embodiments. Indeed, various modifications of the described modes for carrying out the disclosure that are obvious to those skilled in the art are intended to be within the scope of the disclosure.

Other embodiments are in the claims.

The invention claimed is:

1. A stable pharmaceutical composition comprising an aqueous solution comprising (a) about 0.5 to 2 percent bumetanide (wt/wt), (b) about 0.1 percent low viscosity sodium carboxymethyl cellulose (wt/wt), (c) about 0.5 percent benzyl alcohol (wt/wt), (c) about 0.078 to 0.31 percent potassium ion (wt/wt), and (d) about 2 to 4 percent mannitol (wt/wt), and wherein the aqueous solution has a pH between about 6 and about 8.

2. The pharmaceutical composition of claim 1, wherein the pharmaceutical composition comprises about 0.5 percent bumetanide (wt/wt).

3. The pharmaceutical composition of claim 2, wherein the pharmaceutical composition comprises about 4 percent mannitol (wt/wt).

4. A method of treating edema in a subject, said method comprising administering to the subject a dose of from 25 μL to 250 μL of the pharmaceutical composition of claim 1.

5. The method of claim 4, wherein the dose is 100 μL of the pharmaceutical composition.

6. The method of claim 4, wherein the dose is 200 μL of the pharmaceutical composition.

7. The method of claim 4, wherein the subject has congestive heart failure or renal insufficiency.

8. The method of claim 4, wherein the dose is delivered not more than from 1 to 4 times over a six hour period.

9. The method of claim 4, wherein the subject does not receive more than a total of about 10 mg of bumetanide over a 12 hour period.

10. The method of claim 4, wherein the subject is experiencing impaired gastrointestinal absorption of oral diuretic therapy or reduced intestinal motility prior to the administering.

* * * * *